(12) United States Patent
Alonso-Alija et al.

(10) Patent No.: US 6,984,646 B2
(45) Date of Patent: Jan. 10, 2006

(54) IMIDAZOPYRIDINONES AS P38 MAP KINASE INHIBITORS

(75) Inventors: Cristina Alonso-Alija, Haan (DE); Martin Michels, Solingen (DE); Hartmut Schirok, Dortmund (DE); Karl-Heinz Schlemmer, Wuppertal (DE); Sara Dodd, Huntingdon (GB); Mary Fitzgerald, Oxfordshire (GB); John Bell, Leics (GB); Andrew Gill, Slough (GB)

(73) Assignee: Bayer Healhcare AG, Leverkusen (DE)

( * ) Notice: Subject to any disclaimer, the term of this patent is extended or adjusted under 35 U.S.C. 154(b) by 35 days.

(21) Appl. No.: 10/484,070

(22) PCT Filed: Jul. 15, 2002

(86) PCT No.: PCT/EP02/07834
§ 371 (c)(1),
(2), (4) Date: Jun. 18, 2004

(87) PCT Pub. No.: WO03/008413
PCT Pub. Date: Jan. 30, 2003

(65) Prior Publication Data
US 2004/0220208 A1 Nov. 4, 2004

(30) Foreign Application Priority Data
Jul. 18, 2001 (GB) .............................. 0117506

(51) Int. Cl.
*A61K 31/437* (2006.01)
*C07D 471/04* (2006.01)
*C07D 471/02* (2006.01)
*A61P 29/00* (2006.01)

(52) U.S. Cl. ...................... 514/292; 514/300; 514/303; 546/86; 546/84; 546/117; 546/121

(58) Field of Classification Search ................ 546/121, 546/84, 86; 514/292, 300
See application file for complete search history.

(56) References Cited

FOREIGN PATENT DOCUMENTS

| DE | 2908364 | * | 9/1980 |
|----|---------|---|--------|
| JP | 5585595 |   | 6/1980 |

OTHER PUBLICATIONS

Liverton et al. J. Med. Chem. 1999, 42: 2180–21.*
Chem. Abstracts, 1981: 47326 HCAPLUS.
Darwent Abstracts, 1980–57588C [33] WPIDS.
Japanese Patent Abstracts, 1980–085595 JAPIO.
Kubo, et al., Studies on the Synthesis of 2(1H)–Pyridone Derivatives, IV. Synthesis of Condensed Heterocyclic 2(1H)–Pyridones, UDC, 99, 880–888, (1979).
Knolker, et al., Imidazole Derivatives. Part II, Synthesis of Imidazo [1,2-a] Pyridin–5–Ones, Heterocycles, 29, 1551–1558, (1989).
Hiroshige, Novel Heterocyclic Compound, Pat. Abstracts of Japan, vol. 004, JP 55 085595 (1980).

* cited by examiner

*Primary Examiner*—Evelyn Mei Huang

(57) ABSTRACT

The invention relates to imidazopyridinones of the formula

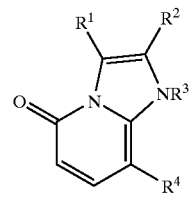

wherein the groups $R^1$, $R^2$, $R^3$, and $R^4$ are as defined in claim 1, to the process for their preparation, to pharmaceutical compositions containing them, and to a method of using them for treatment of chronic inflammatory processes in humans or animals.

10 Claims, No Drawings

IMIDAZOPYRIDINONES AS P38 MAP KINASE INHIBITORS

The present invention relates to imidazopyridinones processes for their preparation and their use in medicaments, especially for the treatment of COPD.

COPD is characterised by a neutrophils and macrophage inflammatory burden in the lung. Unlike asthma it has been shown that the inflammation (cells, IL-8, TNF) and airflow obstruction characteristic of COPD is insensitive to therapy with steroids.

The critical chemokine driving neutrophilic inflammation is believed to be IL-8, which can be released by a variety of human cells including bronchial epithelial cells, neutrophils and alveolar macrophages.

There are 3 major stress-activated protein kinase pathways 1) p38 mitogen-activated protein (MAP) kinase; 2) extracellular-regulated protein kinase (ERK); 3) c-Jun NH2 terminal kinase (JNK). Activation of human neutrophils and human bronchial epithelial cells results in a rapid activation of p38 MAP kinase which subsequently phosphorylates specific transcription factors, resulting in the synthesis and secretion of inflammatory mediators, particularly 1L-8. Studies in vitro with the reference p38 MAP kinase inhibitor, SB 203580, have shown that the release of IL-8 from activated neutrophils and bronchial epithelial cells is linked to the activation of the p38 MAP kinase cascade. The exposure of human bronchial epithelial cells to cigarette smoke extracts also appears to increase the ability of p38 MAP kinase inhibitors to reduce IL-8 release suggesting that exposure to cigarette smoke in vivo may prime the p38 MAP kinase pathway of IL-8 release. These studies suggest that inhibition of p38 MAP kinase may be involved in regulating IL-8 release through an effect on gene expression. Inhibition of p38 MAP kinase may offer an alternative approach to IL-8 antagonism, and may thus provide an effective anti-inflammatory therapy for COPD.

2(1H)-pyridone derivatives are known from Yakugaku Zasshi (1979), 99(9), 880–8 to have antiinflammatory activity.

8-benzoyl-H-imidazo[1,2,-a]pyridin-5-one and 8-benzoyl-1-methylimidazo[1,2,-a]-pyridin-5-one are known from Knölker et al. Heterocycles, 1989, 29, 1551–1558.

The present invention relates to compounds of general formula (I)

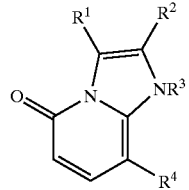

wherein
$R^1$ represents hydrogen, halogen, $C_1$–$C_6$-alkyl, $C_6$–$C_{10}$-aryl, $C_5$–$C_8$-heteroaryl, $C_3$–$C_8$-cycloalkyl, $C_1$–$C_6$-alkoxy, wherein $R^1$ can optionally be substituted with 1 to 3 substituents $R^{1-1}$, wherein $R^{1-1}$ is halogen, amino, mono- or di-$C_1$–$C_6$-alkylamino, $C_1$–$C_6$-alkoxy,
$R^2$ represents hydrogen, halogen, $C_1$–$C_6$-alkyl, $C_6$–$C_{10}$-aryl, $C_5$–$C_8$-heteroaryl, $C_3$–$C_8$-cycloalkyl, $C_1$–$C_6$-alkoxy, wherein $R^2$ can optionally be substituted with 1 to 3 substituents $R^{2-1}$, wherein $R^{2-1}$ is halogen, amino, mono- or di-$C_1$–$C_6$-alkylamino, $C_1$–$C_6$-alkoxy,
or
$R^1$ and $R^2$ together with the carbon atoms to which they are attached form a $C_6$–$C_{10}$-aryl-, $C_5$–$C_8$-heteroaryl-, $C_5$–$C_8$-cycloalkyl-, or $C_5$–$C_8$-heterocyclyl-ring,
wherein the ring is optionally substituted with $C_1$–$C_6$-alkyl, $C_1$–$C_6$-alkoxy, halogen, cyano, amino, mono- or di-$C_1$–$C_6$-alkylamino, $COR^{2-2}$, wherein
$R^{2-2}$ is OH, $C_1$–$C_6$-alkoxy, $C_6$–$C_{10}$-aryloxy, amino, mono- or di-$C_1$–$C_6$-alkyl-amino,
$R^3$ represents hydrogen or $C_1$–$C_6$-alkyl,
$R^4$ represents —$COR^{4-1}$, wherein
$R^{4-1}$ represents $C_6$–$C_{10}$-aryl or heteroaryl,
wherein $R^{4-1}$ can optionally be substituted with 1 to 3 substituents selected from the group consisting of halogen, amino, $C_1$–$C_6$-alkyl, $C_1$–$C_6$-alkoxy, mono or di-$C_1$–$C_6$-alkylamino, trifluoromethyl, cyano, nitro and hydroxy,
with the proviso, that the compound is not
8-benzoyl-H-imidazo[1,2,-a]pyridin-5-one or 8-benzoyl-1-methylimidazo[1,2,-a]pyridin-5-one,
or pharmaceutically acceptable salts thereof.

In the context of the present invention, the substituents, if not stated otherwise, in general have the following meaning:

Alkyl in general represents a straight-chain or branched hydrocarbon radical having 1 to 6 carbon atoms. Non-limiting examples include methyl, ethyl, propyl isopropyl, butyl, isobutyl, pentyl, isopentyl, hexyl, isohexyl. The same applies to radicals such as alkylcarbonylamino or $C_1$–$C_6$-alkylamino.

Alkoxy in general represents a straight-chain or branched hydrocarbon radical having 1 to 6 carbon atoms and bound via an oxygen atom. Non-limiting examples include methoxy, ethoxy, propoxy, isopropoxy, butoxy, isobutoxy, pentoxy, isopentoxy, hexoxy, isohexoxy. The terms "alkoxy" and "alkyloxy" are used synonymously.

Cycloalkyl in general represents a cyclic hydrocarbon radical having 3 to 8 carbon atoms. Cyclopropyl, cyclopentyl and cyclohexyl are preferred. Non-limiting examples include cyclopentyl, cyclohexyl, cycloheptyl and cyclooctyl.

Aryl represents a 6- to 10-membered, mono- or bicyclic ring system, which is aromatic at least in one ring. Examples are: phenyl, naphtyl.

In the context of the present invention, heterocyclyl stands for a a saturated or partially unsaturated heterocyclic ring which can contain 1 to 3 heteroatoms selected independently from the group consisting of nitrogen, oxygen or sulfur such as tetrahydrofuran, pyrrolidin, piperidin, morpholin. It can be attached via a ring nitrogen atom ("N-bound")

In the context of the present invention, a 5- to 10-membered aromatic heterocyclic ring ("heteroaryl"), which can contain 1 to 3 heteroatoms selected independently from the group consisting of nitrogen, oxygen or sulfur denotes a ring system, which is mono- or bicyclic, is aromatic at least in one ring, and which can contain 1 to 3 of the above-mentioned heteroatoms. It can be attached via a ring carbon atom. Examples are: furan, pyridine, benzofuran, pyrazol, oxadiazol or benzoxazol.

Suitable pharmaceutically acceptable salts of the compounds of the present invention that contain an acidic moiety include addition salts formed with organic or inorganic bases. The salt forming ion derived from such bases can be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkylamines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described above and are preferred.

Suitable pharmaceutically acceptable salts of the compounds of the present invention that contain a basic moiety include addition salts formed with organic or inorganic acids. The salt forming ion derived from such acids can be halide ions or ions of natural or unnatural carboxylic or sulfonic acids, of which a number are known for this purpose. Examples include chlorides, acetates, trifluoroacetates, tartrates, or salts derived from amino acids like glycine or the like. The physiologically acceptable salts such as the chloride salts, the trifluoroacetic acid salts and the amino acid salts can be used medicinally as described below and are preferred.

Surprisingly, the compounds of the present invention show p38 MAP kinase inhibitory activity and are therefore suitable for the preparation of medicaments for the treatment of diseases associated with p38 MAP kinase. They may thus provide an effective treatment of acute and chronic inflammatory processes such as rheumatoid arthritis, osteoarthritis, spondylitis, bone resorption diseases, sepsis, septic shock, toxic shock syndrome, endotoxic shock, tuberculosis, atherosclerosis, diabetes, adult respiratory distress syndrome (ARDS), chronic obstructive pulmonary disease (COPD), asthma, fever, periodontal diseases, ulcerative colitis, pyresis, Alzheimer's and Parkinson's diseases, especially of COPD.

If radicals in the compounds according to the invention are substituted, the radicals, unless otherwise specified, can be substituted by one or more identical or different substituents. A substitution with up to three identical or different substituents is preferred. Very particular preference is given to substitution with one substituent.

In another embodiment, the present invention relates to compounds according to general formula (I), wherein
$R^1$ represents hydrogen, $C_1$–$C_6$-alkyl or $C_3$–$C_8$-cycloalkyl, wherein $R^1$ can optionally be substituted with 1 to 3 substituents $R^{1-1}$, wherein $R^{1-1}$ is $C_1$–$C_6$-alkoxy,
$R^2$ represents hydrogen, $C_1$–$C_6$-alkyl or $C_3$–$C_8$-cycloalkyl, wherein $R^2$ can optionally be substituted with 1 to 3 substituents $R^{2-1}$, wherein $R^{2-1}$ is $C_1$–$C_6$-alkoxy,
or
$R^1$ and $R^2$ together with the carbon atoms to which they are attached form a $C_6$–$C_{10}$-aryl- or $C_5$–$C_8$-cycloalkyl-ring, wherein the ring is optionally substituted with $C_1$–$C_6$-alkyl, $C_1$–$C_6$-alkoxy, halogen,
$R^3$ represents hydrogen,
$R^4$ represents —COR$^{4-1}$, wherein represents $C_6$–$C_{10}$-aryl or heteroaryl,
$R^{4-1}$ represents $C_6$–$C_{10}$-aryl or heteroaryl,
wherein $R^{4-1}$ can optionally be substituted with 1 to 3 substituents selected from the group consisting of halogen, $C_1$–$C_6$-alkyl, $C_1$–$C_6$-alkoxy, trifluoromethyl or hydroxy,
with the proviso, that the compound is not 8-benzoyl-H-imidazo[1,2,-a]pyridin-5-one or 8-benzoyl-1-methylimidazo[1,2,-a]pyridin-5-one or pharmaceutically acceptable salts thereof.

In another embodiment, the present invention relates to compounds according to general formula (I), wherein
$R^1$ represents hydrogen or $C_1$–$C_6$-alkyl,
$R^2$ represents hydrogen or $C_1$–$C_6$-alkyl,
or
$R^1$ and $R^2$ together with the carbon atoms to which they are attached form a $C_5$–$C_8$-cycloalkyl-ring, wherein the ring is optionally substituted with $C_1$–$C_6$-alkyl,
$R^3$ represents hydrogen,
$R^4$ represents —COR$^{4-1}$, wherein
$R^{4-1}$ represents $C_6$–$C_{10}$-aryl or heteroaryl,
wherein $R^{4-1}$ can optionally be substituted with 1 to 3 substituents selected from the group consisting of halogen, $C_1$–$C_6$-alkyl,
with the proviso, that the compound is not 8-benzoyl-H-imidazo[1,2,-a]pyridin-5-one or 8-benzoyl-1-methylimidazo[1,2,-a]pyridin-5-one or pharmaceutically acceptable salts thereof.

In another embodiment, the present invention relates to compounds according to general formula (I), wherein $R^3$ is hydrogen.

In another embodiment, the present invention relates to compounds of general formula (I), wherein $R^4$ is —C(O)$C_6H_5$, wherein $R^4$ can optionally be substituted with 1 to 3 substituents selected from the group consisting of halogen, amino, $C_1$–$C_6$-alkyl, $C_1$–$C_6$-alkoxy, mono or di-$C_1$–$C_6$-alkylamino, trifluoromethyl, cyano, especially halogen and $C_1$–$C_6$-alkyl, most especially 2,4-difluoro.

In another embodiment, the present invention relates to compounds according to general formula (I), wherein $R^1$ and $R^2$ together with the carbon atoms to which they are attached form a substituted cyclohexyl-ring, especially a cyclohexyl-ring substituted with one or two methyl groups.

In another embodiment, the present invention relates to compounds according to general formula (I), wherein $R^1$ and $R^2$ represent ethyl.

In another embodiment, the present invention relates to compounds according to general formula (I), wherein $R^1$ and $R^2$ do not both represent hydrogen.

In another embodiment, the present invention relates to compounds of general formula (I) with IC$_{50}$-values [p38 map kinase] of less than 10 $\mu$M, especially less than 1 $\mu$M and very especially less than 0,5 $\mu$M.

A. BIOLOGICAL EXPERIMENTS

The in vitro-properties of the compounds can be shown in the following experiments:
P38 map Kinase Assay The assay makes use of the serine/threonine protein kinase SPA [33-P]+assay kit from Amersham Pharmacia Biotech. The assay is a homogeneous technique using SPA technology for the quantification of serine threonine kinase activity.

It is based on the p38 map kinase catalysed transfer of the γ-phosphate group of the [γ-$^{33}$P] ATP to the substrate, biotinylated myelin basic protein (MBP). The resulting [$^{33}$P]-labelled biotinylated product is trapped on a PVT SPA bead containing scintillant which has been surface coated with streptavidin.

The beads are allowed to settle to eliminate high background, and therefore only $^{33}$P labelled product attached to the SPA bead is detected.

The assay is carried out in the presence and absence of test compounds to determine their effect on p38 map kinase activity.

A Test Protocol is as Follows:
1. SPA assay kit (Amersham). Components:
   Assay buffer (store frozen)
   Stop solution (store frozen)
   Streptavidin coated SPA beads—reconstitute with 5 mls of PBS. (50 mg/ml). (Store in fridge)

2. p38 map kinase enzyme SCRD (500 µg/ml)–aliquoted in 1.5 mls.
   dilute 1:10 to 50 µg/ml
   1 plate: –110 µl (stock 500 µg/ml)+9901 µl PBS.
3. Assay reagent:
   for 1 plate: –504 µl Assay buffer (500 Mm MOPS pH7.2, 10 µM ATP,
   50 mM MgCl$_2$, 25 µM biotinylated myelin basic protein (MBP)).
   2513.4 µl Water
   1.1 µl 33-p-ATP (10 µCi/l) (on activity date/adjust for activity date)
   4.534 µl×10-2M ATP in water
4. Stop solution:
   for 1 plate: –265.92 µl streptavidin coated beads (50 mg/ml)
   1651.68 µl stop buffer (500 µM ATP, 50 mM EDTA 1% Triton X-100)
   7084.32 µl PBS.
1. Add 10 µcompound Dilutions (5× final conc) Test wells.
2. Add 10 µl 12.5% DMSO to control/blank wells.
3. Add 10 µl enzyme (50 µg/ml)–final conc 500 ng/well
4. Add 10 µPBS to blank wells.
5. Add 30 µL of assay reagent to each well. (final conc 10 µM ATP, 2.5 µM substrate)
6. Mix well on plate shaker
7. Incubate 90 min (30° C.)
8. Add 75 µl of stop solution to each well (final conc 55 µM ATP)
9. Spin plate: –3 min/1600 rpm/20° C. (alternatively leave to settle overnight)
10. Read in Microbeta, Protocol SPA paralux 3.
    Representative Data are given in table 1:

TABLE 1

| Ex. No. | IC$_{50}$ (nM) |
|---|---|
| 1 | 518 |
| 2 | 329 |
| 3 | 235 |
| 5 | 111 |
| 38 | 96 |

Description of the Functional Assays

Neutrophils are isolated from human blood via discontinuous Percoll gradient and seeded at 1×10$^6$ cells/well. Compounds are added, and the cells are incubated for 1 h at 37° C. After 1 h, cells are stimulated with TNF-alpha (25 ng/ml final conc.) for 18 h.

Supernatants are harvested and analysed for IL-8 content by ELISA.

The suitability of the compounds for the prevention and treatment of diseases can be shown in the following in vivo-model:

Description of the in vivo Model
Mouse Acute Lipopolysaccharide (LPS) Method
Animals (species, strain): Mouse, Balb/C
Dosing vehicle: Solutol HS15 (polyethylene glycol 660 12-hydroxystearate; BASF, Germany)/ethanol or tylose (carboxymethylcellulose; Sigma, Germany) as an excipient mixed with either water (enteral studies) or saline (parenteral studies).
Method of preparation of test substance: The test substance is ground into a fine powder using a pestle and mortar and dissolved in the excipient. Water or saline is then added to achieve the desired dosing concentration.

Experimental Protocol
1. Compound administration. Mice are randomly assigned into groups and administered vehicle or test substance, by an enteral or parenteral route, on one occasion within 24 hours of inflammatory challenge, and up to two occasions in the 24 hours thereafter.
2. Inflammatory challenge. Mice are lightly anaesthetised (halothane/O$_2$) and intra nasally administered either saline or LPS (0.1 µg to 10 µg; *Pseudomonas aeruginosa*; Sigma) at a dose volume of 25 µl/nare.
3. Bronchoalveolar lavage (BAL). Within 24 hours of inflammatory challenge, mice are euthanised using sodium pentabarbitone (ip.). BAL fluid is then collected into heparinised phosphate buffered saline and centrifuged. The pellet can be used for the cell counting of neutrophils; and the supernatent assayed for KC (R&D Systems), macrophage inflammatory protein 2 (R&D Systems) or tumour necrosis factor-alpha (Biosource International) using commercially available ELISA kits. Lung tissue can also be removed for later myeloperoxidase assay as an index of neutrophil recruitment into the lungs.

Health Status monitoring: Mice are monitored for adverse effects.

Statistical methods: Data are analysed using an appropriate statistical test and considered significant at the p<0.05 level.

In another embodiment, the present invention relates to the composition containing at least one compound of general formula (I) and a pharmacologically acceptable diluent and the use of such composition for the treatment of acute and chronic inflammatory processes as well as the process for the preparation of such compositions, characterized in that the compounds of general formula (I) together with customary auxiliaries in brought into a suitable application form. The compounds of general formula (I) are therefor useful for the preparation of medicaments, especially of medicaments for the treatment of acute and chronic inflammatory processes, especially COPD.

For the treatment of the above-mentioned diseases, the compounds according to the invention can exhibit non-systemic or systemic activity, wherein the latter is preferred. To obtain systemic activity the active compounds can be administered, among other things, orally or parenterally, wherein oral administration is preferred.

For parenteral administration, forms of administration to the mucous membranes (i.e. buccal, lingual, sublingual, rectal, nasal, pulmonary, conjunctival or intravaginal) or into the interior of the body are particularly suitable. Administration can be carried out by avoiding absorption (i.e. intracardiac, intra-arterial, intravenous, intraspinal or intralumbar administration) or by including absorption (i.e. intracutaneous, subcutaneous, percutaneous, intramuscular or intraperitoneal administration).

For the above purpose the active compounds can be administered per se or in administration forms.

Suitable administration forms for oral administration are, inter alia, normal and enteric-coated tablets, capsules, coated tablets, pills, granules, pellets, powders, solid and liquid aerosols, syrups, emulsions, suspensions and solutions. Suitable administration forms for parenteral administration are injection and infusion solutions.

The active compound can be present in the administration forms in concentrations of from 0.001–100% by weight; preferably the concentration of the active compound should be 0.5–90% by weight, i.e. quantities which are sufficient to allow the specified range of dosage.

The active compounds can be converted in the known manner into the above-mentioned administration forms using inert non-toxic pharmaceutically suitable auxiliaries, such as for example excipients, solvents, vehicles, emulsifiers and/or dispersants.

The following auxiliaries can be mentioned as examples: water, solid excipients such as ground natural or synthetic minerals (e.g. talcum or silicates), sugar (e.g. lactose), non-toxic organic solvents such as paraffins, vegetable oils (e.g. sesame oil), alcohols (e.g. ethanol, glycerol), glycols (e.g. polyethylene glycol), emulsifying agents, dispersants (e.g. polyvinylpyrrolidone) and lubricants (e.g. magnesium sulphate).

In the case of oral administration tablets can of course also contain additives such as sodium citrate as well as additives such as starch, gelatin and the like. Flavour enhancers or colorants can also be added to aqueous preparations for oral administration.

For the obtainment of effective results in the case of parenteral administration it has generally proven advantageous to administer quantities of about 0.001 to 100 mg/kg, preferably about 0.01 to 1 mg/kg of body weight. In the case of oral administration the quantity is about 0.01 to 100 mg/kg, preferably about 0.1 to 10 mg/kg of body weight.

It may nevertheless be necessary to use quantities other than those mentioned above, depending on the body weight concerned, the method of administration, the individual response to the active compound, the type of preparation and the time or interval of administration.

In another embodiment, the present invention relates to a process for synthesizing the compounds of general formula (I), characterized in that compounds of general formula (II)

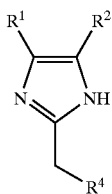

(II), wherein $R^1$, $R^2$ and $R^4$ have the meaning described above, are reacted

[A] with $C_1$–$C_6$-alkyl propiolate in the presence of a base, or
[B] with $C_1$–$C_6$-alkyl propiolate in absence of a base, or
[C] with 3-oxopropionic $C_1$–$C_6$-alkyl ester or
[D] with compounds of general formula (IV)

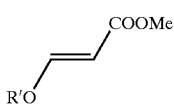

(IV), wherein R' is $C_1$–$C_6$-alkyl or $C_1$–$C_6$-alkylcarbonyl, or
[E] with propiolic acid in the presence of carbonyldiimidazole.

Alternatively, compounds (I), wherein $R^1$ is halogen, can be obtained

[F] by reaction of compounds (V)

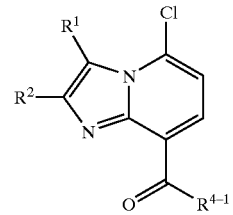

(V), wherein R' is halogen,
with potassium hydroxyde.

Suitable solvents for the processes [A] to [F] are generally customary organic solvents which do not change under the reaction conditions. These include ethers such as diethyl ether, dioxan or tetrahydrofuran, ethylacetate, acetone, dimethylsulfoxide, dimethylformamide or alcohols such as methanol, ethanol, propanol, butanol or t-butanol, or halogenohydrocarbons such as dichloromethane, dichloroethane, trichloromethane or tetrachloromethane. Preferred for [A] and [B] is methanol, for [C] and [D] toluene or toluene/ethanol, for [E] tetrahydrofuran and for [F] water/ethanol.

Suitable bases for process [A] are generally inorganic or organic bases. These preferably include alkali alcoholates, such as sodium methylate in methanol. The base is employed in an amount from 1 mol to 10 mol, preferably from 1.0 mol to 4 mol, relative to 1 mol of the compound of the general formula (II).

Process [C] and [D] can be carried out in the presence of molecular sieves (4 Å).

The processes [A] to [F] are in general carried out in a temperature range from −30° C. to +100° C., preferably from −10° C. to +50° C. Most reactions can be carried out at room temperature.

The processes [A] to [F] are generally carried out at normal pressure. However, it is also possible to carry it out at elevated pressure or at reduced pressure (for example in a range from 0.5 to 5 bar).

The compounds of general formula (II) can be synthesized by reacting compounds of general formula (III)

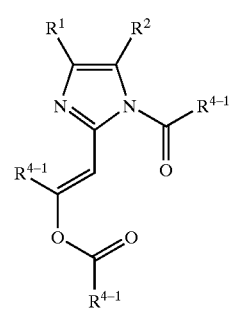

(III), wherein $R^{4-1}$ has the meaning described above, in the presence of an acid. Alternatively, this reaction can be carried out with morpholine in methanol.

The compounds of general formula (III) can be synthesized by reacting compounds of general formula (VI)

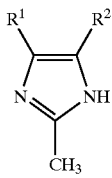

(VI), wherein $R^1$ and $R^2$ have the meaning described above, with an acid chloride R4-1-COCl in the presence of a base like triethylamine, solvent acetonitril, reflux.

The compounds of general formula (V) can be synithesized by reacting compounds of general formula (VI)

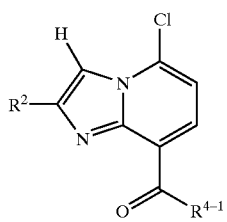

(VI)

with halogen, e.g. bromine.

The compounds of general formula (VI) can be synthesized by reacting compounds of general formula (I), wherein $R^1$ is hydrogen, with phosporoxychloride. Compounds of general formula (I), wherein $R^1$ is hydrogen, are prepared as described above with methods [A] to [E].

Compounds (VI) can be obtained (as free bases or hydrochloride)

by reaction of a vicinal diketone with acetaldehyde and ammonium hydroxyde in ethanol as described in N. Kuhn et al. Z. Naturforsch. B, 1991, 12, 1706–1712.

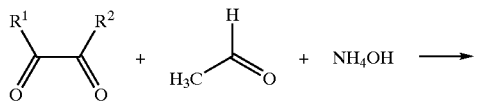

(VI)

by reaction of a vicinal diketone with ammonium acetate in glacial acetic acid

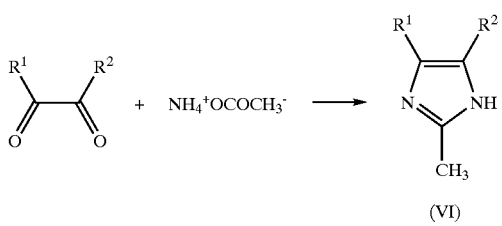

(VI)

by reaction of an alpha-bromoketone with copper acetate, ammonium hydroxide and acetaldehyde

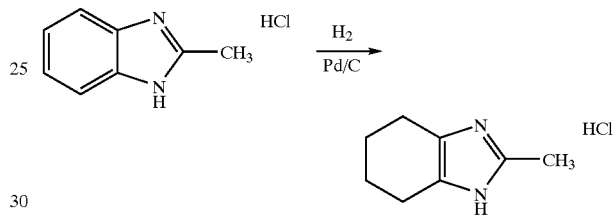

(VI)

2-methyl-4,5,6,7-tetrahydro-1H-benzimidazole can be obtained by catalytic hydrogenation (Pd/C) of the corresponding 2-methylbenzimidazoles, preferred as hydrochlorides, in ethanol or glacial acetic acid preferred under pressure (eg. as described by Ohta et al. Chem. Pharm. Bull. 1996, 44, 991–999).

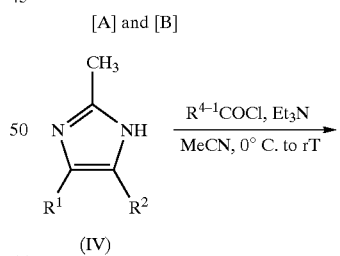

2-Methylbenzimidazoles can be synthesised from the corresponding 2-amino-phenylamines by known procedure (eg. with 2,4-pentandione with hydrochloric acid).

The compounds of general formula (I), wherein $R^3$ is alkyl, are prepared by reacting compounds of general formula (I), wherein $R^1$ is hydrogen, with alkyl halide, especially alkyl iodide in the presence of sodium hydride.

The synthesis of 2-methyltetrahydrobenzimidazoles can be achieved by catalytic hydrogenation of the corresponding 2-methylbenzimidazoles.

The processes can be illustrated by the following schemes [A] to [D]:

[A] and [B]

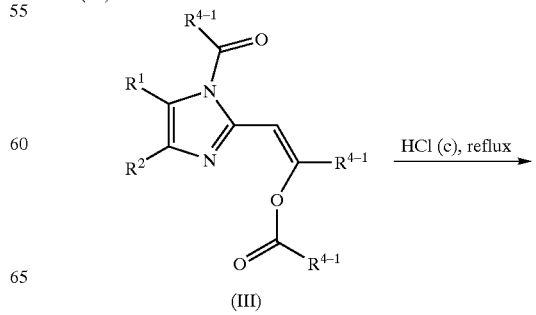

(III)

-continued

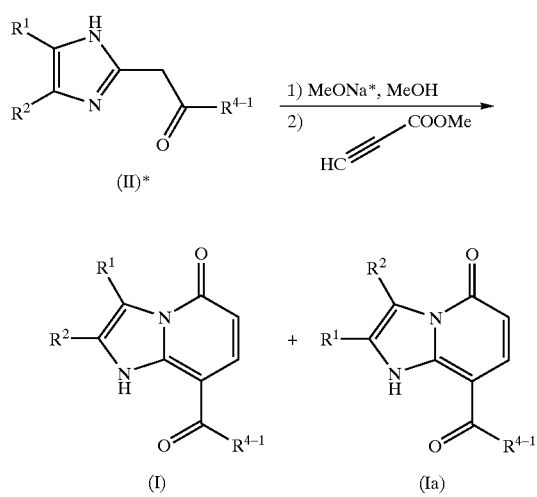

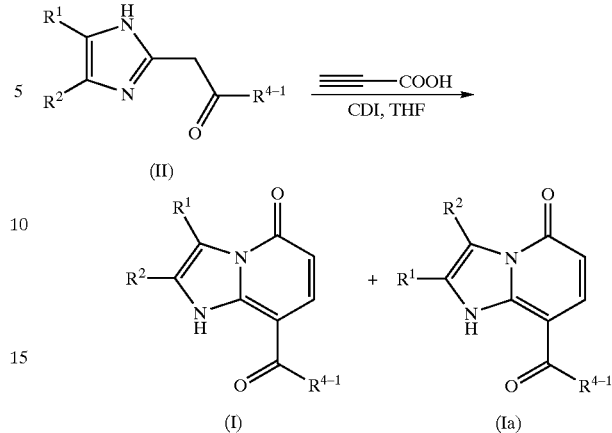

(H. J. Knölker et al. *Heterocycles*, 1989, 29, 1551–1558)
*Depending on the reaction conditions, the compounds of formula (II) can be obtained in form of their hydrochlorides. In this case, the use of a base in 1) is necessary.

[C]

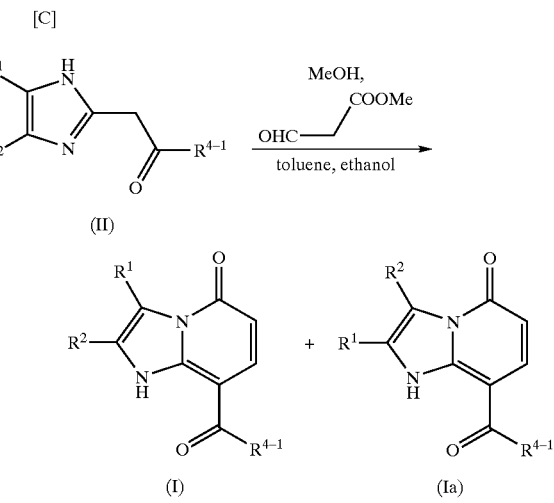

[D]

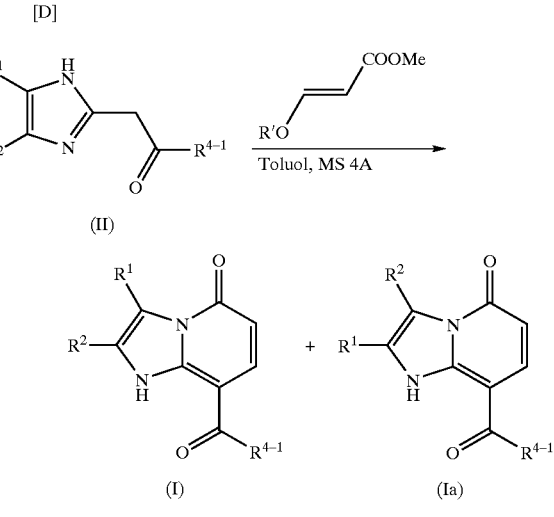

[E]

The regioisomeric product (Ia) is usually obtained in certain amounts, depending on the reaction conditions.

Carbonyl compounds (II) can also be present in form of their enolates.

Synthesis of 2-methylimidazoles: general as described in the literature or, e.g. analogue N. Kuhn et al. Z. Naturforsch.B, 1991, 12, 1706–1712.

B. EXAMPLES

Analytical Methods
HPLC-Methods
Method A
Instrument: HP 1100 with DAD-Detection
Column: Kromasil RP-18, 60 mm×2 mm, 3.5 µm
Eluent: A=5 ml Perchloric acid/1 H2O, B=Acetonitrile
Gradient: 0 min 2% B, 0.5 min 2% B, 4.5 min 90% B 6.5 min 90% B
Flow: 0.75 ml/min, Temp.:30 Grad C, Detection UV 210 nm
LC/MS-methods
Method C
Instrument: Micromass Quattro LCZ, HP 1100;
Column: Symmetry C18, 50 mm×2.1 mm, 3.5 µm;
Eluent A: Acetonitril+0.1% formic acid, Eluent B: Wasser+ 0.1% formic acid;
Gradient: 0.0 min 10% A→4.0 min 90% A→4.0 min 90% A;
Column oven: 40° C., Flow: 0.5 ml/min, UV-Detection: 208–400 nm
Method B
Instrument: Micromass Platform LCZ, HP1100;
Column: Symmetry C18, 50 mm×2.1 mm, 3.5 µm;
Eluent A: Acetonitril+0.1% formic acid, Eluent B: Wasser+ 0.1% formic acid;
Gradient: 0.0 min 10% A→4.0 min 90% A→4.0 min 90% A;
Column oven: 40° C., Flow: 0.5 ml/min, UV-Detection: 208–400 nm
Method D
Instrument: Finnigan MAT 900S, TSP: P4000, AS3000, UV30000HR;
Column: Symmetry C 18, 150 mm×2.1 mm, 5.0 µm;
Eluent A: Acetonitrile; Eluent B: Water+0.3 g 30% ige hydrochlorid acid, Eluent C: Water
Gradient: 0.0 min 2% A, 49% B, 49% C→2.5 min 95% A, 2.5% B, 2.5% C→5.0 min 95% A, 2.5% B, 2.5% C;
Column oven: 70° C., Flow: 0.0 min–2.5 min→0.9 ml/min, 2.5 min–5.0 min→1.2 ml/min, UV-Detection: 210 nm
The Following Abbreviations are Used in the Descriptions
ACN=acetonitrile
aq.=aqueous
CDI 1,1-carbonyldiimidazol DCM=dichloromethane
DMF=dimethylsulfoxide
HPLC=High Pressure Liquid Chromatography
min.=minute
MS=mass spectroscopy
MS4A molecular sieves 4 Angstrom
PE=petroleumether
$R_t$=retention time
rt=room temperature
THF=tetrahydrofuran
% of th.=% of theory

EXAMPLES

The percentages in the tests and examples which follows are, unless otherwise stated, by weight; parts are by weight. Solvent ratios, dilution ratios and concentrations reported for liquid/liquid solutions are each based on the volume.

EXAMPLE I 2-(1-Benzoyl-1H-benzimidazol-2-yl)-1-phenylethenyl benzoate

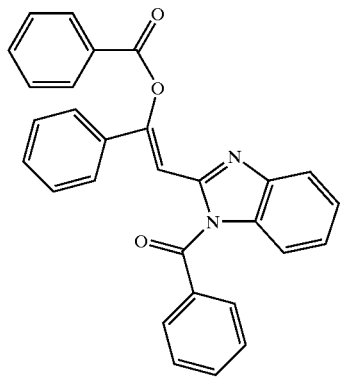

5.00 g (0.04 mol) 2-methyl-1H-benzimidazol are dissolved in 50 ml acetonitrile and 13.4 g (0.13 mol) TEA are added. At 20° C. 17.55 g (0.12 mol) benzoylchloride are added dropwise. The mixture is stirred at RT overnight. The mixture is concentrated under vacuum and 100 ml toluene are added to the residue. The solution is washed with 20 ml saturated sodium chloride aqueous solution and the organic materials are dried over magnesium sulfate, filtered and concentrated under vacuum. The residue is washed with petrol ether, the product is filtered and dried. The filtrate is concentrated under vacuum, the residue is washed with petrol ether and the product is filtered and dried to yield a second charge of product. The procedure is repeated a third time to obtain a total of 14.6 g (80% o. th.) (Z)-2-(1-benzoyl-1H-benzimidazol-2-yl)-1-phenylethenyl benzoate.

$^1$H-NMR (300 MHz, DMSO-d$_6$): δ=7.0–8. 28 (m)

EXAMPLE II 2-(1H-Benzimidazol-2-yl)-1-phenylethanone hydrochloride

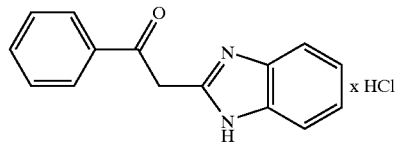

5.73 g (0.01 mol) of the compound of Example I are refluxed 2 h in 115 ml concentrated hydrochloric acid. The mixture is cooled to rT and concentrated under vacuum. The residue is washed with petrol ether and the product is filtered, stirred with toluene and filtered again, washed with petrol ether, filtered and dried to yield 3.6 g (96% o.th.) 2-(1H-Benzimidazol-2-yl)-1-phenylethanone.

$^1$H-NMR (300 MHz, DMSO-d$_6$): δ=3.74 (s, 2H), 7.27–8.03 (m, 7H), 8.12 (d, 2H), 14.1 (bs, 1H)

EXAMPLE III

2-[1-(4-Fluorobenzoyl)-4,5-dimethyl-1H-imidazol-2-yl]-1-(4-fluorophenyl)-ethenyl4-fluorobenzoate

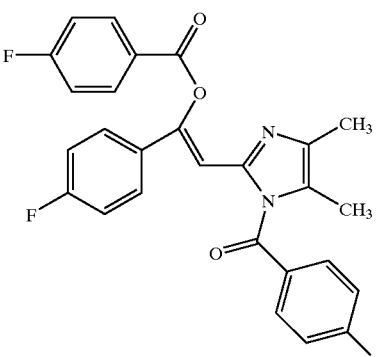

3.00 g (27.23 mmol) 2,4,5-trimethyl-1H-imidazol and 9.37 g (92.59 mmol) TEA are dissolved in 50 ml acetonitrile and cooled to 0° C. 14.25 g (89.87 mmol) 4-fluorobenzoylchloride are added dropwise and the mixture is stirred 2 h at RT and let stand overnight. The solvent is removed under vacuum, the residue is dissolved in toluene and washed twice with water. The organic phase is filtered through Tonsil (K60) and concentrated under vacuum. The product is used without further purification.

EXAMPLE IV 2-(4,5-Dimethyl-1H-imidazol-2-yl)-1-(4-fluorophenyl)ethanone hydrochloride

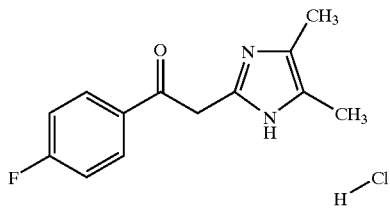

12.97 g crude compound of Example III are refluxed 1.5 h in 200 ml concentrated hydrochloric acid. The mixture is cooled to rT and 200 mL water are added. The solution is extracted twice with toluene and the aqueous phase is concentrated under vacuum. The residue is stirred with ethanol, filtered, washed once with ethyl acetate and once with petrol ether and dried to yield 0.74 g (10% of th.) 2-(4,5-Dimethyl-1H-imidazol-2-yl)-1-(4-fluorophenyl)ethanone hydrochloride.

$^1$H-NMR (200 MHz, DMSO-$d_6$): δ=2.12–2.28 (m, 6H), 4.85 (s, 2H), 7.46 (t, 2H), 8.1–8.22 (m, 2H), 13.88 (s, 1H)

EXAMPLE V

2-[1-(2-Fluorobenzoyl)-4,5-dimethyl-1H-imidazol-2-yl]-1-(2-fluorophenyl)ethenyl 2-fluorobenzoate

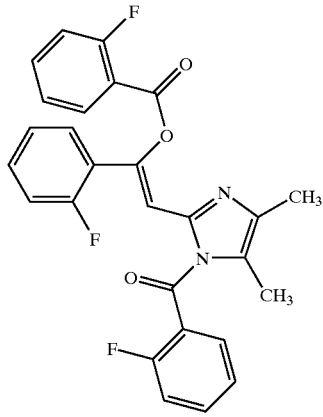

3.00 g (27.23 mmol) 2,4,5-trimethyl-1H-imidazol and 9.37 g (92.59 mmol) TEA are dissolved in 50 ml acetonitrile and cooled to 0° C. 14.25 g (89.87 mmol) 2-fluorobenzoylchloride are added dropwise and the mixture is stirred 2 h at RT and let stand overnight. The solvent is removed under vacuum, the residue is dissolved in toluene and washed twice with water. The organic phase is filtered through Tonsil (K60) and concentrated under vacuum. The product is used without further purification.

EXAMPLE VI 2-(4,5-Dimethyl-1H-imidazol-2-yl)-1-(2-fluorophenyl)ethanone hydrochloride

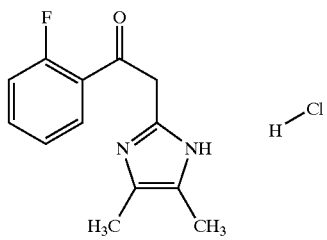

12.97 g crude crude compound of Example V are refluxed 1.5 h in 200 ml concentrated hydrochloric acid. The mixture is cooled to rT and 200 mL water are added. The solution is extracted twice with toluene and the aqueous phase is concentrated under vacuum. The residue is stirred with ethanol, filtered, washed once with ethyl acetate and once with petrol ether and dried to yield 1.04 g (14% of th.) 2-(4,5-Dimethyl-1H-imidazol-2-yl)-1-(2-fluorophenyl)ethanone hydrochloride.

$^1$H-NMR (200 MHz, DMSO-$d_6$): δ=2.12–2.25 (m, 6H), 4.77 (m, 2H), 727–8.0 (m 4H) 13.25 (s, 1H)

EXAMPLE VII

2-[1-(3-Fluorobenzoyl)-4,5-dimethyl-1H-imidazol-2-yl]-1-(3-fluorphenyl)ethenyl-3-fluorobenzoate

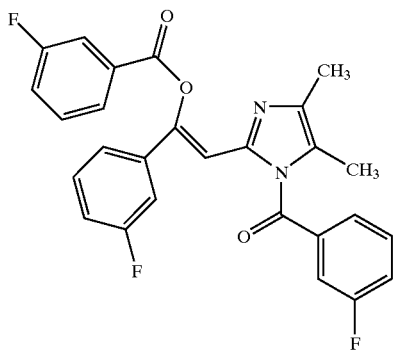

3.99 g (27.23 mmol) 2,4,5-trimethyl-1H-imidazol and 13.78 g (136.17 mmol) TEA are dissolved in 50 ml acetonitrile and cooled to 0° C. 14.25 g (89.87 mmol) 3-fluorobenzoylchloride are added dropwise and the mixture is stirred 2 h at RT and let stand overnight. The solvent is removed under vacuum, the residue is dissolved in toluene and washed twice with water. The organic phase is filtered through Tonsil (K60) and concentrated under vacuum. The product is used without further purification.

EXAMPLE VIII 2-(4,5-Dimethyl-1H-imidazol-2-yl)-1-(3-fluorophenyl)ethanone hydrochloride

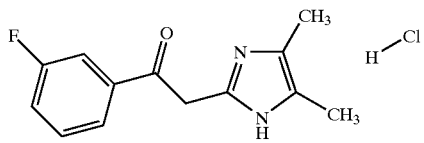

12.97 g crude compound of Example VII are refluxed 1.5 h in 200 ml concentrated hydrochloric acid. The mixture is cooled to rT and 200 mL water are added. The solution is extracted twice with toluene and the aqueous phase is concentrated under vacuum. The residue is stirred with ethanol, filtered, washed once with ethyl acetate and once with petrol ether and dried to yield 1.7 g (23% of th.) 2-(4,5-Dimethyl-1H-imidazol-2-yl)-1-(3-fluorophenyl)ethanone hydrochloride.

$^1$H-NMR (400 MHz, DMSO-d$_6$): δ=2.2 (s, 6H), 4.89 (s, 2H), 7.58–7.73 (m, 2H), 7.85–7,95 (m, 2H), 13.96 (bs, 1H)

EXAMPLE VIII 2-(1-Benzoyl4,5,6,7-tetrahydro-1H-benzimidazol-2-yl)-1-phenylethenyl benzoate

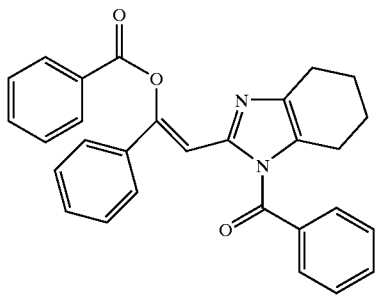

4.93 g (36.18 mmol) 2-methyl-4,5,6,7-tetrahydro-1H-benzimidazol and 12.81 g (126.62 mmol) TEA are dissolved in 50 ml acetonitrile and cooled to 0° C. 16.78 g (119.38 mmol) benzoylchloride are added dropwise and the mixture is stirred 2 h at RT and let stand overnight. The solvent is removed under vacuum, the residue is dissolved in toluene and washed twice with water. The organic phase is filtered through Tonsil (K60) and concentrated under vacuum. The product is used without further purification.

EXAMPLE IX

1-Phenyl-2-(4,5,6,7-tetrahydro-1H-benzimidazol-2-yl)ethanon hydrochloride

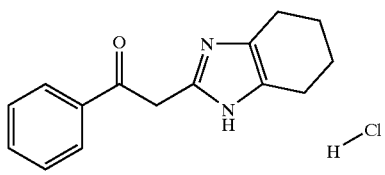

16.23 g (36.18 mmol) crude compound of Example VIII are refluxed 1.5 h in 300 ml concentrated hydrochloric acid. The mixture is cooled to rT and 200 mL water are added. The solution is extracted twice with toluene and the aqueous phase is concentrated under vacuum. The residue is stirred with ethanol, filtered, washed once with ethyl acetate and once with petrol ether and dried. The filtrate is concentrated and stirred with ethanol, the solid is filtered, washed with petrol ether and dried to yield a total of 6.55 g (65% of th.) 1-phenyl-2-(4,5,6,7-tetrahydro-1H-benzimidazol-2-yl)ethanone hydrochloride.

$^1$H-NMR (300 MHz, DMSO-d$_6$): δ=1.8 (s, 4H), 2.6 (s. 4H), 4.9 (s, 2H), 7.65 (t, 2H), 7.75 (t, 1H), 8.07 (d, 2H), 13.93 (s, 1H)

EXAMPLE X 1-(2,4-Difluorophenyl)-2-(4,6-dimethyl-4,5,6,7-tetrahydro-1H-benzimidazol-2-yl)ethanone

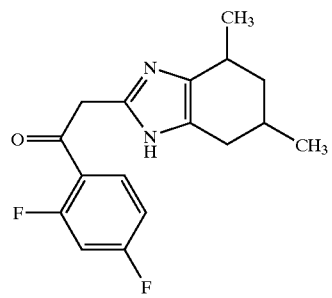

Step 1
2-Amino-3,5-dimethylphenylamine

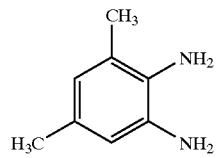

2.50 g (15.0 mmol) of 3,5-Dimethyl-2-nitroaniline are dissolved in 50 ml ethanol. To this solution 250 mg (0.23 mmol) of palladium (10% on carbon) are added under argon. The mixture is treated for 24 h with hydrogen at ambient pressure and ambient temperature. The mixture is filtrated over celite and washed with ethanol. The solvent is evaporated under vacuum to yield 2.04 g (97.1% of th.) of 2-Amino-3,5-dimethylphenylamine.

MS (ESIpos): m/z=137.3 (M+H)$^+$
$^1$H-NMR (400 MHz, CDCl$_3$) δ=2.16 (s, 3H), 2.19 (s, 3H), 3.28 (s, 4H), 6.44 (s, 1H), 6.46 (s, 1H)

Step 2
2,5,7-Trimethyl-1H-benzimidazole

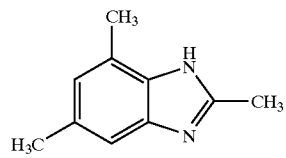

30 ml (150 mmol) of hydrogen chloride-solution (5 M in water) and 1.5 ml (14.68 mmol) 2,4-Pentandione are added to a solution of (7.34 mmol) of 2-Amino-3,5-dimethylphenylamine (example X, Step 1) in 112 ml ethanol. The reaction mixture is refluxed for 30 minutes. The solution is neutralized with saturated sodium hydrogen carbonate solution (to pH 7) and extracted with dichloromethane. The organic phases are dried over magnesium sulfate and the solvent is evaporated under vacuum to afford 2,5,7-Trimethyl-1H-benzimidazole (1.46 g) in quantitative yield.

$R_f$=0.06 (dichlormethane-ethanol 1:1)
MS (ESIpos): m/z=161.2 (M+H)$^+$
$^1$H-NMR (300 MHz, CDCl$_3$) δ=2.42 (s, 3H), 2.54 (s, 3H), 2.61 (s, 3H), 6.86 (s, 1H), 7.11 (s, 1H)

Step 3
2,5,7-Trimethyl-4,5,6,7-tetrahydro-1H-benzimidazole hydrochloride

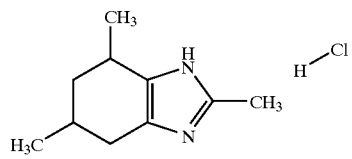

628 mg (3.92 mmol) of 2,5,7-Trimethyl-1H-benzimidazole (example X, Step 2) are dissolved in 50 ml ethanol. The solution is concentrated to 2 mL and 30 ml (0.03 mmol) hydrogen chloride solution (1M in water) are added to the concentrate. The resulting precipitate of the hydrogen chloride salt is filtrated and washed with diethylether. The precipitate is dissolved in 57.20 ml (999.13 mmol) of glacial acetic acid, 400 mg (0.38 mmol) palladium (10% on carbon) are added under argon and the reaction mixture is treated with hydrogen at a temperature of 120° C. and 80 bar pressure for 48 h. The solution is filtrated over celite and washed with glacial acid. The solvent is evaporated under vacuum to yield 413 mg (52.49% of th.) of 2,5,7-Trimethyl-4,5,6,7-tetrahydro-1H-benzimidazole hydrochlorid.

MS (CIpos): m/z=165.0 (M+H)$^+$
HPLC: $R_t$=3.56 (method A)
$^1$H-NMR (200 MHz, CDCl$_3$) δ=1.08 (d, 3H), 1.37 (d, 3H), 1.76–2.30 (m, 3H), 2.69 (s, 3H), 2.60–3.00 (m, 3H)

Step 4
(Z)-2-[1-(2,4-Difluorobenzoyl)-4,6-dimethyl-4,5,6,7-tetrahydro-1H-benzimidazol-2-yl]-1-(2,4-difluorophenyl)ethenyl 2,4-difluorobenzoate

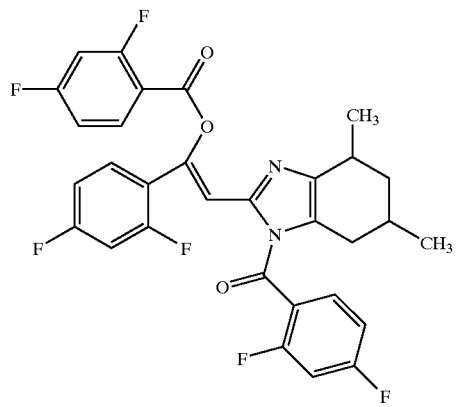

380 mg (1.89 mmol) of 2,5,7-Trimethyl-4,5,6,7-tetrahydro-1H-benzimidazole hydrochloride (example X, step 3) is dissolved in 10 ml acetonitrile. 1.19 ml (8.52 mmol) TEA is added and the solution is cooled with an ice bath. 1.10 g (6.25 mmol) of 2,4-difluorobenzoyl chloride is dropped to the reaction mixture, which then is stirred at rt for 24 h. The solvent is evaporated and water is added to the crude. After it is stirred for a few minutes the water is decanted. This step is repeated twice. The crude is transferred to the next step (example 1, step 5).

Step 5
1-(2,4-Difluorophenyl)-2-(4,6-dimethyl-4,5,6,7-tetrahydro-1H-benzimidazol-2-yl)ethanone

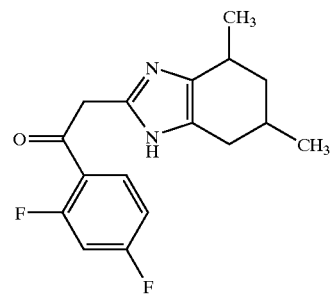

The compound of example X, step 4 is dissolved in 10 ml dioxane and 20 ml of hydrogen chloride solution (37%). The solution is heated at 100° C. for 20 h. The organic solvent is evaporated under vacuum. 30 ml water is added to the residue and the mixture is extracted with ethyl acetate. The water phase is reduced under vacuum. The residue is washed with sodium hydroxide solution to yield 150 mg (26.1% of th.) 1-(2,4-Difluoro-phenyl)-2-(4,6-dimethyl-4,5,6,7-tetrahydro-1H-benzimidazol-2-yl)ethanone.

LC-MS (method B): $R_t$=2.67 min.
MS (ESIpos) m/z=305.4 (+H)$^+$
$^1$H-NMR (300 MHz, DMSO-d$_6$) δ=1.06 (d, 3H), 1.18 (d, 3H), 1.76–1.93 (m, 2H), 2.04–2.13 (m, 1H), 2.15–2.20 (m, 1H), 2.52–2.67 (m, 2H), 5.98 (d, 1H), 7.15 (t, 1H), 7.28 (t, 1H), 7.86 (q, 1H) (characterised as enolate)

EXAMPLE XI 1-(2,4-Difluorophenyl)-2-(4-methyl-4,5,6,7-tetrahydro-1H-benzimidazol-2-yl)ethanone

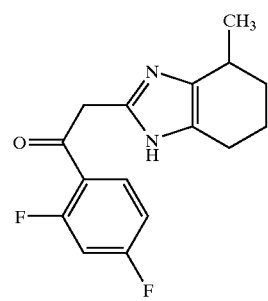

Step 1
2,4-Dimethyl-4,5,6,7-tetrahydro-1H-benzimidazole

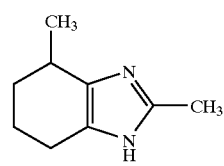

20.0 g (0.159 mol) of 3-Methyl-1,2-cyclohexanedione and 183.31 g (2.38 mol) of ammoniumacetate are dissolved in 760 ml DMSO. A solution of 27.94 g (0.34 mol) acetaldehyde dissolved in 40 ml DMSO is dropped to the reaction mixture. The reaction is heated for 20 minutes to 40° C., 20 minutes to 60° C. and 40 minutes to 80° C. The reaction is allowed to cool down to rt. 2.5 l saturated sodium chloride solution and ammonia are added to reach a pH of 8–9. The solution is extracted with ethyl acetate and the organic phases are dried over sodium sulfate. The solvent is evaporated under vacuum. The crystals are filtrated and washed with ethyl acetate and diethyl ether to yield 10.3 g (43.3% of th.) 2,4-Dimethyl-4,5,6,7-tetrahydro-1H-benzimidazole.

$^1$H-NMR (300 MHz, DMSO-d$_6$) δ=1.08 (d, 3H), 1.20 (m, 1H), 1.55 (m, 1H), 1.80 (m, 2H), 2.15 (s, 3H), 2.30 (m, 2H), 2.60 (m, 1H), 11.20 (bs, 1H)

Step 2
1-(2,4-Difluorophenyl)-2-(4-methyl-4,5,6,7-tetrahydro-1H-benzimidazol-2-yl)ethanone

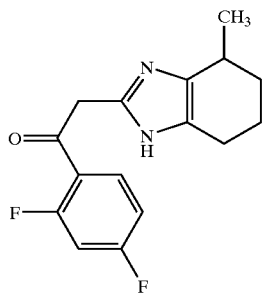

The compound is prepared as described in example X (step 4 and 5) with 1.00 g (6.66 mmol) 2,4-Dimethyl-4,5,6,7-tetrahydro-1H-benzimidazole (example XI, step 1), 3.88 g (21.97 mmol) of 2,4-difluorobenzoyl chloride and 2.36 g (23.30 mmol) of TEA in 20 ml acetonitrile. The crude intermediate is directly transformed into 1-(2,4-Difluorophenyl)-2-(4methyl-4,5,6,7-tetrahydro-1H-benzimidazol-2-yl)ethanone to yield 1.51 g (78.1% of th.).

$^1$H-NMR (300 MHz, DMSO-d$_6$) δ=1.18 (d, 3H), 1.20–1.42 (m, 1H), 1.58–1.73 (m, 1H), 1.81–1.99 (m, 2H), 2.50 (m, 2H), 2.78–2.83 (m, 1H), 5.99 (s, 1H), 7.16 (t, 1H), 7.28 (t, 1H), 7.86 (q, 1H) (characterised as enolate)

EXAMPLE XII 2-(4,5,6,7-Tetrahydro-1H-benzimidazol-2-yl)-1-(2-thienyl)ethanone

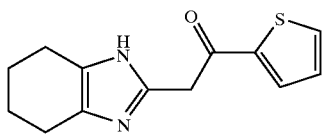

The compound is prepared as described in example X (step 4 and 5) with 3.00 g (21.71 mmol) 2-Methyl-4,5,6,7-tetrahydro-1H-benzimidazole (Helv. Chim. Acta, 1938, 1692), 9.55 g (65.12 mmol) of 2-thiophenecarbonyl chloride and 7.25 g (71.63 mmol) of TEA in 120 ml acetonitrile to yield 9.2 g (63.0% of th.) of (E)-1-(2-Thienyl)-2-[1-(2thienylcarbonyl)-4,5,6,7-tetrahydro-1H-benzimidazol-2-yl]ethenyl 2-thiophenecarboxylate. 3.12 g (6.69 mmol) of (E)-1-(2-Thienyl)-2-[1-(2-thienyl-carbonyl)-4,5,6,7-tetrahydro-1H-benzimidazol-2-yl]ethenyl-2-thiophene-carboxylate is transformed into 2-(4,5,6,7-Tetrahydro-1H-benzimidaz-2-yl)-1-(2-thienyl)ethanone to yield 1.01 g (61.13% of th.).

HPLC (method A): R$_t$=3.52 min
$^1$H-NMR (200 MHz, DMSO-d$_6$) δ=2.30–2.58 (m, 4H), 4.21 (s, 4H), 5.71 (s, 1H), 7.06 (t, 1H), 7.38 (d, 1H), 7.50 (d, 1H), 11.46 (s, 1H) (characterised as enolate)

EXAMPLE XIII 1-(2,4-Difluorophenyl)-2-(4-ethyl-5-methyl-1H-imidazol-2-yl)ethanone

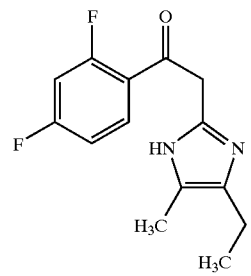

Step 1
4-Ethyl-2,5-dimethyl-1H-imidazole

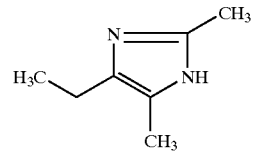

2.00 g (20 mmol) of 2,3-pentandione and 15.42 g (200.0 mmol) of ammoniumacetate are dissolved in 40 ml glacial acid. 3.52 g (80.0 mmol) of acetaldehyde dissolved in 10 ml glacial acid are added dropwise to the cool reaction mixture (icebath). The mixture is stirred for 60 h at rt. The solvent is evaporated under vacuum. The residue is dissolved in 250 ml dichlor-methane and carefully neutralized with 20.0 g (144.0 mmol) potassium carbonate. The solution is stirred for 1 h at rt and then filtrated over potassium carbonate and washed with dichlormethane. The solvent is evaporated under vacuum to yield 4.52 g (90.0% of th.) of 4-Ethyl-2,5-dimethyl-1H-imidazole.

MS (ESIpos): m/z=125.2 (M+H)$^+$
$^1$H-NMR (200 MHz, DMSO-d$_6$) δ=1.05 (t, 3H), 1.98 (s, 3H), 2.10 (s, 3H), 2.37 (q, 2H), 11.10 (s, 1H) 2H), 11.10 (s, 1H)

Step 2
1-(2,4-Difluorophenyl)-2-(4-ethyl-5-methyl-1H-imidazol-2-yl)ethanone

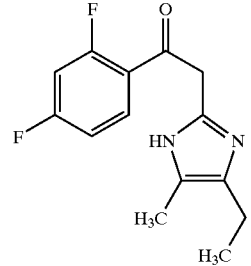

The compound is prepared as described in example X (step 4 and 5) with 1.00 g (8.05 mmol) 4-Ethyl-2,5- dimethyl-1H-imidazole (example XIII, step 1), 4.69 g (26.57 mmol) of 2,4-difluorobenzoyl chloride and 2.85 g (28.18 mmol) of triethylamine in 30 ml acetonitrile. The crude intermediate is directly transformed into 1-(2,4-Difluorophenyl)-2-(4-ethyl-5-methyl-1H-imidazol-2-yl) ethanone to yield 1.69 g (79.4% of th.).

$^1$H-NMR (300 MHz, DMSO-d$_6$) δ=1.14 (t, 3H), 2.11 (s, 3H), 2.42–2.57 (m, 2H), 5.92 (s, 1H), 7.15 (t, 1H), 7.23 (t, 1H), 7.83 (q, 1H) (characterised as enolate)

EXAMPLE XIV 2-(5,6-Dimethyl-4,5,6,7-tetrahydro-1H-benzimidazol-2-yl)-1-(4-fluorophenyl)ethanone

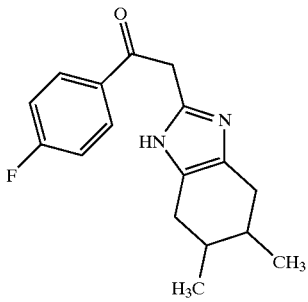

Step 1

2,5,6-Trimethyl-4,5,6,7-tetrahydro-1H-benzimidazole

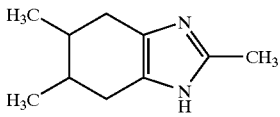

10.0 g (62.41 mmol) 2,5,6-Trimethylbenzimidazole are dissolved in 60 ml glacial acid. 2.0 g (1.89 mmol) palladium (10% on carbon) are added under argon and the reaction mixture is treated with hydrogen at a temperature of 150° C. and 80 bar pressure for 48 h. The solution is filtrated over celite and washed with glacial acid. The solvent is evaporated under vacuum, 10 ml water and sodium hydroxid solution are added the solution to a pH of 9–10. The precipitate is filtrated and washed with water. The precipitate is dissolved in ethyl acetate/dichlor-methane and extracted with saturated sodium chloride solution. The organic phase is dried over sodium sulfate, filtrated and concentrated under vacuum. Diethylether is added, the crystalls are filtrated and dried.

Yield: 3.90 g (38.0% of th.)

HPLC (method A): R=3.49 min.

MS (ESIpos): m/z=165 (M+H)$^+$ $^1$H-NMR (200 MHz, DMSO-d$_6$) δ=0.90 (m, 6H), 1.48 (m, 2H), 1.80–2.20 (m, 6H), 2.40 (d, 1H), 11.12 (s, 1H)

Step 2

2-(5,6-Dimethyl-4,5,6,7-tetrahydro-1H-benzimidazol-2-yl)-1-(4-fluorophenyl)ethanone

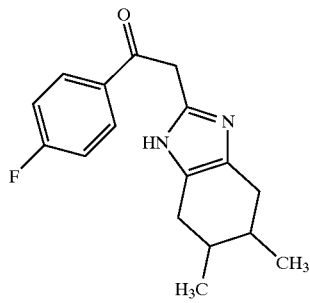

The compound is prepared as described in example X (step 4 and 5) with 1.00 g (6.09 mmol) 2,5,6-Trimethyl-4,5,6,7-tetrahydro-1H-benzimidazole (example XIV, step 1), 3.19 g (20.09 mmol) of 4-fluorobenzoyl chloride and 2.16 g (21.31 mmol) of TEA in 20 ml acetonitrile. The crude intermediate is directly transformed into 2-(5,6-Dimethyl-4,5,6,7-tetrahydro-1H-benzimidazol-2-yl)-1-(4-fluorophenyl)ethanone to yield 776 mg (34.6% of th.).

$^1$H-NMR (200 MHz, DMSO-d$_6$) δ=0.97 (m, 6H), 1.61 (m, 1H), 2.08 (s, 1H), 2.10–2.36 (m, 2H), 2.57–2.78 (m, 2H), 4.84 (s, 2H), 7.16–7.52 (m, 1H), 7.35–7.55 (m, 1H), 7.64–7.83 (m, 1H), 8.05–8.25 (m, 2H)

EXAMPLE XV 1-(2,4-Difluorophenyl)-2-(5,6-dimethyl-4,5,6,7-tetrahydro-1H-benzimidazol-2-yl)ethanone

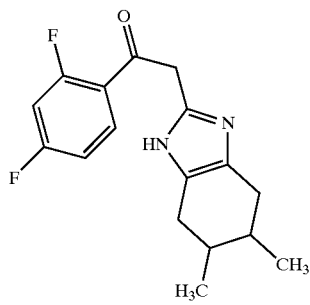

The compound is prepared as described in example X (step 4 and 5) with 1.00 g (6.09 mmol) 2,5,6-Trimethyl-4,5,6,7-tetrahydro-1H-benzimidazole (example XIV, step 1), 3.55 g (20.09 mmol) of 2,4-difluorobenzoyl chloride and 2.16 g (21.31 mmol) of TEA in 20 ml acetonitrile. The crude intermediate is directly transformed into 1-(2,4-Difluorophenyl)-2-(5,6-dimethyl-4,5,6,7-tetrahydro-1H-benzimidazol-2-yl)ethanone to yield 509 mg (23.2% of th.).

$^1$H-NMR (200 MHz, DMSO-d$_6$) δ=0.93 (m, 6H), 1.58 (m, 1H), 1.90–2.05 (m, 1H), 2.14–2.32 (m, 2H), 2.48–2.72 (m, 2H), 5.92 (s, 1H), 7.16 (t, 1H), 7.31 (t, 1H), 7.84 (q, 1H), 8.14 (s, 1H) (characterised as enolate)

EXAMPLE XVI 1-(4-Fluorophenyl)-2-(4-methyl-4,5,6,7-tetrahydro-1H-benzimidazol-2-yl)ethanone hydrochloride

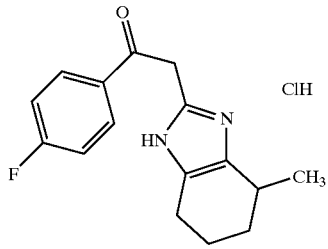

The compound is prepared as described in example X (step 4 and 5) with 1.00 g (6.66 mmol) 2,4-Dimethyl-4,5,6,7-tetrahydro-1H-benzimidazole (example XI, step 1), 3.48 g (21.97 mmol) of 4-fluorobenzoyl chloride and 2.36 g (23.30 mmol) of TEA in 20 ml acetonitrile. The crude intermediate is directly transformed into 1-(4-Fluorophenyl)-2-(4-methyl-4,5,6,7-tetrahydro-1H-benzimidazol-2-yl)ethanone hydrochloride. After the reaction the solvent is evaporated under vacuum. The residue is extracted with ethyl acetate/water. The water phase is concentrated to yield 2.20 g (90.1% of th.).

MS (ESIpos) m/z=273.3 (M+H)$^+$

EXAMPLE XVII 2-(4-Ethyl-5-methyl-1H-imidazol-2-yl)-1-phenylethanone hydrochloride

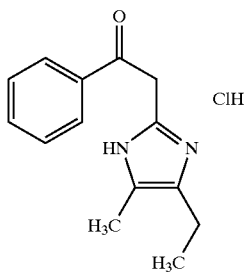

The compound is prepared as described in example X (step 4 and 5) with 1.00 g (8.05 mmol) 4-Ethyl-2,5-dimethyl-1H-imidazole (example XIII, step 1), 3.74 g (26.57 mmol) of benzoyl chloride and 2.85 g (28.18 mmol) of TEA in 20 ml acetonitrile. After reaction the solvent is evaporated under vacuum. The residue is extracted with toluene/water and the water phase is filtrated over a silica-layer. The solvent is evaporated under vacuum. The crude intermediate is directly transformed into 2-(4-Ethyl-5-methyl-1H-imidazol-2-yl)-1-phenylethanone hydrochloride. After the reaction the solvent is evaporated under vacuum. The residue is extracted with ethyl acetate/water. The water phase is concentrated.

LC-MS (method B): R$_t$=1.29 min.

MS (ESIpos) m/z=229.3 (M+H)$^+$

EXAMPLE XVIII 2-(4-Ethyl-5-methyl-1H-imidazol-2-yl)-1-(4-fluorophenyl)ethanone hydrochloride

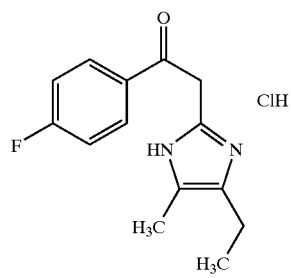

The compound is prepared as described in example XVII with 1.00 g (8.05 mmol) 4-Ethyl-2,5-dimethyl-1H-imidazole (example XIII, step 1), 4.21 g (26.57 mmol) of 4-fluorobenzoyl chloride and 2.85 g (28.18 mmol) of TEA in 20 ml acetonitrile. The crude intermediate is directly transformed into 2-(4-Ethyl-5-methyl-1H-imidazol-2-yl)-1-(4-fluorophenyl)ethanone hydrochloride.

LC-MS (method B): R$_t$=1.31 min.

MS (ESIpos) m/z=247.3(M+H)$^+$

EXAMPLE XIX 2-(4-Methyl-4,5,6,7-tetrahydro-1H-benzimidazol-2-yl)-1-phenylethanone hydrochloride

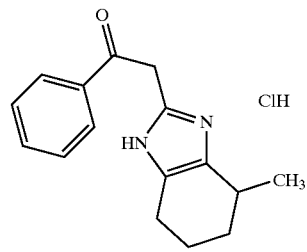

The compound is prepared as described in example XVII with 1.00 g (6.66 mmol) 2,4-Dimethyl-4,5,6,7-tetrahydro-1H-benzimidazole (example XI, step 1), 3.09 g (21.97 mmol) of benzoyl chloride and 2.36 g (23.30 mmol) of TEA in 20 ml acetonitrile.

LC-MS (method B): R$_t$=2.25 min.

MS (ESIpos) m/z=255.3 (M+H)$^+$

EXAMPLE XX 2-(5-Methyl-4-propyl-1H-imidazol-2-yl)-1-phenylethanone hydrochloride

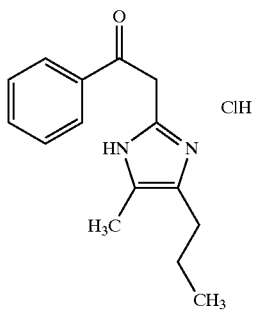

Step 1
2,5-Dimethyl-4-propyl-1H-imidazole

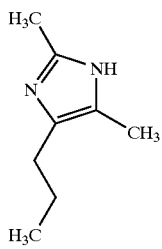

The compound is prepared as described in example XI (step 1) with 5.00 g (39.42 mmol) of 2,3-hexanedione, 45.58 g (0.591 mol) and 6.95 g (0.158 mol) acetaldehyde in 200 ml DMSO. After the extraction the solvent is evaporated under high vacuum. The residue is purified over silica (eluent: petrolether/ethyl acetate 2:1; dichlormethane/methanol/ammonia 9:1:0.05 to 3:1:0.1). The solvent is evaporated under vacuum to yield 3.50 g (64.2% of th.).

MS (Cl$^+$): m/z=139 (M+H)$^+$ $^1$H-NMR (300 MHz, DMSO-d$_6$) δ=0.84 (t, 3H), 1.48 (sex., 2H), 1.97 (s, 3H), 2.14 (s, 3H), 2.31 (t, 2H), 3.17 (s, 1H)

Step 2
2-(5-Methyl-4-propyl-1H-imidazol-2-yl)-1-phenylethanone hydrochloride

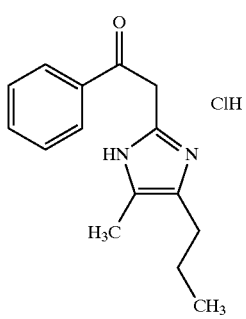

The compound is prepared as described in example XVIII with 1.00 g (7.24 mmol) 2,5-Dimethyl-4-propyl-4H-imidazole (example XX, step 1), 3.36 g (23.88 mmol) of benzoyl chloride and 2.56 g (25.32 mmol) of TEA in 15 ml acetonitrile. The crude intermediate is directly transformed into 2-(5-Methyl-4-propyl-1H-imidazol-2-yl)-1-phenylethanone hydrochloride to yield 1.77 g (64.9% of th.).

$^1$H-NMR (300 MHz, DMSO-d$_6$) δ=0.87 (t, 3H), 1.60 (sex., 2H), 2.21 (s, 3H), 2.56 (t, 2H), 4.88 (s, 2H), 7.60 (t, 2H), 7.74 (t, 1H), 8.06 (d, 2H)

EXAMPLE XXI 2-(4-Butyl-5-methyl-1H-imidazol-2-yl)-1-(2,4-difluorophenyl)ethanone

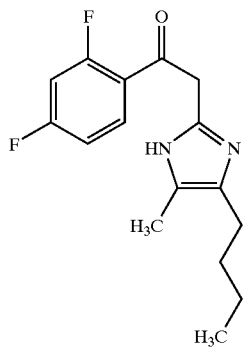

Step 1

4-Butyl-2,5-dimethyl-1H-imidazole

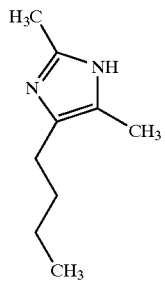

The compound is prepared as described in example XX (step 1) with 5.00 g (39.01 mmol) of 2,3-heptanedione, 45.11 g (0.585 mol) and 6.87 g (0.156 mol) acetaldehyde in 200 ml DMSO. After the extraction the solvent is evaporated under high vacuum. The residue is purified over silica (eluent:dichlormethane/methanol 9:1; dichlormethane/methanol/ammonia 9:1:0.1 to 5:1:0.1). The solvent is evaporated under vacuum to yield 1.70 g (28.6% of th.).

MS (Cl$^+$): m/z=153.1 (M+H)$^+$ $^1$H-NMR (300 MHz, DMSO-d$_6$) δ=0.84 (t, 3H), 1.20 (m, 2H), 1.45 (m, 2H), 1.97 (s, 3H), 2.14 (s, 3H), 2.31 (m, 2H), 11.00 (bs, 1H)

Step 2
2-(4-Butyl-5-methyl-1H-imidazol-2-yl)-1-(2,4-difluorophenyl)ethanone

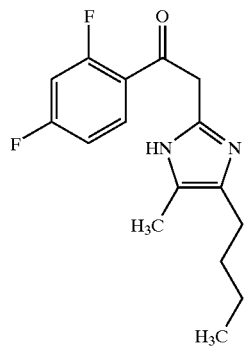

The compound is prepared as described in example X (step 4 and 5) with 0.50 g (3.28 mmol) 4-Butyl-2,5dimethyl-1H-imidazole (example XXI, step 1), 1.91 g (10.84 mmol) of 2,4-difluorbenzoyl chloride and 1.16 g (11.50 mmol) of TEA in 10 ml acetonitrile. The crude intermediate is directly transformed into 2-(4-Butyl-5-methyl-1H-imidazol-2-yl)-1-(2,4-difluorophenyl)ethanone to yield quantitavely the title compound (1.35 g).

$^1$H-NMR (200 MHz, DMSO-d$_6$) δ=0.89 (t, 3H), 1.27 (q, 2H), 1.53 (q, 2H), 2.12 (m, 5H), 5.87 (s, 1H), 7.00–8.10 (m, 4H) (characterised as enolate)

EXAMPLE XXII

2-(4,5-Dimethyl-1H-imidazol-2-yl)-1-(3-methylphenyl)ethanone hydrochloride

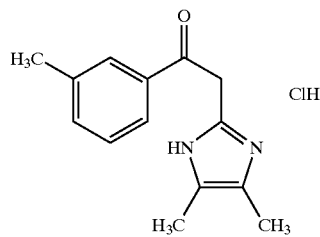

Step 1
2,4,5-Trimethyl-1H-imidazole

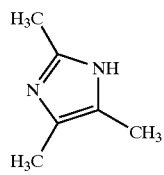

20.0 g (0.232 mol) of biacetyl and 10.22 g (0.232 mol) of acetaldehyde are dissolved in 25 ml ethanol. The solution is cooled to 0° C. At this temperature 50 ml of ammonia (25%) are added dropwise. The mixture is stirred for 20 h at rt. Then the reaction mixture is refluxed for 1 h. After reaction the solvent is evaporated under vacuum. The crude is directly transformed into 2-(4,5-Dimethyl-1H-imidazol-2-yl)-1-(3-methylphenyl)ethanone hydrochloride (example XXII, step 2).

Step 2
2-(4,5-Dimethyl-1H-imidazol-2-yl)-1-(3-methylphenyl)ethanone hydrochloride

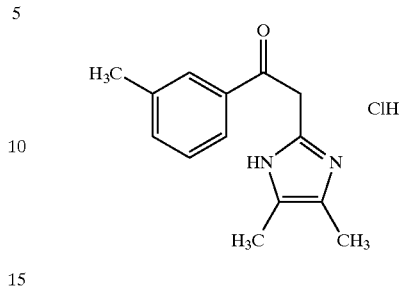

The compound is prepared as described in example XVII with 1.00 g (9.08 mmol) 2,4,5-Trimethyl-1H-imidazole (example XXII, step 1), 4.63 g (29.96 mmol) of 3-methylbenzoyl chloride and 3.22 g (31.77 mmol) of TEA in 20 ml acetonitrile. The crude intermediate is directly transformed into 2-(4,5-Dimethyl-1H-imidazol-2-yl)-1-(3-methylphenyl)ethanone hydrochloride to yield 2.10 g (65.8% of th.).

LC-MS (method C): R$_t$=1.34 min.

MS (ESIpos) m/z=229.2 (M+H)$^+$ $^1$H-NMR (300 MHz, DMSO-d$_6$) δ=2.21 (s, 3H), 2.42 (s, 3H), 2.50 (s, 3H), 4.83 (s, 2H), 7.54 (m, 2H), 7.86 (m, 2H), 13.85 (s, 1H)

EXAMPLE XXIII

1-(2,4-Difluorophenyl)-2-(4,5-dimethyl-1H-imidazol-2-yl)ethanone hydrochloride

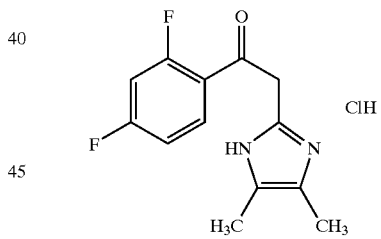

The compound is prepared as described in example XVII with 1.00 g (9.08 mmol) 2,4,5-Trimethyl-1H-imidazole (example XVII, step 1), 5.29 g (29.96 mmol) of 2,4-difluorobenzoyl chloride and 3.22 g (31.77 mmol) of TEA in 20 ml acetonitrile. The crude intermediate is directly transformed into 1-(2,4-Difluorophenyl)-2-(4,5-dimethyl-1H-imidazol-2-yl)ethanone hydrochloride to yield 1.36 g (34.6% of th.).

LC-MS (method C): R$_t$=0.78 min.

MS (ESIpos) m/z=251.2 (M+H)$^+$ $^1$H-NMR (400 MHz, DMSO-d$_6$) δ=2.16 (s, 3H), 2.20 (s, 3H), 4.76 (s, 2H), 7.33 (t, 1H), 7.54 (t, 1H), 8.02 (q, 1H), 13.91 (s, 1H)

EXAMPLE XXIV 2-(5-Methyl-1H-imidazol-2-yl)-1-phenylethanone hydrochloride

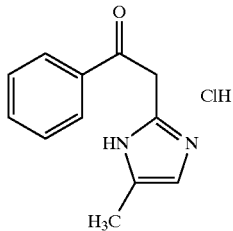

The compound is prepared as described in example XVII with 1.00 g (10.40 mmol) of 2,4-Dimethylimidazole, 4.83 g (34.33 mmol) of benzoyl chloride and 3.68 g (36.41 mmol) of TEA in 20 ml acetonitrile. The crude intermediate is directly transformed into 2-(5-Methyl-1H-imidazol-2-yl)-1-phenylethanone hydrochloride to yield 2.70 g (91.4% of th.).

LC-MS (method C): $R_t$=2.15 min.

MS (ESIpos) m/z=255.2 (M+H)$^+$ $^1$H-NMR (300 MHz, DMSO-d$_6$) δ=2.29 (s, 3H), 4.95 (s, 2H), 7.36 (s, 1H), 7.62 (t, 2H), 7.76 (t, 1H), 8.07 (d, 2H), 14.14 (s, 1H)

EXAMPLE XXV 1-(3-Chlorophenyl)-2-(4,5-dimethyl-1H-imidazol-2-yl)ethanone hydrochloride

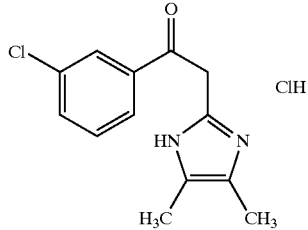

The compound is prepared as described in example XVII with 3.99 g (27.23 mmol) of 2,4,5-Trimethyl-1H-imidazole (example XXII, step 1), 15.73 g (89.87 mmol) of 3-chlorobenzoyl chloride and 13.78 g (136.17 mmol) of TEA in 50 ml acetonitrile. The crude intermediate is directly transformed into 1-(3-Chlorophenyl)-2-(4,5-dimethyl-1H-imidazol-2-yl)ethanone hydrochloride to yield 420 mg (5.4% of th.).

LC-MS (method B): $R_t$=2.09 min.

MS (ESIpos) m/z=249.1(M+H)$^+$ $^1$H-NMR (300 MHz, DMSO-d$_6$) δ=2.19–2.23 (m, 6H), 4.88 (m, 21), 7.66 (t, 1H), 7.83 (dd, 1H), 8.02 (d, 1H), 8.09 (t, 1H), 14.04 (s, 1H)

EXAMPLE XXVI 2-(4-Butyl-5-methyl-1H-imidazol-2-yl)-1-(4-fluorophenyl)ethanone

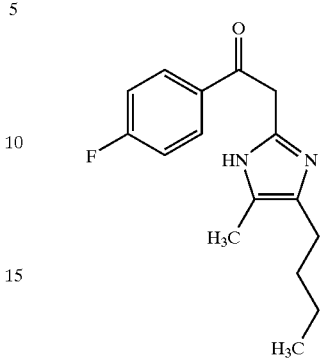

The compound is prepared as described in example X (step 4 and 5) with 500 mg (3.28 mmol) of 2,4-Dimethyl-4,5,6,7-tetrahydro-1H-benzimidazole (example XI, step 1), 1.72 g (10.84 mmol) of 4-fluorobenzoyl chloride and 1.16 g (11.50 mmol) of TEA in 10 ml acetonitrile. The crude intermediate is directly transformed into 2-(4-Butyl-5-methyl-1H-imidazol-2-yl)-1-(4-fluorophenyl)ethanone to yield 698 mg (65.3% of th.).

$^1$H-NMR (200 MHz, DMSO-d$_6$) δ=0.89 (t, 3H), 1.28 (m, 2H), 1.53 (m, 2H), 2.20 (m, 2H), 2.50 (s, 3H), 4.74 (s, 2H), 7.00–8.00 (m, 4H)

EXAMPLE XXVII 2-(4,5-Diethyl-4H-imidazol-2-yl)-1-(4-fluorophenyl)ethanone

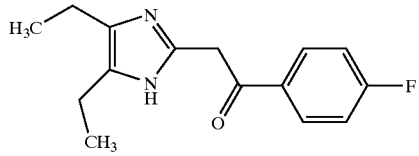

Step 1
4,5-Diethyl-2-methyl-1H-imidazole

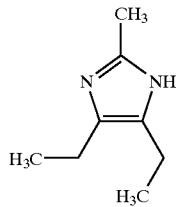

The compound is prepared as described in example XI (step 1) with 5.00 g (43.80 mmol) of 3,4-hexanedione, 50.65 g (0.657 mol) and 7.72 g (0.175 mol) acetaldehyde in 200 ml DMSO. After the extraction the solvent is evaporated under high vacuum. The residue is purified over silica (eluent: dichlormethane/methanol 9:1 to dichlormethane/methanol/ammonia 9:1:0.1 to 5:1:0.1). The solvent is evaporated under vacuum to yield 1.70 g (28.1% of th.).

MS (Cl$^+$): m/z=139 (M+H)$^+$ $^1$H-NMR (200 Mhz, CDCl$_3$) δ=1.18 (t, 6H), 2.33 (s, 3H), 2.54 (q, 4H)

Step 2
2-(4,5-Diethyl-1H-imidazol-2-yl)-1-(4-fluorophenyl)ethanone

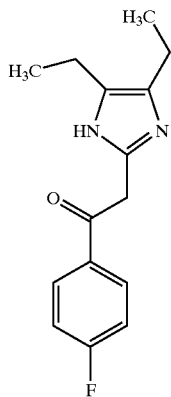

The compound is prepared as described in example X (step 4) with 800 mg (5.79 mmol) of 4,5-Diethyl-2-methyl-1H-imidazole (example XXVII, step 1), 2.75 g (17.36 mmol) of 4-fluorobenzoyl chloride and 1.93 g (19.10 mmol) of TEA in 15 ml acetonitrile. The crude intermediate (1.30 g, 2.58 mmol) is dissolved in 10 ml methanol under argon. 1.12 g (12.88 mmol) of morpholine are added dropwise to the solution. The mixture is refluxed for 10 minutes. The solvent is evaporated under argon and the residue is purified over silica (eluent: dichlormethane/methanol 50:1). The solvent is evaporated under vacuum to yield 572 mg (82.6% of th.).

HPLC (method A): $R_t$=3.95 min.
MS (ESIpos): m/z=261.1 (M+H)$^+$
$^1$H-NMR (300 MHz, DMSO-d$_6$) δ=1.14 (m, 6H), 2.49 (m, 4H), 6.00 (s, 1H), 7.20 (m, 2H), 7.80 (m, 2H)

EXAMPLE XXVIII 2-(4,5-Diethyl-1H-imidazol-2-yl)-1-(2,4-difluorophenyl)ethanone

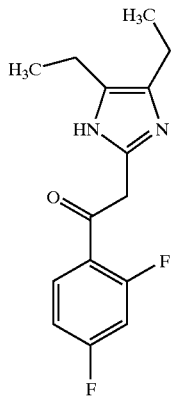

The compound is prepared as described in example XXVII (step 1 and 2) with 800 mg (5.79 mmol) of 4,5-Diethyl-2-methyl-1H-imidazole (example XXVII, step 1), 3.07 g (17.36 mmol) of 2,4-difluorobenzoyl chloride and 1.93 g (19.10 mmol) of TEA in 15 ml acetonitrile. The crude intermediate is directly transformed into 2-(4,5-Diethyl-1H-imidazol-2-yl)-1-(2,4-difluorophenyl)ethanone to yield 478 mg (73.5% of th.).

HPLC (method A): $R_t$=3.81 min.
MS (ESIpos): m/z=279.1 (M+H)$^+$
$^1$H-NMR (500 MHz, DMSO-d$_6$) δ=1.14 (t, 6H), 2.49 (q, 4H), 6.00 (s, 1H), 7.16 (t, 1H), 7.29 (t, 1H), 7.85 (q, 1H) (characterised as enolate)

EXAMPLE XXIX 2-(5-Methyl-4,5,6,7-tetrahydro-1H-benzimidazol-2-yl)-1-phenylethanone

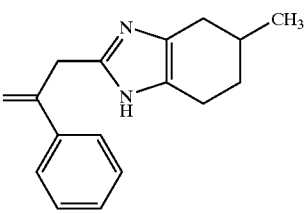

Step 1
2,5-Dimethyl-4,5,6,7-tetrahydro-1H-benzimidazole

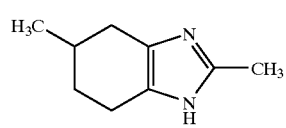

20.0 g (0.137 mol) of 2,5-dimethyl-1H-benzimidazole are dissolved in 150 ml glacial acid and 2.50 g Pt-Mohr catalyst are added under argon. The solution is treated with hydrogen at 80° C. and at 3 bar pressure for 72 h. The solution is filtrated over celite and washed with glacial acid. The solvent is evaporated under vacuum and a few milliliters of water are added to the residue. Sodium hydrogen solution is added to a pH of 12–14. The mixture is extracted with ethyl acetate, the organic phase is extracted with water and dried over sodium sulfate. The ethyl acetate is evaporated under pressure and the residue is dissolved in a little bit of dichlormethane. Diethylether is added and the precipitate is filtrated and washed with diethylether to yield 1.0 g (4.87% of th.).

$^1$H-NMR (400 MHz, CDCl$_3$) δ=1.08 (d, 3H), 1.40 (m, 1H), 1.85 (m, 2H), 2.15 (m, 1H), 2.35 (s, 3H), 2.60 (m, 3H)

Step 2
2-(5-Methyl-4,5,6,7-tetrahydro-1H-benzimidazol-2-yl)-1-phenylethanone

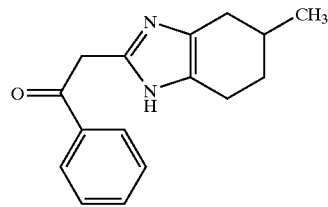

The compound is prepared as described in example XXVII (step 1 and 2) with 1.00 g (6.66 mmol) of 2,5-Dimethyl-4,5,6,7-tetrahydro-1H-benzimidazole (example XXIX, step 1), 3.09 g 21.97 mmol) of benzoyl chloride and 2.36 g (23.30 mmol) of TEA in 20 ml acetonitrile. The crude intermediate is directly transformed into 2-(5-Methyl-4,5,6,7-tetrahydro-1H-benzimidazol-2-yl)-1-phenylethanone to yield 559 mg (22.6% of th.).

MS (ESIpos): m/z=279.1 (M+H)$^+$ $^1$H-NMR (500 MHz, DMSO-d$_6$) δ=1.14 (d, 3H), 1.40 (m, 1H), 1.90 (m, 2H), 2.20 (m, 1), 2.49 (m, 3H), 5.99 (s, 1H), 7.40 (m, 3H), 7.70 (m, 2H) (characterised as enolate)

EXAMPLE XXX 1-(4-Fluorophenyl)-2-(4-isopropyl-1H-imidazol-2-yl)ethanone

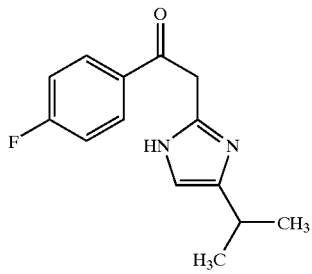

Step 1
1-Bromo-3-methyl-2-butanone

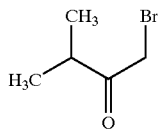

50.0 g (0.581 mol) of 3-Methyl-2-butanone are dissolved in 350 ml methanol and cooled to 0–5° C. 92.77 g (0.851 mol) of bromine are added to the solution at a temperature from 0° C. to max. 10° C. and stirred at this temperature for 1 h. 170 ml water are added to the colourless reaction mixture and stirred for 20 h at rt. 500 ml water are added to the mixture and extracted for three times with 300 ml diethylether. The organic phases are re-extracted with 120 ml potassium carbonate solution (10%) and twice with 120 ml water, dried over calcium chloride for 1 h and filtrated. The solvent is removed under vacuum and the residue is destined under vacuum to yield 59.0 g (61.6% of th.) 1-Bromo-3-methyl-2-butanone.

Bp: 76–84° C./50 mm Hg
$^1$H-NMR (200 MHz, CDCl$_3$) δ=1.17 (d, 6H), 2.99 (m, 1H), 3.99 (s, 2H)

Step 2
4-Isopropyl-2-methyl-1H-imidazole

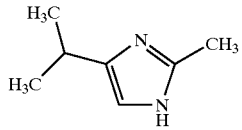

4.42 g (45.00 mmol) of potassium acetate and 4.95 g (30.00 mmol) of 1-Bromo-3-methyl-2-butanone (example XXX, step 1) are dissolved in 45 ml methanol and refluxed for 2 h. The mixture is allowed to cool down to rt. The reaction mixture is filtrated and added to a solution of 11.98 g (60.00 mmol) Copper(II)acetate, 45 ml water in 60 ml ammonia. A solution of 1.65 g (37.50 mmol) of acetaldehyde dissolved in 15 ml water is added to the reaction mixture and all together is refluxed for 5 h. After the reaction the precipitate is filtrated and suspended 37.5 ml glacial acid. A solution of 5.93 g (18.00 mmol) potassium ferrocyanide (II) in 18 ml water is added to the suspension and stirred for 15 minutes, filtrated over silicagel. Sodium hydroxide solution (5 M in water) is added to the filtrate to a pH of 12–14 and is then extracted for 3 times with diethylether. The organic phase is dried and the solvent is evaporated under vacuum to yield 1.37 g (36.8% of th.) of the product.

MS (Cl$^+$): m/z=125.0 (M+H)$^+$
$^1$H-NMR (200 MHz, DMSO-d$_6$) δ=1.13 (d, 6H), 2.19 (s, 3H), 6.46 (d, 1H), 11.30 (s, 1H)

Step 3
1-(4-Fluorophenyl)-2-(4-isopropyl-1H-imidazol-2-yl)ethanone

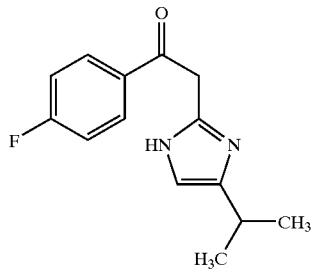

The compound is prepared as described in example XXVII (step 1 and 2) with 450 mg (3.62 mmol) of 4-Isopropyl-2-methyl-1H-imidazole (example XXX, step 1), 1.89 g (11.94 mmol) of 4-fluorobenzoyl chloride and 1.28 g (12.66 mmol) of TEA in 12 ml acetonitrile. The crude intermediate is directly transformed into 1-(4-Fluorophenyl)-2-(4-isopropyl-1H-imidazol-2-yl)ethanone. After extraction the residue is purified over preparative HPLC (RP18-Column, eluent: acetonitrile-water-gradient) to yield 65 mg (7.6% of th.).

LC-MS (method B): R$_t$=1.71 min.
MS (ESIpos) m/z=247.3 (M+H)$^+$

EXAMPLE XXXI 2-(4-Isopropyl-1H-imidazol-2-yl)-1-phenylethanone

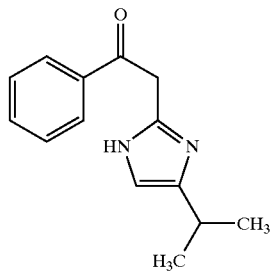

The compound is prepared as described in example XXVII (step 1 and 2) with 500 mg (4.03 mmol) of 4-Isopropyl-2-methyl-1H-imidazole (example XXX, step 2), 1.87 g (13.29 mmol) of benzoyl chloride and 1.43 g (14.09 mmol) of TEA in 12 ml acetonitrile. The crude intermediate is directly transformed into 2-(4-Isopropyl-1H-imidazol-2-yl)-1-phenyl-ethanone. After extraction the residue is purified over preparative HPLC (RP18-Column, eluent: acetonitrile-water-gradient) to yield 105 mg (8.4% of th.).

LC-MS (method B): R$_t$=1.34 min.
MS (ESIpos) m/z=229.2 (M+H)$^+$

EXAMPLE XXXII 2-(4-Bromo-1H-imidazol-2-yl)-1-(4-fluorophenyl)ethanone

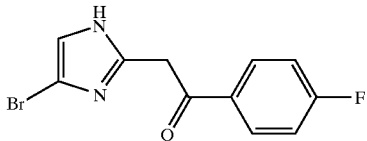

Step 1

4,5-Dibromo-2-methyl-1H-imidazole

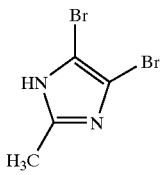

10.0 g (0.122 mol) 2-Methyl-1H-imidazole are dissolved 300 ml trichlormethane and cooled to 0° C. to 5° C. 48.66 g (0.305 mol) of bromine are added dropwise and stirred at rt for 20 h. 250 ml of sodium hydroxide solution (2N) are added dropwise to the cool reaction mixture. Concentrated hydrogen chloride acid is added to the aqueous phase to pH 2. Saturated sodium hydrogen carbonate solution is slowly added to pH 8. The precipitate is filtrated, washed with water and dried to yield 8.4 g (26.0% of th.) 4,5-Dibromo-2-methyl-1H-imidazole.

LC-MS (method D): $R_t$=1.815 min.

MS (ESIpos) m/z=241.0 (M+H)$^+$ $^1$H-NMR (200 MHz, DMSO-d$_6$) δ=2.24 (s, 3H), 12.86 (s, 1H)

Step 2

4-Bromo-2-methyl-1H-imidazole

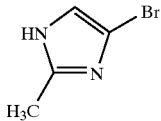

1.50 g (6.25 mmol) of 4,5-Dibromo-2-methyl-1H-imidazole (example XXXII, step 1) are suspended with 7.88 g (62.53 mmol) of sodium sulfite in 60 ml water and 30 ml ethanol. The suspension is refluxed for 18 h. The mixture is extracted with ethyl acetate for three times. The organic phases are dried over sodium sulfate, filtrated and the solvent is evaporated under vacuum. The crude is crystallized with ethyl acetate/hexanes to yield 563 mg (55.9% of th.) 4Bromo-2-methyl-1H-imidazole.

HPLC (method A): $R_t$=0.69 min.

$^1$H-NMR (200 MHz, DMSO-d$_6$) δ=2.23 (s, 3H), 7.08 (s, 1H), 11.92 (s, 1H)

Step 3

2-(4-Bromo-1H-imidazol-2-yl)-1-(4-fluorophenyl)ethanone

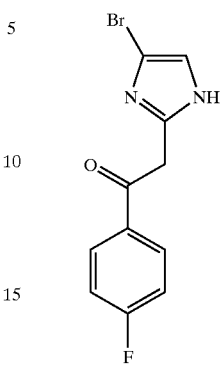

The compound is prepared as described in example XXVII (step 1 and 2) with 1.00 g (6.21 mmol) of 4-Bromo-2-methyl-1H-imidazole (example XXXII, step 2), 2.95 g (18.63 mmol) of 4-fluorobenzoyl chloride and 2.04 g (20.19 mmol) of TEA in 4 ml acetonitrile. The crude intermediate is directly transformed into 2-(4-Bromo-1H-imidazol-2-yl)-1-(4-fluorophenyl)ethanone to yield 711 mg (70.5% of th.).

LC-MS (method B): $R_t$=2.90 min.

MS (ESIpos) m/z=283.0 (M+H)$^+$ $^1$H-NMR (400 MHz, DMSO-d$_6$) δ=4.43 (s, 2H), 7.20 (s, 1H), 7.41 (t, 2H), 8.11 (t, 2H), 12.22 (s, 1H)

EXAMPLE XXXIII 2-(4-Bromo-1H-imidazol-2-yl)-1-phenylethanone

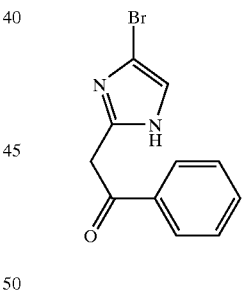

The compound is prepared as described in example XXVII (step 1 and 2) with 500 mg (3.11 mmol) of 4-Bromo-2-methyl-1H-imidazole (example XXXII, step 2), 1.31 g (9.32 mmol) of benzoyl chloride and 1.02 g (10.09 mmol) of TEA in 2 ml acetonitrile. 300 mg of the crude intermediate are directly transformed into 2-(4-Bromo-1H-imidazol-2-yl)-1-phenylethanone to yield 123 mg (73.0% of th.).

LC-MS (method C): $R_t$=2.60 min.

MS (ESIpos) m/z=265.2 (M+H)$^+$ $^1$H-NMR (300 MHz, DMSO-d$_6$) δ=7.19 (s, 1H), 7.39–7.48 (m, 1H), 7.55 (t, 2H), 7.64–7.77 (m, 2H), 8.02 (d, 2H), 12.19 (s, 1H) (characterised as enolate)

EXAMPLE XXXIV 2-(5-Methyl-1H-benzimidazol-2-yl)-1-phenylethanone

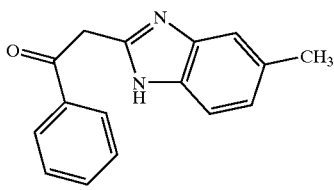

The compound is prepared as described in example XXVII (step 2) with 750 mg (5.13 mmol) of 2,5-Dimethylbenzylimidazole, 2.38 g (16.93 mmol) of benzoyl chloride and 1.82 g (17.99 mmol) of TEA in 10 ml acetonitrile. 1.50 g (3.27 mmol) of the crude intermediate is directly transformed into 2-(5-Methyl-1H-benzimidazol-2-yl)-1-phenylethanone. After reaction the solvent is evaporated under argon and the residue is dissolved in ethyl acetate and extracted with aqueous sodium hydroxide solution (10%) and water. The organic phase is dried over magnesium sulfate, filtrated and washed with ethyl acetate. The solvent is evaporated under vacuum, diethyl ether is added to the residue, the precipitate is filtrated and washed with diethylether to yield 115 mg (14.1% of th.).

LC-MS (method B): $R_t$=2.43 min.

MS (ESIpos) m/z=251.2 (M+H)$^+$ $^1$H-NMR (300 MHz, DMSO-d$_6$) δ=2.40 (s, 3H), 6.05 (s, 1H), 6.98 (d, 1H), 7.18–7.38 (m, 1H), 7.42–7.50 (m, 4H), 7.79–7.87 (m, 2H), 12.14 (s, 1H) (characterised as enolate)

EXAMPLE XXXV 1-(4-Fluorophenyl)-2-(5-methyl-1H-benzimidazol-2-yl)ethanone

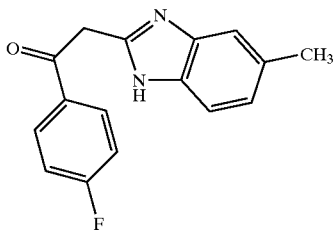

The compound is prepared as described in example XXXIV with 750 mg (5.13 mmol) of 2,5-Dimethylbenzylimidazol, 2.68 g (16.90 mmol) of 4-fluorobenzoyl chloride and 1.82 g (17.99 mmol) of TEA in 10 ml acetonitrile. 1.50 g (3.27 mmol) of the crude intermediate are directly transformed into 1-(4Fluoro-phenyl)-2-(5-methyl-1H-benzimidazol-2-yl)ethanone to yield 98 mg (12.5% of th.).

LC-MS (method B): $R_t$=2.52 min.

MS (ESIpos) m/z=269.3 (M+H)$^+$ $^1$H-NMR (300 MHz, DMSO-d$_6$) δ=2.39 (s, 3H), 5.96 (s, 1H), 6.98 (d, 1H), 7.22–7.43 (m, 4H), 7.89 (q, 2H), 12.14 (s, 1H) (characterised as enolate)

EXAMPLE XXXVI 1-(4-Bromophenyl)-2-(4,5,6,7-tetrahydro-1H-benzimidazol-2-yl)ethanone

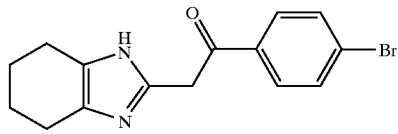

The compound is prepared as described in example XXXIV with 2.00 g (14.68 mmol) 2-methyl-4,5,6,7-tetrahydro-1H-benzimidazole, 9.67 g (44.06 mmol) of 4-bromobenzoyl chloride and 4.90 g (48.42 mmol) of TEA in 50 ml acetonitrile. The crude intermediate is directly transformed into 1-(4-Bromo-phenyl)-2-(4,5,6,7-tetrahydro-1H-benzimidazol-2-yl)ethanone to yield 600 mg (10.7% of th.).

LC-MS (method C): $R_t$=2.39 min.

MS (ESIpos) m/z=320.3 (M+H)$^+$ $^1$H-NMR (300 MHz, DMSO-d$_6$) δ=1.64–1.82 (m, 4H), 2.36–2.57 (m, 4H), 5.99 (s, 1H), 7.58 (d, 2H), 7.67 (d, 2H) (characterised as enolate)

EXAMPLE XXXVII 1-(3,4-Difluorophenyl)-2-(4,5,6,7-tetrahydro-1H-benzimidazol-2-yl)ethanone

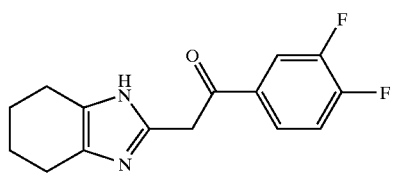

The compound is prepared as described in example XXXIV with 0.40 g (2.94 mmol) of 2-methyl-4,5,6,7-tetrahydro-1H-benzimidazole, 1.56 g (8.84 mmol) of 3,4-difluorobenzoyl chloride and 0.98 g (9.68 mmol) of TEA in 25 ml acetonitrile. The crude intermediate is directly transformed into 1-(3,4-Difluorophenyl)-2-(4,5,6,7-tetrahydro-1H-benzimidazol-2-yl)-ethanone to yield 400 mg (50.4% of th.).

LC-MS (method B): $R_t$=2.24 min.

MS (ESIpos) m/z=277.3 (M+H)$^+$ $^1$H-NMR (300 MHz, DMSO-d$_6$) δ=1.63–1.70 (m, 4H), 2.35–2.53 (m, 4H), 5.95 (s, 1H), 7.43 (q, 1H), 7.51–7.63 (m, 1H), 7.72 (t, 1H) (characterised as enolate)

EXAMPLE XXXVIII 1-(3-Bromophenyl)-2-(4,5,6,7-tetrahydro-1H-benzimidazol-2-yl)ethanone

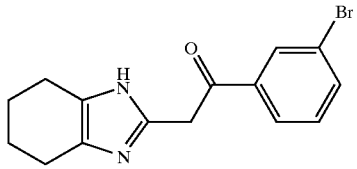

The compound is prepared as described in example XXXIV with 2.00 g (14.68 mmol) of 2-methyl-4,5,6,7-tetrahydro-1H-benzimidazole, 9.67 g (44.06 mmol) of 3-bromobenzoyl chloride and 4.90 g (48.42 mmol) of TEA in 100 ml acetonitrile. The crude intermediate is directly transformed into 1-(3-Bromophenyl)-2-(4,5,6,7-tetrahydro-1H-benzimidazol-2-yl)ethanone to yield 1.32 g (17.0% of th.).

LC-MS (method B): $R_t$=2.49 min.

MS (ESIpos) m/z=319.2 (M+H)$^+$ $^1$H-NMR (300 MHz, DMSO-d$_6$) δ=1.64–1.80 (m, 4H), 2.32–2.54 (m, 4H), 6.00 (s, 1H), 7.36 (t, 1H), 7.53 (d, 1H), 7.72 (d, 1H), 7.86 (s, 1H) (characterised as enolate)

EXAMPLE XXXIX 1-(3-Chlorophenyl)-2-(4,5,6,7-tetrahydro-1H-benzimidazol-2-yl)ethanone

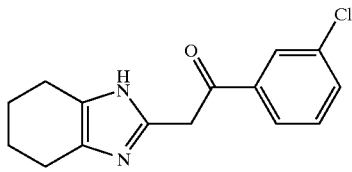

The compound is prepared as described in example XXXIV with 2.00 g (14.68 mmol) of 2-methyl-4,5,6,7-tetrahydro-1H-benzimidazole, 7.71 g (44.05 mmol) of 3-chlorobenzoyl chloride and 4.90 g (48.42 mmol) of TEA in 100 ml acetonitrile. The crude intermediate is directly transformed into 1-(3-Chlorophenyl)-2-(4,5,6,7-tetrahydro-1H-benzimidazol-2-yl)ethanone to yield 8.00 g (93.8% of th.).

LC-MS (method B): $R_t$=2.38 min.

MS (ESIpos) m/z=275.3 (M+H)$^+$

EXAMPLE XXXX 1-(2-Methylphenyl)-2-(4,5,6,7-tetrahydro-1H-benzimidazol-2-yl)ethanone

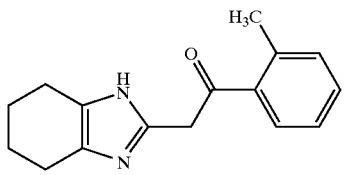

The compound is prepared as described in example XXXIV with 2.00 g (14.68 mmol) of 2-methyl-4,5,6,7-tetrahydro-1H-benzimidazole, 6.81 g (44.05 mmol) of 2-methylbenzoyl chloride and 4.90 g (48.42 mmol) of TEA in 50 ml acetonitrile. The crude intermediate is directly transformed into 1-(2-Methylphenyl)-2-(4,5,6,7-tetrahydro-1H-benzimidazol-2-yl)ethanone to yield 3.20 g (41.3% of th.).

LC-MS (method B): $R_t$=2.33 min.

MS (ESIpos) m/z=255.3 (M+H)$^+$ $^1$H-NMR (300 MHz, DMSO-d$_6$) δ=1.57–1.80 (m, 4H), 2.39 (s, 3H), 2.41–2.60 (m, 4H), 5.44 (s, 1H), 7.16–7.26 (m, 3H), 7.33–7.40 (m, 1H) (characterised as enolate)

EXAMPLE XXXXI 1-(4-Chlorophenyl)-2-(4,5,6,7-tetrahydro-1H-benzimidazol-2-yl)ethanone

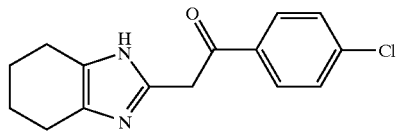

The compound is prepared as described in example XXXIV with 2.00 g (14.68 mmol) of 2-methyl-4,5,6,7-tetrahydro-1H-benzimidazole, 7.71 g (44.05 mmol) of 4-chlorobenzoyl chloride and 4.90 g (48.42 mmol) of TEA in 50 ml acetonitrile. The crude intermediate is directly transformed into 1-(4-Chlorophenyl)-2-(4,5,6,7-tetrahydro-1H-benzimidazol-2-yl)ethanone to yield 71 mg (1.6% of th.).

LC-MS (method C): $R_t$=2.34 min.

MS (ESIpos) m/z=275.2 (M+H)$^+$ $^1$H-NMR (300 MHz, DMSO-d$_6$) δ=1.64–1.82 (m, 4H), 2.36–2.57 (m, 4H), 5.99 (s, 1H), 7.50–8.00 (m, 4H) (characterised as enolate)

EXAMPLE XXXXII 1-(2,5-Difluorophenyl)-2-(4,5,6,7-tetrahydro-1H-benzimidazol-2-yl)ethanone

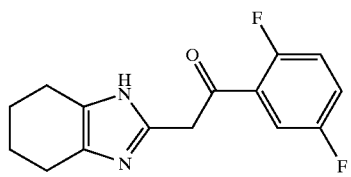

The compound is prepared as described in example XXXIV with 2.00 g (14.68 mmol) of 2-methyl-4,5,6,7-tetrahydro-1H-benzimidazole, 7.78 g (44.07 mmol) of 2,5-difluorobenzoyl chloride and 4.90 g (48.42 mmol) of TEA in 50 ml acetonitrile. The crude intermediate is directly transformed into 1-(2,5-Difluorophenyl)-2-(4,5,6,7-tetrahydro-1H-benzimidazol-2-yl)-ethanone to yield 1.73 g (43.5% of th.).

LC-MS (method C): $R_t$=1.925 min.

MS (ESIpos) m/z=277.1 (M+H)$^+$ $^1$H-NMR (200 MHz, DMSO-d$_6$) δ=1.76 (s, 4H), 2.53 (s, 4H), 6.06 (s, 1H), 7.15–7.34 (m, 2H), 7.51–7.58 (m, 1H) (characterised as enolate)

EXAMPLE XXXXIII 1-(2,4-Difluorophenyl)-2-(4,5,6,7-tetrahydro-1H-benzimidazol-2-yl)ethanone

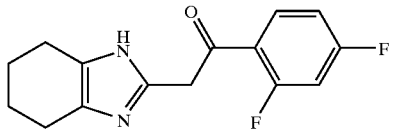

The compound is prepared as described in example XXXIV with 2.00 g (14.68 mmol) 2-methyl-4,5,6,7-tetrahydro-1H-benzimidazole, 7.78 g (44.05 mmol) of 2,4-difluorobenzoyl chloride and 4.90 g (48.42 mmol) of TEA in 50 ml acetonitrile. The crude intermediate is directly transformed into 1-(2,4-Difluorophenyl)-2-(4,5,6,7-tetrahydro-1H-benzimidazol-2-yl)ethanone to yield 225 mg (4.5% of th.).

LC-MS (method B): $R_t$=1.34 min.

MS (ESIpos) m/z=277.1 (M+H)$^+$ $^1$H-NMR (200 MHz, DMSO-$d_6$) δ=1.60–1.81 (m, 4H), 2.37–2.56 (m, 4H), 5.96 (s, 1H), 7.16 (t, 1H), 7.29 (t, 1H), 7.85 (q, 1H) (characterised as enolate)

EXAMPLE XXXXIV 1-(4-Fluorophenyl)-2-(4,5,6,7-tetrahydro-1H-benzimidazol-2-yl)ethanone

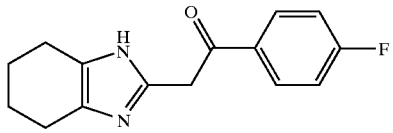

The compound is prepared as described in example XXXXIII with 2.00 g (14.68 mmol) 2-methyl-4,5,6,7-tetrahydro-1H-benzimidazole, 6.98 g (44.05 mmol) of 4-fluorobenzoyl chloride and 4.90 g (48.42 mmol) of TEA in 50 ml acetonitrile. The crude intermediate is directly transformed into 1-(2,4-Difluorophenyl)-2-(4,5,6,7-tetrahydro-1H-benzimidazol-2-yl)-ethanone to yield 737 mg (10.7% of th.).

LC-MS (method B): $R_t$=1.89 min.

MS (ESIpos) m/z=259.2 (M+H)$^+$ $^1$H-NMR (200 MHz, DMSO-$d_6$) δ=1.63–1.84 (m, 4H), 2.32–2.57 (m, 4H), 5.93 (s, 1H), 7.22 (t, 2H), 7.76 (t, 2H) (characterised as enolate)

EXAMPLE XXXXV 1-(2-Chlorophenyl)-2-(4,5,6,7-tetrahydro-1H-benzimidazol-2-yl)ethanone

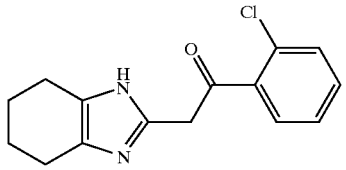

The compound is prepared as described in example XXXXIII with 2.00 g (14.68 mmol) 2-methyl-4,5,6,7-tetrahydro-1H-benzimidazole, 7.71 g (44.05 mmol) 2-chlorobenzoyl chloride and 4.90 g (48.42 mmol) of TEA in 70 ml acetonitrile. The crude intermediate is directly transformed into 1-(2-Chlorophenyl)-2-(4,5,6,7-tetrahydro-1H-benzimidazol-2-yl)ethanone to yield 1.80 g (27.7% of th.).

LC-MS (method C): $R_t$=2.23 min.

MS (ESIpos) m/z=275.2 (M+H)$^+$ $^1$H-NMR (300 MHz, DMSO-$d_6$) δ=1.64–1.82 (m, 4H), 2.36–2.57 (m, 4H), 5.61 (s, 1H), 7.30–7.60 (d, 4H) (characterised as enolate)

EXAMPLE XXXXVI 1-(3-Fluorophenyl)-2-(4,5,6,7-tetrahydro-1H-benzimidazol-2-yl)ethanone hydrochloride

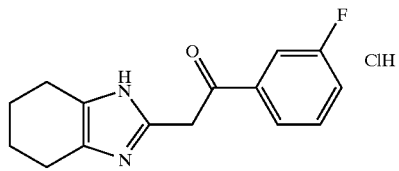

The compound is prepared as described in example XXXXIII with 2.00 g (14.68 mmol) 2-methyl-4,5,6,7-tetrahydro-1H-benzimidazole, 6.98 g (44.05 mmol) of 3-fluorobenzoyl chloride and 4.90 g (48.42 mmol) of TEA in 70 ml acetonitrile. The crude intermediate is directly transformed into 1-(3-Fluorophenyl)-2-(4,5,6,7-tetrahydro-1H-benzimidazol-2-yl)ethanone hydrochloride to yield 0.56 g (9.5% of th.).

LC-MS (method B): $R_t$=1.97 min.

MS (ESIpos) m/z=259.2 (M+H)$^+$ $^1$H-NMR (200 MHz, DMSO-$d_6$) δ=1.80 (s, 4H), 2.60 (s, 4H), 4.93 (s, 2H), 7.30–7.68 (m, 3H), 7.93 (t, 1H), 14.08 (s, 1H)

EXAMPLE XXXXVII 1-(2-Fluorophenyl)-2-(4,5,6,7-tetrahydro-1H-benzimidazol-2-yl)ethanone

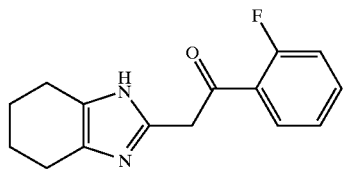

The compound is prepared as described in example XXXXIII with 2.00 g (14.68 mmol) 2-methyl-4,5,6,7-tetrahydro-1H-benzimidazole, 6.98 g (44.05 mmol) of 2-fluorobenzoyl chloride and 4.90 g (48.42 mmol) of TEA in 70 ml acetonitrile.

The crude intermediate is directly transformed into 1-(2-Fluorophenyl)-2-(4,5,6,7-tetrahydro-1H-benzimidazol-2-yl)ethanone to yield 400 mg (10.1% of th.).

LC-MS (method B): $R_t$=1.36 min.

MS (ESIpos) m/z=259.2 (M+H)$^+$

EXAMPLE XXXXVIII 1-(3-Methylphenyl)-2-(4,5,6,7-tetrahydro-1H-benzimidazol-2-yl)ethanone hydrochloride

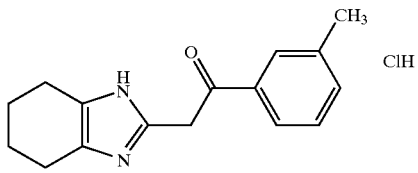

The compound is prepared as described in example XXXXIII with 2.00 g (14.68 mmol) 2-methyl-4,5,6,7-tetrahydro-1H-benzimidazole, 6.81 g (44.05 mmol) of 3-methylbenzoyl chloride and 4.90 g (48.42 mmol) of TEA in 100 ml acetonitrile. The crude intermediate is directly transformed into 1-(3-Methylphenyl)-2-(4,5,6,7-tetrahydro-1H-benzimidazol-2-yl)ethanone hydrochloride to yield 2.0 g (41.5% of th.).

LC-MS (method B): $R_t$=2.23 min.
MS (ESIpos) m/z=253.2 (M+H)$^+$
$^1$H-NMR (200 MHz, DMSO-d$_6$) δ=1.80 (s, 4H), 2.42 (s, 3H), 2.45–2.69 (m, 4H), 4.90 (s, 2H), 6.95–7.60 (m, 3H), 7.87 (d, 1H), 14.12 (s, 1H)

EXAMPLE IL 1-(4-Methylphenyl)-2-(4,5,6,7-tetrahydro-1H-benzimidazol-2-yl)ethanone hydrochloride

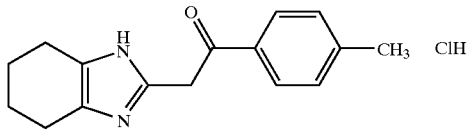

The compound is prepared as described in example XXXXIII with 2.00 g (14.68 mmol) 2-methyl-4,5,6,7-tetrahydro-1H-benzimidazole, 6.81 g (44.05 mmol) of 4-methylbenzoyl chloride and 4.90 g (48.42 mmol) of TEA in 100 ml acetonitrile. The crude intermediate is directly transformed into 1-(4-Methylphenyl)-2-(4,5,6,7-tetrahydro-1H-benzimidazol-2-yl)ethanone hydrochloride to yield 3.90 g (77.4% of th.).

LC-MS (method B): $R_t$=2.18 min.
MS (ESIpos) m/z=255.3 (M+H)$^+$
$^1$H-NMR (200 MHz, CDCl$_3$) δ=1.66 (m, 4H), 2.32 (s, 3H), 2.50 (m, 4H), 4.88 (s, 2H), 7.12 (d, 2H), 7.75 (d, 2H), 13.88 (s, 1H)

EXAMPLE L (3-Bromo-5-chloroimidazo[1,2-a]pyridin-8-yl)(phenyl)methanone

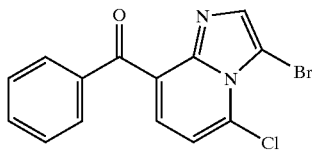

Step 1
2-(1H-Imidazol-2-yl)-1-phenylethanone hydrochloride

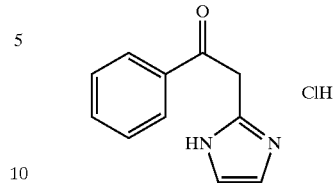

The compound is prepared as described in example XI (step 1 and 2) with 20.00 g (0.244 mol) of 2-Methyl-1H-imidazole, 113.83 g (0.810 mol) of benzoyl chloride and 82.76 g (0.818 mol) of TEA in 580 ml acetonitrile. The crude intermediate is directly transformed into 2-(1H-Imidazol-2-yl)-1-phenylethanone hydrochloride to yield 8.16 g (68.8% of th.).

LC-MS (method B): $R_t$=0.365 min.
MS (ESIpos) m/z=187.2 (M+H)$^+$
$^1$H-NMR (300 MHz, DMSO-d$_6$) δ=4.47 (s, 2H), 7.13 (t, 2H), 7.17 (s, 2H), 7.26 (t, 1H), 7.59 (d, 2H), 13.67 (s, 1H)

Step 2
8-Benzoylimidazo[1,2-a]pyridin-5(1H)-one

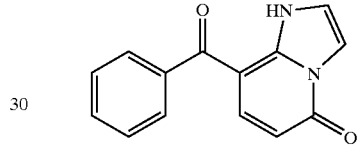

500 mg (2.25 mmol) of 2-(1H-Imidazol-2-yl)-1-phenylethanone hydrochloride (example L, step 1) are suspended in dichlormethane. Sodium hydrogen carbonate is added to the suspension and stirred for 1 h at rt. The suspension is filtrated and the solvent is evaporated under vacuum to yield the free base. The crude is dissolved in 3 ml methanol. 188.78 mg (2.25 mmol) of methyl propiolate are added dropwise to the solution. The mixture is stirred for 24 h at rt. The suspension is filtrated and the precipitate is washed with methanol and diethylether to yield 214 mg (40.0% of th.) 8-Benzoylimidazo[1,2-a]pyridin-5(1H)-one.

LC-MS (method B): $R_t$=2.89 min.
MS (ESIpos) m/z=239.2 (M+H)$^+$
$^1$H-NMR (400 MHz, DMSO-d$_6$) δ=5.80 (d, 1H), 7.51–7.62 (m, 7H), 7.67 (d, 1H), 7.85 (d, 1H), 13.06 (s, 1H)

Step 3
(5-Chloroimidazo[1,2-a]pyridin-8-yl)(phenyl)methanone

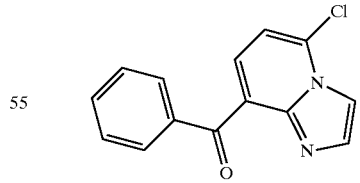

1.0 g (4.20 mmol) of 8-Benzoylimidazo[1,2-a]pyridin-5(1H)-one (example L, step 2) and 20.0 g (130.44 mmol) of phosphoric trichloride are dissolved in 20 ml toluene and refluxed for 1 h. The solvent is evaporated under vacuum; the crude is dissolved in 200 ml ethyl acetate and extracted with 100 ml saturated sodium hydrogen carbonate solution and 100 ml water. The organic phase is dried over magnesium sulfate, filtrated and concentrated. Petrolether is added to the residue and the precipitate is filtrated to yield 943 mg (87.5% of th.) (5-Chloroimidazo[1,2-a]-pyridin-8-yl)(phenyl)methanone.

LC-MS (method C): $R_t$=1.88 min.

MS (ESIpos) m/z=257.1 (M+H)$^+$ $^1$H-NMR (300 MHz, DMSO-d$_6$) δ=7.38 (d, 1H), 7.49–7.58 (m, 3H), 7.66–7.71 (m, 1H), 7.75 (d, 1H), 7.77–7.82 (m, 2H), 8.17 (d, 1H)

Step 4

(3-Bromo-5-chloroimidazo[1,2-a]pyridin-8-yl)(phenyl)methanone

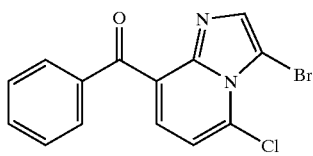

100 mg (0.39 mmol) of (5-Chloroimidazo[1,2-a]pyridin-8-yl)(phenyl)methanone (example L, step 3) are dissolved in 5 ml glacial acid. 30 mg (0.19 mmol) of bromine are added dropwise to the solution. The mixture is stirred for 20 h at rt. The solvent is evaporated under vacuum and the crude is purified over preparative HPLC (RP 18-Column, eluent: acetonitrile-water-gradient) to yield 64 mg (49.0% of th.) (3-Bromo-5-chloroimidazo[1,2-a]pyridin-8-yl)(phenyl)methanone.

HPLC (method A) $R_t$=3.89 min.

MS (Cl$^+$): m/z=337.0 (M+H)$^+$ $^1$H-NMR (300 MHz, DMSO-d$_6$)δ=7.28 (d, 1H), 7.47–7.53 (m, 3H), 7.65–7.70 (m, 2H), 7.77–7.81 (d, 2H)

EXAMPLE LI 1-(4-fluorophenyl)-2-(4-methyl-5-phenyl-1H-imidazol-2-yl)ethanone hydrochloride

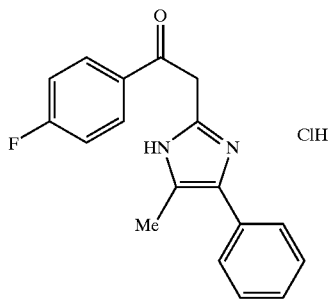

The compound is prepared as described in example XVII with 1.00 g (5.81 mmol) 2,4-dimethyl-5-phenyl-1H-imidazole, 3.04 g (19.2 mmol) of 4-fluorobenzoyl chloride and 2.06 g (20.32 mmol) of TEA in 20 ml acetonitrile. The crude intermediate is directly transformed into 1-(4-fluorophenyl)-2-(4-methyl-5-phenyl-1H-imidazol-2-yl)ethanone hydrochloride to yield 1.16 g (60.4% of th.).

LC-MS (method C): $R_t$=2.34 min.

MS (ESIpos) m/z=295 (M+H−HCl)$^+$

EXAMPLE LII 2-(4,5,6,7-tetrahydro-1H-benzimidazol-2-yl)-1-[3-(trifluoromethyl)phenyl]-ethanone

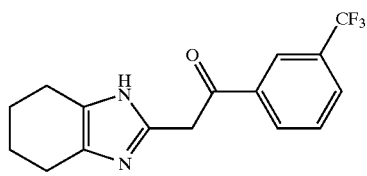

The compound is prepared as described in example XXXXIII with 2.00 g (14.68 mmol) 2-methyl-4,5,6,7-tetrahydro-1H-benzimidazole, 9.19 g (44.05 mmol) of 3-trifluoromethylbenzoyl chloride and 4.90 g (48.42 mmol) of TEA in 70 ml acetonitrile. The crude intermediate is directly transformed into 2-(4,5,6,7-tetrahydro-1H-benzimidazol-2-yl)-1-[3-(trifluoromethyl)phenyl]ethanone to yield 2.34 g (51.5% of th.).

$^1$H-NMR (200 MHz, DMSO-d$_6$) δ=1.63–1.84 (m, 4H), 2.32–2.57 (m, 4H), 6.10 (s, 1H), 7.55–7.80 (m, 2H), 8.00 (m, 2H) (characterised as enolate)

EXAMPLE LIII 1-(4-methoxyphenyl)-2-(4,5,6,7-tetrahydro-1H-benzimidazol-2-yl)ethanone

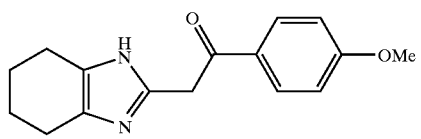

The compound is prepared as described in example XXXXIII with 2.00 g (14.68 mmol) 2-methyl-4,5,6,7-tetrahydro-1H-benzimidazole, 7.51 g (44.05 mmol) of 4-methoxybenzoyl chloride and 4.90 g (48.42 mmol) of TEA in 70 ml acetonitrile. The crude intermediate is directly transformed into 1-(4-methoxyphenyl)-2-(4,5,6,7-tetrahydro-1H-benzimidazol-2-yl)ethanone to yield 1,50 g (37.0% of th.).

LC-MS (method B): $R_t$=2.13 min.

MS (ESIpos) m/z=271 (M+H)$^+$

EXAMPLE LIV 1-(2,4-Difluorophenyl)-2-(5-methyl-4,5,6,7-tetrahydro-1H-benzimidazol-2-yl)ethanone

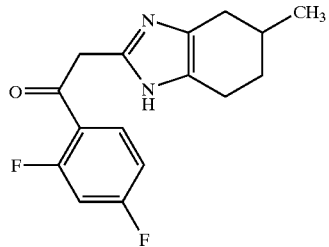

The compound is prepared as described in example XXVII (step 1 and 2) with 0.85 g (5.66 mmol) of 2,5-Dimethyl-4,5,6,7-tetrahydro-1H-benzimidazole (example XXIX, step 1), 3.30 g 18.7 mmol) of 2,4-difluorobenzoyl chloride and 2.00 g (19.80 mmol) of TEA in 20 ml acetonitrile. The crude intermediate is directly transformed into 1-(2,4-Difluorophenyl)-2-(5-methyl-4,5,6,7-tetrahydro-1H-benzimidazol-2-yl)ethanone to yield 947 mg (57.7% of th.).

MS (ESIpos): m/z=279.1 (M+H)$^+$ $^1$H-NMR (500 MHz, DMSO-d$_6$) δ=1.00 (d, 3H), 1.40 (m, 1H), 1.85 (m, 2H), 2.15 (m, 1H), 2.50 (m, 3H), 5.95 (s, 1H), 7.10 (m, 1H), 7.30 (m, 1H), 7.90 (m, 1H) (characterised as enolate)

EXAMPLE LV 2-(4,5-Dimethyl-1H-imidazol-2-yl)-1-(3-methoxyphenyl)ethanone hydrochloride

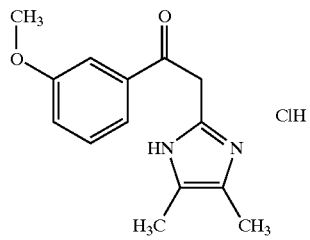

The compound is prepared as described in example VIII with 1.00 g (9.08 mmol) 2,4,5-Trimethyl-1H-imidazole (example XIII, step 1), 5.11 g (29.96 mmol) of 3-methoxybenzoyl chloride and 3.22 g (31.77 mmol) of TEA in 20 ml acetonitrile. The crude intermediate is directly transformed into 2-(4,5-Dimethyl-1H-imidazol-2-yl)-1-(3-methoxyphenyl)ethanone hydrochloride to yield 0.3 g (12% of th.).

LC-MS (method C): R$_t$=1.20 min.

MS (ESIpos) m/z=245 (M+H)$^+$

EXAMPLE LVI 2,3-Dimethyl-8-(3-methoxybenzoyl)imidazo[1,2-a]pyridin-5(1H)-one

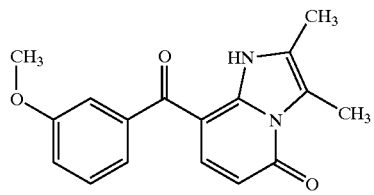

The compound is prepared as described in example 20 with 55 mg (0.02 mmol) of 2-(4,5-Dimethyl-1H-imidazol-2-yl)-1-(3-methoxyphenyl)ethanone hydrochloride (example LV), 250 mg (4.62 mmol) of sodium methylate and 74 mg (0.89 mmol) methyl propiolate.

Yield: 31 mg (52% of th.)

$^1$H-NMR (300 MHz, DMSO-d$_6$): δ=2.29 (s, 3H), 2.62 (s, 3H), 3.80 (s, 3H), 5.64 (d, 1H), 7.10 (m, 3H), 7.43 (m, 1H), 7.51 (d, 1H), 12.73 (s, 1H)

EXAMPLE LVII 8-(3-Hydroxybenzoyl)-2,3-dimethyl dazo[1,2-a]pyridin-5(1H)-one

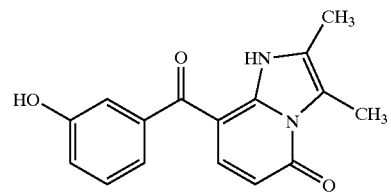

30 mg (0.08 mmol) 2,3-dimethyl-8-(3-methoxybenzoyl)imidazo[1,2-a]pyridin-5(1H)-one are dissolved in 30 mL dichloromethane and cooled to −78° C. 130 mg (0.05 mL, 0.51 mmol) boron tribromide are added and the reaction mixture is slowly warmed to room temperature. After 1 h the mixture is diluted with ethyl acetate and washed twice with water to afford the title compound.

Yield: 20 mg (82% of th.)

$^1$H-NMR (200 MHz, DMSO-d$_6$): δ=2.29 (s, 3H), 2.62 (s, 3H), 5.64 (d, 1H), 6.90 (m, 3H), 7.30 (m, 1H), 7.51 (d, 1H), 9.70 (s, 1H), 12.73 (s, 1H)

PREPARATION EXAMPLES

Example 1

4-Benzoylpyrido[1,2-a]benzimidazol-1(5H)-one

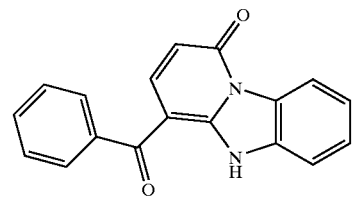

200 mg (0.733 mmol) of the compound of Example II are dissolved in 5 mL ethanol 70 mg (0.833 mmol) sodium bicarbonate and 70 mg (0.833 mmol) methyl propiolate are added at room temperature and the mixture is stirred for 24 h at room temperature. The solvent is evaporated under vacuum and the crude is stirred with ethyl acetate, filtered and dried to yield 77.3 mg (37% of th.) 4-benzoylpyrido[1,2-a]-benzimidazol-1(5H)-one.

$^1$H-NMR (200 MHz, DMSO-d$_6$): δ=5.46 (d, 1H), 7.06 (d t, 1H), 7.25 (d t, 1H), 7.37–7.68 (m, 7H), 8.55 (d, 1H)

Example 2

8-(4-Fluorobenzoyl)-2,3-dimethylimidazo[1,2-a]pyridin-5(1H)-one

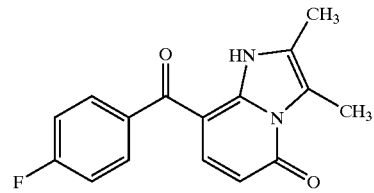

200 mg (0.74 mmol) of the compound of Example IV are dissolved in 2 ml methanol. 45 mg (0.833 mmol) sodium methylate are added at room temperature and the mixture is stirred for 30 min. 62.6 mg (0.74 mmol) methyl propiolate are added and the reaction mixture is stirred for 20 h at room temperature. The solvent is evaporated under vacuum and and the crude is purified over preparative HPLC (RP18-Column, Eluent: Acetonitrile-Water Gradient) to yield 96 mg (45% of th.) 8-(4-fluorbenzoyl)-2,3-dimethylimidazo[1,2-a]pyridin-5(1)-one.

$^1$H-NMR (200 MHz, DMSO-d$_6$): δ=2.3 (s, 3H), 2.62 (s, 3H), 5.65 (d, 1H), 7.28–7.41 (m, 2H), 7.5 (d, 1H), 7.57–7.7 (m, 2H)

Example 3

8-(2-Fluorbenzoyl)-2,3-dimethylimidazo[1,2-a]pyridin-5(1H)-one

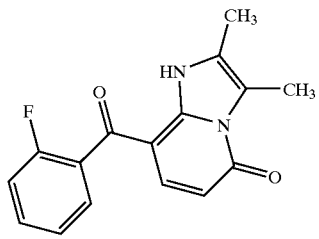

200 mg (0.74 mmol) of the compound of Example VI are dissolved in 2 ml Methanol. 45 mg (0.833 mmol) sodium methylate are added at room temperature and the mixture is stirred for 30 min. 62.6 mg (0.74 mmol) methyl propiolate are added and the reaction mixture is stirred for 20 h at room temperature. The solvent is evaporated under vacuum and the crude is purified over preparative HPLC (RP18-Column, Eluent: Acetonitrile-Water Gradient) to yield 51 mg (24% of th.) 8-(2-Fluorbenzoyl)-2,3-dimethylimidazo[1,2-a]pyridin-5(1)-one.

$^1$H-NMR (200 MHz, DMSO-d$_6$): δ=2.28 (s, 3H), 2.62 (s, 3H) 5.65 (d, 1H), 7.2–7.65 (5H), 12.8 (s, 1H)

Example 4

8-(3-Fluorbenzoyl)-2,3-dimethylimidazo[1,2-a]pyridin-5(1H)-one

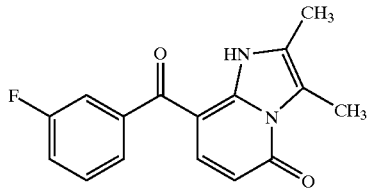

200 mg (0.74 mmol) of the compound of Example VIII are dissolved in 2 ml Methanol. 45 mg (0.833 mmol) sodium methylate are added at room temperature and the mixture is stirred for 30 min. 62.6 mg (0.74 mmol) methyl propiolate are added amd the reaction mixture is stirred for 20 h at room temperature. The solvent is evaporated under vacuum and the crude is purified over preparative HPLC (RP18-Column, Eluent: Acetonitrile-Water Gradient) to yield 74 mg (35% of th.) 8-(3-fluorobenzoyl)-2,3-dimethylimidazo[1,2-a]pyridin-5(1)-one.

$^1$H-NMR (400 MHz, DMSO-d$_6$): δ=2.3 (s, 3H), 2.61 (s, 3H), 5.65 (d, 1H), 7.31–7.6 (m, 5H), 12.72 (s, 1H)

Example 5

4-Benzoyl-6,7,8,9-tetrahydropyrido[1,2-a]benzimidazol-1(5H)-one

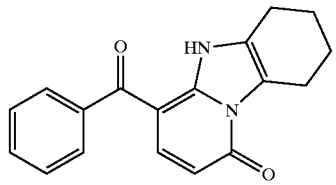

250 mg (0.9 mmol) of the compound of Example IX are dissolved in 2 ml Methanol. 50 mg (0.925 mmol) sodium methylate are added at room temperature and the mixture is stirred for 30 min. 75.9 mg (0.9 mmol) methyl propiolate are added and the reaction mixture is stirred for 20 h at room temperature. The solvent is evaporated under vacuum and the crude is purified over preparative HPLC (RP18-Column, Eluent: Acetonitrile-Water Gradient) to yield 113 mg (43% of th.) 4-benzoyl-6,7,8,9-tetrahydropyrido[1,2-a]benzimidazol-1(5H)-one.

$^1$H-NMR (300 MHz, DMSO-d$_6$): δ=1.78 (m, 4H), 2.67 (m, 2H), 3.18 (m, 2H), 5.65 (d, 1H), 7.45–7.65 (m, 6H), 12.83 (s, 1H)

Example 6

4-(2,4-Difluorobenzoyl)-7,9-dimethyl-6,7,8,9-tetrahydropyrido[1,2-a]benzimidazol-1(5H)-one

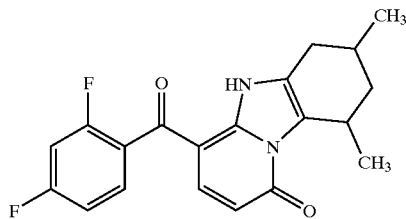

and

Example 7

4-(2,4-Difluorobenzoyl)-6,8-dimethyl-6,7,8,9-tetrahydropyrido[1,2-a]benzimidazol-1(5H)-one

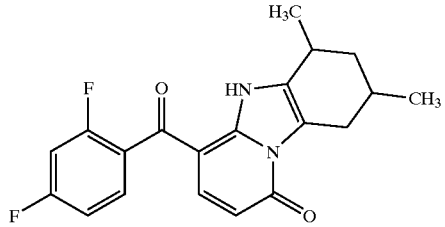

126.8 mg (0.78 mmol) of 1-(1H-imidazol-1-ylcarbonyl)-1H-imidazole and 45.5 mg (0.65 mmol) of propiolic acid are dissolved in 8 ml THF. The mixture is stirred for 3 h at rt. To this solution 131.7 mg (0.43 mmol) of 1-(2,4-Difluorophenyl)-2-(4,6-dimethyl-4,5,6,7-tetrahydro-1H-benzimidazol-2-yl)ethanone (example X) are added and the mixture is stirred for 20 h at rt. The solvent is evaporated under vacuum and the crude is purified over preparative HPLC (RP18-column, eluent: acetonitrile-water-gradient. The isomers are isolated after purification over preparative HPLC (Daicel Chiralpak AD, eluent: iso-hexane-ethanol v/v 30:70):

Example 6-1

1 mg (0.7% of th.) of 4-(2,4-Difluorobenzoyl)-7,9-dimethyl-6,7,8,9-tetrahydropyrido[1,2-a]benzimidazol-1(5H)-one $R_t$=7.93 min (Daicel Chiralpak AD)
$^1$H-NMR (400 MHz, CDCl$_3$): δ=1.15 (d, 3H), 1.45 (d, 3H), 1.50–1.64 (m, 1H), 1.89–2.03 (m, 1H), 2.14–2.23 (m, 1H), 2.24–2.34 (m, 1H), 2.64–2.73 (m, 1H), 3.48–3.60 (m, 1H), 5.88 (d, 1H), 6.88–7.04 (m, 2H), 7.35–7.48 (m, 2H), 11.53 (s, 1H)

Example 6-2

1 mg (0.7% of th.) of 4-(2,4-Difluorobenzoyl)-7,9-dimethyl-6,7,8,9-tetrahydropyrido[1,2-a]berzimidazol-1(5H)-one $R_t$=8.91 min (Daicel Chiralpak AD)
$^1$H-NMR (400 MHz, CDCl$_3$): δ=1.15 (d, 3H), 1.45 (d, 3H), 1.70 (m, 2H), 2.20 (m, 2H), 2.80 (m, 1H), 3.80 (m, 1H), 5.88 (d, 1H), 6.88–7.04 (m, 2H), 7.35–7.48 (m, 2H), 11.53 (s, 1H)

Example 7-1

18 mg (12% of th.) of 4-(2,4-Difluorobenzoyl)-6,8-dimethyl-6,7,8,9-tetrahydropyrido[1,2-a]benzimidazol-1(5H)-one as a single enantiomer.

$R_t$=6.08 min (Daicel Chiralpak AD)
$^1$H-NMR (400 MHz, CDCl$_3$): δ=1.17 (d, 3H), 1.35 (d, 3H), 1.50–1.60 (m, 1H), 1.89–2.07 (m, 2H), 2.63–2.75 (m, 1H), 2.89–3.01 (m, 1H), 3.58–3.70 (m, 1H), 5.87 (d, 1H), 6.88–7.03 (m, 2H), 7.36–7.48 (m, 2H), 11.47 (s, 1H)

Example 7-2

16 mg (10% of th.) of 4-(2,4-Difluorobenzoyl)-6,8-dimethyl-6,7,8,9-tetrahydropyrido[1,2-a]benzimidazol-1(5H)-one as a single enantiomer.

$R_t$=4.83 min (Daicel Chiralpak AD)
$^1$H-NMR (400 MHz, CDCl$_3$): δ=1.17 (d, 3H), 1.35 (d, 3H), 1.46–1.61 (m, 1H), 1.91–2.07 (m, 2H), 2.62–2.75 (m, 1H), 2.89–3.02 (m, 1H), 3.60–3.69 (m, 1H), 5.87 (d, 1H), 6.86–7.06 (m, 2H), 7.35–7.49 (m, 2H), 11.47 (s, 1H)

Example 8

4-(2,4-Difluorobenzoyl)-9-methyl-6,7,8,9-tetrahydropyrido[1,2-a]benzimidazol-1(5H)-one

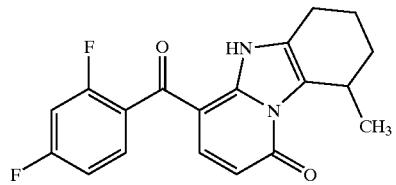

and

Example 9

4-(2,4-Difluorobenzoyl)-6-methyl-6,7,8,9-tetrahydropyrido[1,2-a]benzimidazol-1(5H)-one

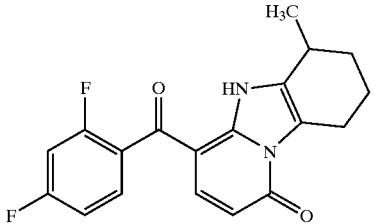

The compounds are prepared as described in example 6 with 500 mg (1.72 mmol) of 1-(2,4-Difluorophenyl)-2-(4-methyl-4,5,6,7-etrahydro-1H-benzimidazol-2-yl)ethanone (example XI), 181 mg (2.58 mmol) of propiolic acid and 503 mg (3.10 mmol) of 1-(1H-imidazol-1-ylcarbonyl)-1H-imidazole. The isomers are isolated after purification over preparative HPLC (Kromasil C18, eluent Water/Acetonitril/Trifluoroacetic acid followed by Daicel Chiralpak AD, eluent: iso-hexane-ethanol v/v 60:40):

Example 8-1

Yield: 7 mg (1.2% of th.) of 4-(2,4-Difluorobenzoyl)-9-methyl-6,7,8,9-tetrahydropyrido[1,2-a]benzimidazol-1(5H)-one as a single enantiomer $R_t$=9.59 min (Daicel Chiralpak AD)
$^1$H-NMR (400 MHz, CDCl$_3$): δ=1.45 (d, 3H), 1.77–2.04 (m, 4H), 2.59–2.76 (m, 2H), 3.79–3.91 (m, 1H), 5.88 (d, 1H), 6.85–7.05 (m, 2H), 7.34–7.49 (m, 2H), 11.51 (s, 1H)

Example 8-2

Yield: 7 mg (1.2% of th.) of 4-(2,4-Difluorobenzoyl)-9-methyl-6,7,8,9-tetrahydropyrido[1,2-a]benzimidazol-1(5H)-one as a single enantiomer $R_t$=12.29 min (Daicel Chiralpak AD)
$^1$H-NMR (400 MHz, CDCl$_3$): δ=1.45 (d, 3H), 1.77–2.04 (m, 4H), 2.59–2.76 (m, 2H), 3.79–3.91 (m, 1H), 5.88 (d, 1H), 6.85–7.05 (m, 2H), 7.34–7.49 (m, 2H), 11.51 (s, 1H)

Example 9-1

Yield: 48 mg (8.4% of th.) of 4-(2,4-Difluorobenzoyl)-6-methyl-6,7,8,9-tetrahydropyrido[1,2-a]benzimidazol-1(5H)-one as a single enantiomer $R_t$=4.95 min (Daicel Chiralpak AD)
$^1$H-NMR (400 MHz, CDCl$_3$): δ=1.35 (d, 3H), 1.46–1.57 (m, 1H), 1.74–1.88 (m, 1H), 1.96–2.11 (m, 2H), 2.88–3.01 (m, 1H), 3.18–3.29 (m, 1H), 3.33–3.44 (m, 1H), 5.86 (d, 1H), 6.89–7.03 (m, 2H), 7.36–7.48 (m, 2H), 11.45 (s, 1H)

Example 9-2

Yield: 43 mg (7.3% of th.) of 4-(2,4-Difluorobenzoyl)-6-methyl-6,7,8,9-tetrahydropyrido[1,2-a]benzimidazol-1(5H)-one as a single enantiomer $R_t$=6.87 min (Daicel Chiralpak AD)
$^1$H-NMR (400 MHz, CDCl$_3$): δ=1.35 (d, 3H), 1.46–1.62 (m, 1H), 1.73–1.88 (m, 1H), 1.95–2.12 (m, 2H), 2.87–3.00

(m, 1H), 3.17–3.45 (m, 2H), 5.87 (d, 1H), 6.85–7.05 (m, 2H), 7.34–7.50 (m, 2H), 11.46 (s, 1H)

Example 10

2-Bromo-8-(4-fluorobenzoyl)imidazo[1,2-a]pyridin-5(1H)-one

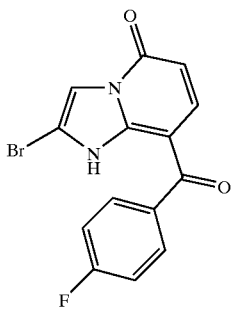

The compound is prepared as described in example 6 with 446.0 mg (1.58 mmol) of 2-(4-bromo-1H-imidazol-2-yl)-1-(4-fluorophenyl)ethanone (example XXXII), 172.43 mg (2.36 mmol) of propiolic acid and 459.82 mg (2.84 mmol) of 1-(1H-imidazol-1-ylcarbonyl)-1H-imidazole.

Yield: 22 mg (4.2% of th.)

LC/MS (method B): $R_t$=3.37 min.

M (ESIpos): m/z=335.5 (M+H)$^+$ $^1$H-NMR (300 MHz, DMSO-d$_6$): δ=5.36 (d, 1H), 7.15–7.29 (m, 2H), 7.42 (d, 1H), 7,48 (s, 1H), 7.52–7.63 (m, 2H)

Example 11

4-(2-Thienylcarbonyl)-6,7,8,9-tetrahydropyrido[1,2-a]benzimidazol-1(5H)-one

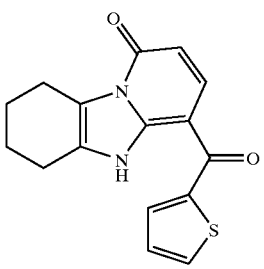

126.2 mg (1.73 mmol) of propiolic acid and 336.6 mg (2.08 mmol) of 1-(1H-imidazol-1-ylcarbonyl)-1H-imidazole are dissolved in 10 ml THF. The mixture is stirred for 3 h at room temperature. To this solution 300 mg (1.15 mmol) of 2-(4,5,6,7-Tetrahydro-1H-benzimidazol-2-yl)-1-(2-thienyl)ethanone (example XII are added and the mixture is refluxed for 24 h. The solvent is evaporated under vacuum and sodium hydrogen carbonate—solution (saturated in water) is added to the crude. The solution is extracted ethyl acetate. The collected organic phases are reextracted with brine—solution an dried over sodium sulfate. The solvent is evaporated under vacuum and the crude is purified over preparative HPLC (RP18-Column, Eluent: acetonitrile-Water Gradient) to yield 150 mg (43.6% of th.) 4-(2-Thienylcarbonyl)-6,7,8,9-tetrahydropyrido[1,2-a]benzimidazol-1(5H)-one.

$^1$H-NMR (200 MHz, DMSO-d$_6$): δ=1.69–1.87 (m, 4H), 2.60–2.72 (m, 2H), 3.11–3.24 (m, 2H), 5.73 (d, 1H), 7.24 (t, 1H), 7.71 (d, 1H), 7.92 (d, 1H), 12.79 (d, 1H), 12.75 (s, 1H)

Example 12

2,3-Diethyl-8-(4-fluorobenzoyl)imidazo[1,2-a]pyridin-5(1H)-one

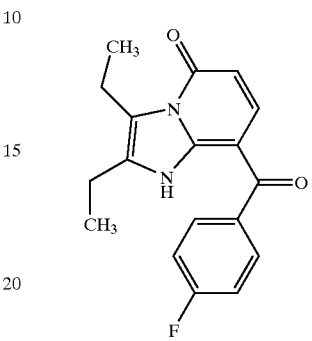

The compound is prepared as described in example 6 with 122.1 mg (1.67 mmol) of propiolic acid, 325.6 mg (2.01 mmol) of 1-(1H-imidazol-1-ylcarbonyl)-1H-imidazole and 300 mg (1.12 mmol) of 2-(4,5-Diethyl-1H-imidazol-2-yl)-1-(4-fluorophenyl)ethanone (example XXVII).

Yield: 157 mg (45.1% of th.)

$^1$H-NMR (400 MHz, DMSO-d$_6$): δ=1.16–1.24 (m, 6H), 2.74 (q, 2H), 3.09 (q, 2H), 5.69 (d, 1H), 7.31–7.39 (m, 2H), 7.52 (d, 1H), 7.63–7.69 (m, 2H), 12.75 (s, 1H)

Example 13

8-(2,4-Difluorobenzoyl)-2,3-diethylimidazo[1,2-a]pyridin-5(1H)-one

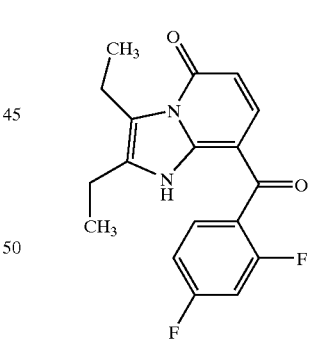

The compound is prepared as described in example 6 with 98.3 mg (1.35 mmol) of propiolic acid, 262.2 mg (1.62 mmol) of 1-(1H-imidazol-1-ylcarbonyl)-1H-imidazole and 250 mg (0.90 mmol) of 2-(4,5-Diethyl-1H-imidazol-2-yl)-1-(2,4-difluorophenyl)ethanone (example XXVII).

Yield: 106 mg (35.7% of th.).

$^1$H-NMR (400 MHz, DMSO-d$_6$): δ=1.20 (t, 6H), 2.74 (q, 2H), 3.08 (q, 2H), 5.69 (d, 1H), 7.19–7.26 (m, 1H), 7.28–7.34 (m, 1H), 7.36–7.44 (m, 1H), 7.51–7.59 (m, 1H), 12.81 (s, 1H)

Example 14

8-Benzoyl-2-bromoimidazo[1,2-a]pyridin-5(1H)-one

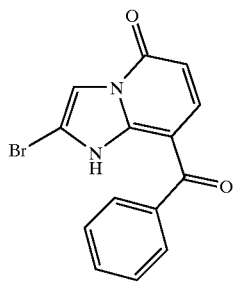

The compound is prepared as described in example 6 with 96.50 mg (0.36 mmol) of 2-(4-bromo-1H-imidazol-2-yl)-1-phenylethanone (example XXXXIII), 39.84 mg (0.55 mmol) of propiolic acid and 106.24 mg (0.66 mmol) of 1-(1H-imidazol-1-ylcarbonyl)-1H-imidazole.

Yield: 13 mg (10.5% of th.)
LC/MS (method D): $R_t$=3.19 min
M (ESIpos): m/z=317.0 (M+H)$^+$
$^1$H-NMR (200 MHz, DMSO-d$_6$): δ=5.34 (d, 1H), 7.28–7.57 (m, 7H)

Example 15

8-(2,4-Difluorobenzoyl)-3-ethyl-2-methylimidazo[1,2-a]pyridin-5(1H)-one

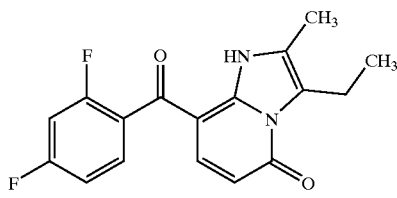

and

Example 16

8-(2,4-Difluorobenzoyl)-2-ethyl-3-methylimidazo[1,2-a]pyridin-5(1H)-one

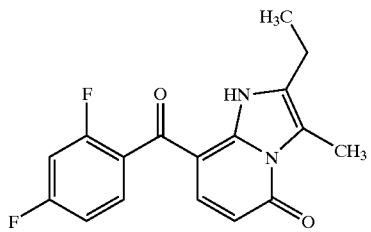

552 mg (3.40 mmol) of 1-(1H-imidazol-1-ylcarbonyl)-1H-imidazole and 199 mg (2.83 mmol) of propiolic acid are dissolved in 25 ml THF. The mixture is stirred for 3 h at rt. To this solution are added 500 mg (1.89 mmol) of 1-(2,4-Difluorophenyl)-2-(4-ethyl-5-methyl-1H-imidazol-2-yl)ethanone (example XIII) and the mixture is refluxed for 24 h. The solvent is evaporated under vacuum and the crude is purified over preparative HPLC (RP18-Column, Eluent: acetonitrile-water-gradient). The regioisomers are isolated after purification over preparative HPLC (Daicel Chiralpak AD, eluent: iso-hexane-ethanol v/v 60:40).

Example 10

Yield: 79 mg (13% of th.) 8-(2,4-Difluorobenzoyl)-3-ethyl-2-methylimidazo[1,2-a]pyridin-5(1H)-one $R_t$=12.62 min (Daicel Chiralpak AD)

$^1$H-NMR (400 MHz, DMSO-d$_6$): δ=1.17 (t, 3H), 2.32 (s, 3H), 3.07 (q, 2H), 5.69 (d, 1H), 7.23 (t, 1H), 7.31 (d, 1H), 7.40 (t, 1H), 7.54 (q, 1H), 12.84 (s, 1H)

Example 16

Yield: 179 mg (30% of th.) 8-(2,4-Difluorobenzoyl)-2-ethyl-3-methylimidazo[1,2-a]pyridin-5(1H)-one $R_t$=5.90 min (Daicel Chiralpak AD)

$^1$H-NMR (400 MHz, DMSO-d$_6$): δ=1.17 (t, 3H), 2.63 (s, 3H), 2.72 (q, 2H), 5.65 (d, 1H), 7.19–7.32 (m, 2H), 7.35–7.44 (m, 1H), 7.50–7.59 (m, 1H), 12.78 (s, 1H)

Example 17

4-(4-Fluorobenzoyl)-7,8-dimethyl-6,7,8,9-tetrahydropyrido[1,2-a]benzimidazol-1(5H)one

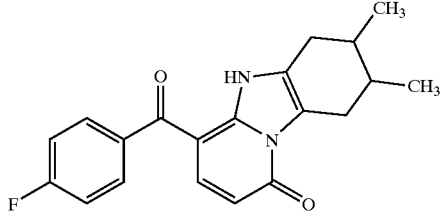

The compounds are prepared as described in example 10 with 200 mg (0.70 mmol) of 2-(5,6-Dimethyl-4,5,6,7-tetrahydro-1H-benzimidazol-2-yl)-1-(4-fluorophenyl)ethanone (example XIV), 73.3 mg (1.05 mmol) of propiolic acid and 204 mg (1.26 mmol) of 1-(1H-imidazol-1-ylcarbonyl)-1H-imidazole.

Example 17-1

Yield: 9.9 mg (4.1% of th.)

$^1$H-NMR (400 MHz, CDCl$_3$): δ=0.96–1.09 (m, 6H), 2.01–2.19 (m, 2H), 2.34–2.48 (m, 1H), 2.72–2.85 (m, 1H), 2.97–3.14 (m, 1H), 3.36–3.50 (m, 1H), 5.87 (d, 1H), 7.08–7.23 (m, 2H), 7.54–7.69 (m, 3H), 11.47 (s, 1H)

Example 17-2

Yield: 30 mg (12.7% of th.)

$^1$H-NMR (300 MHz, CDCl$_3$): δ=1.05–1.19 (m, 6H), 1.62–1.80 (m, 2H), 2.28–2.42 (m, 1H), 2.71–2.96 (m, 2H), 3.52–3.66 (m, 1H), 5.87 (d, 1H), 7.10–7.22 (m, 2H), 7.54–7.69 (, 3H), 11.45 (s, 1H)

Example 18

4-(2,4-Difluorobenzoyl)-7,8-dimethyl-6,7,8,9-tetrahydropyrido[1,2-a]benzimidazol-1(5H)-one

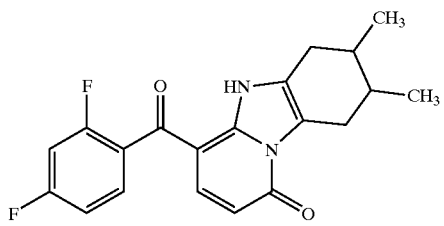

The compounds are prepared as described in example 15 with 200 mg (0.66 mmol) of 1-(2,4-Difluorophenyl)-2-(5,6-dimethyl-4,5,6,7-tetrahydro-1H-benzimidazol-2-yl)ethanone (example XV), 69 mg (0.99 mmol) of propiolic acid and 192 mg (1.18 mmol) of 1-(1H-imidazol-1-ylcarbonyl)-1H-imidazole.

EXAMPLE 18-1

Yield: 19.3 mg (8% of th.)

$^1$H-NMR (300 MHz, CDCl$_3$): δ=0.95–1.09 (m, 6H), 2.05–2.19 (m, 2H), 2.35–2.50 (m, 1H), 2.72–2.86 (m, 1H), 2.97–3.11 (m, 1H), 3.34–3.48 (m, 1H), 5.86 (d, 1H), 6.85–7.06 (m, 2H), 7.33–7.51 (m, 2H), 11.40 (s, 1H)

Example 18-2

Yield: 37 mg (16% of th.)

$^1$H-NMR (400 MHz, CDCl$_3$): δ=1.07–1.18 (m, 6H), 1.61–1.80 (m, 2H), 2.28–2.4103 (m, 1H), 2.72–2.94 (m, 2H), 3.51–3.64 (m, 1H), 5.86 (d, 1H), 6.86–7.03 (m, 2H), 7.34–7.48 (m, 2H), 11.40 (s, 1H)

Example 19

3-Butyl-8-(2,4-difluorobenzoyl)-2-methylimidazo[1,2-a]pyridin-5(1H)-one

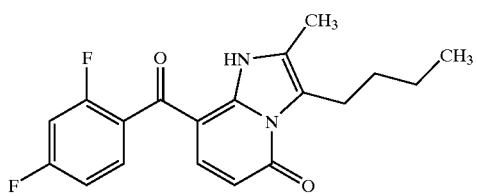

and

Example 20

2-Butyl-8-(2,4-difluorobenzoyl)-3-methylimidazo[1,2-a]pyridin-5(1H)-one

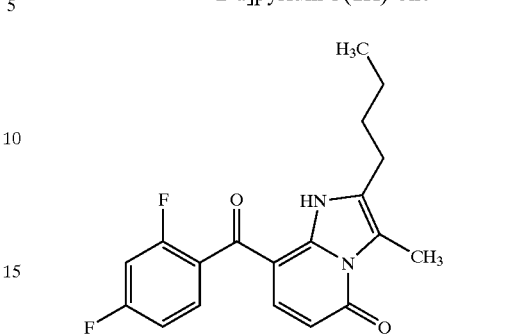

The compounds are prepared as described in example 10 with 200 mg (0.68 mmol) of 2-(4-Butyl-5-methyl-1H-imidazol-2-yl)-1-(2,4-difluorophenyl)ethanone (example XXI), 72 mg (1.03 mmol) of propiolic acid and 200 mg (1.23 mmol) of 1-(1H-imidazol-1yl-carbonyl)-1H-imidazole. The following compounds are obtained:

Example 19

Yield: 18 mg (8% of th.) of 3-Butyl-8-(2,4-difluorobenzoyl)-2-methylimidazo[1,2-a]pyridin-5(1H)-one $^1$H-NMR (300 MHz, CDCl$_3$): δ=0.95 (t, 3H), 1.32–1.44 (m, 2H), 1.63–1.75 (m, 2H), 2.33 (s, 1H), 3.08–3.18 (t, 2H), 5.86 (d, 1H), 6.86–7.05 (m, 2H), 7.34–7.49 (m, 2H), 11.50 (s, 1H)

Example 20

Yield: 65 mg (27.6% of th.) of 2-Butyl-8-(2,4-difluorobenzoyl)-3-methylimidazo[1,2-a]pyridin-5(1H)-one $^1$H-NMR (300 MHz, CDCl$_3$): δ=0.98 (t, 3H), 1.35–1.52 (m, 2H), 1.60–1.73 (m, 2H), 2.66 (t, 2H), 2.74 (s, 3H), 5.85 (d, 1H), 6.87–7.04 (m, 2H), 7.33–7.49 (m, 2H), 11.44 (s, 1H)

Example 21

3-Butyl-8-(4-fluorobenzoyl)-2-methylimidazo[1,2-a]pyridin-5(1H)-one

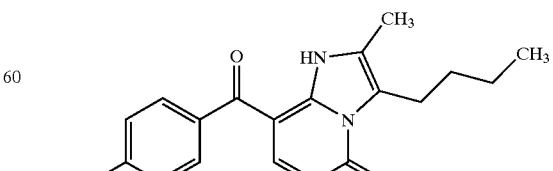

and

Example 22

2-Butyl-8-(4-fluorobenzoyl)-3-methylimidazo[1,2-a]pyridin-5(1H)-one

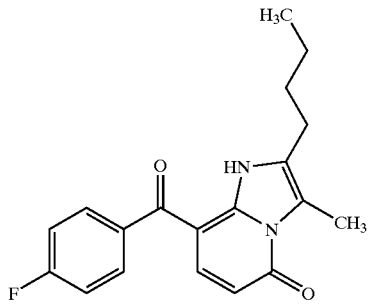

The compounds are prepared as described in example 10 with 200 mg (0.73 mmol) of 2-(4-butyl-5-methyl-1H-imidazo-2-yl)-1-(4-fluorophenyl)ethanone (example XXVI), 77 mg (1.09 mmol) of propiolic acid and 212 mg (1.31 mmol) of 1-(1H-imidazol-1-ylcarbonyl)-1H-imidazole.

Example 21

Yield: 25 mg (11% of th.) of 3-Butyl-8-(4-fluorobenzoyl)-2-methylimidazo[1,2-a]pyridin-5(1H)-one $^1$H-NMR (300 MHz, CDCl$_3$): δ=0.95 (t, 3H), 1.34–1.47 (m, 2H), 1.63–1.83 (m, 2H), 2.33 (s, 1H), 3.14–3.18 (t, 2H), 5.87 (d, 1H), 7.11–7.21 (m, 2H), 7.56–7.67 (m, 3H), 11.58 (s, 1H)

Example 22

Yield: 78 mg (33% of th.) of 2-Butyl-8-(4-fluorobenzoyl)-3-methylimidazo[1,2-a]pyridin-5(1H)-one $^1$H-NMR (300 MHz, CDCl$_3$): δ=0.97 (t, 3H), 1.34–1.49 (m, 2H), 1.61–1.73 (m, 2H), 2.66 (t, 2H), 2.75 (s, 3H), 5.85 (d, 1H), 7.12–7.21 (m, 2H), 7.56–7.67 (m, 3H), 11.52 (s, 1H)

Example 23

8-(4-Fluorobenzoyl)-2-isopropylimidazo[1,2-a]pyridin-5(1H)-one

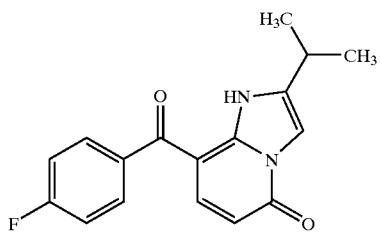

The compound is prepared as described in example 10 with 65 mg (0.26 mmol) of 1-(4-fluorophenyl)-2-(4-isopropyl-1H-imidazol-2-yl)ethanone (example XXX), 27.7 mg (0.40 mmol) of propiolic acid and 77 mg (0.48 mmol) of 1-(1H-imidazol-1-yl-carbonyl)-1H-imidazole.

Yield: 19 mg (25.5% of th.)

$^1$H-NMR (300 MHz, DMSO-d$_6$): δ=1.31 (d, 6H), 3.15–3.24 (m, 1H), 5.80 (d, 1H), 7.31–7.41 (m, 2H), 7.57–7.73 (m, 4H), 12.92 (s, 1H)

Example 24

8-Benzoyl-2-isopropylimidazo[1,2-a]pyridin-5(1H)-one

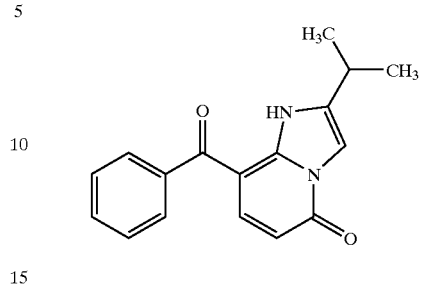

The compound is prepared as described in example 15 with 105 mg (0.46 mmol) of 2-(4-isopropyl-1H-imidazol-2-yl)-1-phenylethanone (example X, 48.3 mg (0.69 mmol) of propiolic acid and 134 mg (0.83 mmol) of 1-(1H-imidazol-1-yl-carbonyl)-1H-imidazole.

Yield: 35 mg (27% of th.)

$^1$H-NMR (300 MHz, DMSO-d$_6$): δ=1.32 (d, 6H), 3.15–3.27 (m, 1H), 5.80 (d, 1H), 7.49–7.68 (m, 7H), 12.92 (s, 1H)

Example 25

4-Benzoyl-8-methyl-6,7,8,9-tetrahydropyrido[1,2-a]benzimidazol-1(5H)-one

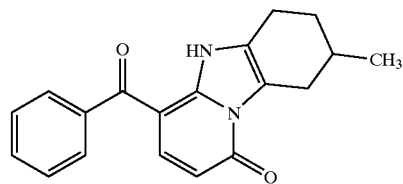

and

Example 26

4-Benzoyl-7-methyl-6,7,8,9-tetrahydropyirido[1,2-a]benzimidazol-1(5H1)-one

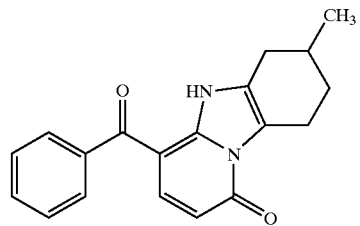

100 mg (0.39 mmol) of 2-(5-Methyl-4,5,6,7-tetrahydro-1H-benzimidazol-2-yl)-1-phenylethanone (example XXIX are dissolved in 1 ml methanol. 20 mg (0.37 mmol) sodium methylate are added and the mixture is stirred for 30 min at rt. 33.1 mg (0.39 mmol) methyl propiolate are added and the reaction mixture is stirred for 20 h at rt. The solvent is evaporated under vacuum and the crude is purified over preparative HPLC (RP18-Column, eluent: acetonitrile-water-gradient). The isomers are isolated after purification over preparative HPLC (Daicel Chiralpak AD, eluent: iso-hexane-ethanol v/v 60:40):

Example 25-1

Yield: 17 mg (14% of th.) of (−)-4-Benzoyl-8-methyl-6,7,8,9-tetrahydropyrido[1,2-a]benzimidazol-1(5H)-one $[\alpha]_D = -48.1°$
LC-MS (B): $R_t = 4.02$ min
M (ESIpos): m/z=307.4 (M+H)$^+$

Example 25-2

Yield: 14 mg (12% of th.) of (+)-4-Benzoyl-8-methyl-6,7,8,9-tetrahydropyrido[1,2-a]benzimidazol-1(5H)-one $[\alpha]_D = +62.3°$
LC-MS (B): $R_t = 4.01$ min
M (ESIpos): m/z=307.4 (M+H)$^+$

Example 26-1

Yield: 13 mg (11% of th.) of (+)-4-Benzoyl-7-methyl-6,7,8,9-tetrahydropyrido[1,2-a]benzimidazol-1(5H)-one $^1$H-NMR (200 MHz, CDCl$_3$): δ=1.15 (d, 3H), 1.20–1.35 (m, 1H) 1.90–2.13 (m, 2H), 2.21–2.41 (m, 1H), 2.68–2.85 (m, 1H), 3.07–3.31 (m, 1H)), 3.44–3.63 (m, 1H), 5.86 (d, 1H), 7.40–7.70 (m, 6H), 11.49 (s, 1H)
$[\alpha]_D = +63.8°$
LC-MS (B): $R_t = 4.02$ min
M (ESIpos): m/z=307.4 (M+H)$^+$

Example 26-2

Yield: 13 mg (11% of th.) of (−)-4-Benzoyl-7-methyl-6,7,8,9-tetrahydropyrido[1,2-a]benzimidazol-1(5H)-one $[\alpha]_D = -70.5°$
LC-MS (13): $R_t = 4.02$ min
M (ESIpos): m/z=307.4 (M+H)$^+$

Example 27

4-(4-Fluorobenzoyl)-6-methyl-6,7,8,9-tetrahydropyrido[1,2-a]benzimidazol-1(5H)-one

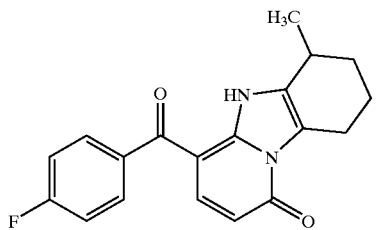

The compound is prepared as described in example 20 with 200 mg (0.65 mmol) of 1-(4-fluorophenyl)-2-(4-methyl-4,5,6,7-tetrahydro-1H-benzimidazol-2-yl)ethanone hydrochloride (example XVI), 50 mg (0.93 mmol) of sodium methylate and 54.4 mg (0.65 mmol) methyl propiolate.

Yield: 15 mg (7.1% of th.)
$^1$H-NMR (400 MHz, DMSO-d$_6$): δ=1.29 (d, 3H), 1.49–1.57 (m, 1H), 1.70–1.94 (m, 3H), 2.94–3.03 (m, 1H), 3.05–3.15 (m, 1H), 3.20–3.29 (m, 1H), 5.65 (d, 1H), 7.30–7.38 (m, 2H), 7.52 (d, 1H), 7.61–7.68 (m, 2H)

Example 28

4-Benzoyl-8-methylpyrido[1,2-a]benzimidazol-1(5H)-one and 4-benzoyl-7-methylpyrido[1,2-a]benzimidazol-1(5H)-one

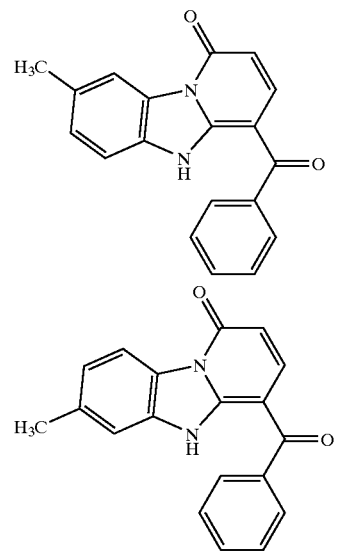

The compounds are prepared as described in example 20 with 90 mg (0.36 mmol) of 2-(5-Methyl-1H-benzimidazol-2-yl)-1-phenylethanone (example XXXIV), 38.9 mg (0.72 mmol) of sodium methylate and 30.2 mg (0.36 mmol) methyl propiolate; a mixture of regioisomers is obtained.

Yield: 30.1 mg (27.7% of th.)

$^1$H-NMR (300 MHz, DMSO-d$_6$): δ=2.5 (s, 3H), 5.95–6.01 (m, 1H), 7.24–7.44 (m, 1H), 7.51–7.79 (m, 7H), 8.51–8.58 (m, 1H), 13.29 (s, 1H)

Example 29

4-(4-Fluorobenzoyl)-8-methylpyrido[1,2-a]benzimidazol-1(5H)-one and 4-(4-fluorobenzoyl)-7-methylpyrido[1,2-a]benzimidazol-1(5H)-one

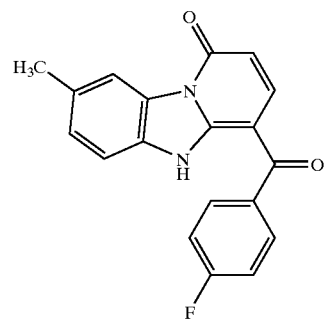

-continued

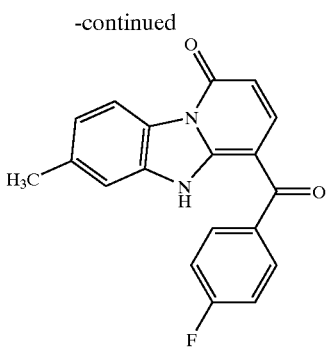

The compound is prepared as described in example 20 with 70 mg (0.26 mmol) of 1-(4-Fluorophenyl)-2-(5-methyl-1H-benzimidazol-2-yl)ethanone (example XXXV), 28.2 mg (0.52 mmol) of sodium methylate and 22 mg (0.26 mmol) methyl propiolate; a mixture of regioisomers is obtained.

Yield: 30.1 mg (27.7% of th.)

$^1$H-NMR (300 MHz, DMSO-d$_6$): δ=2.5 (s, 3H), 5.93–6.02 (m, 1H), 7.24–7.79 (m, 8H), 8.49–8.58 (m, 1H), 13.28 (s, 1H)

Example 30

8-Benzoyl-2-ethyl-3-methylimidazo[1,2-a]pyridin-5(1H)-one

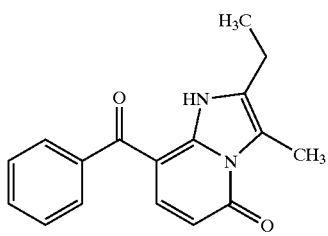

The compound is prepared as described in example 20 with 200 mg (0.76 mmol) of 2-(4-Ethyl-5-methyl-1H-imidazol-2-yl)-1-phenylethanone hydrochloride (example XVII), 50 mg (0.92 mmol) of sodium methylate and 63.5 mg (0.76 mmol) methyl propiolate.

Yield: 35 mg (16.5% of th.)

$^1$H-NMR (200 MHz, DMSO-d$_6$): δ=1.17 (t, 3H), 2.65 (s, 3H), 2.74 (q, 2H), 5.68 (d, 1H), 7.44–7.64 (m, 6H)

Example 31

2-Ethyl-8-(4-fluorobenzoyl)-3-methylimidazo[1,2-a]pyridin-5(1H)-one

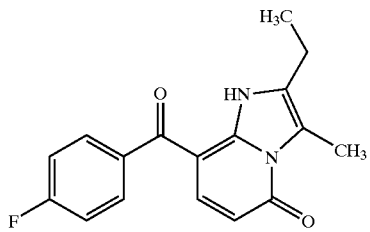

The compound is prepared as described in example 20 with 200 mg (0.71 mmol) of 2-(4-Ethyl-5-methyl-1H-imidazol-2-yl)-1-(4-fluorophenyl)ethanone hydrochloride (example XVIII), 50 mg (0.92 mmol) of sodium methylate and 59.5 mg (0.71 mmol) methyl propiolate.

Yield: 19 mg (9% of th.)

$^1$H-NMR (400 MHz, DMSO-d$_6$): δ=1.16 (t, 3H), 2.64 (s, 3H), 2.72 (q, 2H), 5.65 (d, 1H), 7.31–7.38 (m, 2H), 7.50 (d, 1H), 7.61–7.67 (m, 2H)

Example 32

4-Benzoyl-6-methyl-6,7,8,9-tetrahydropyrido[1,2-a]benzimidazol-1(5H)-one

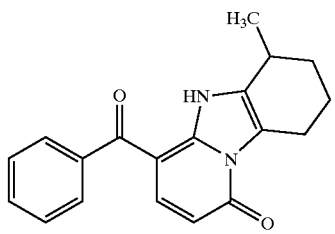

The compound is prepared as described in example 20 with 232 mg (0.80 mmol) of 2-(4-Methyl-4,5,6,7-tetrahydro-1H-benzimidazol-2-yl)-1-phenylethanone hydrochloride (example XIX), 50 mg (0.92 mmol) of sodium methylate and 67 mg (0.80 mmol) methyl propiolate.

Yield: 60 mg (24.6% of th.)

$^1$H-NMR (400 MHz, DMSO-d$_6$): δ=1.30 (d, 3H), 1.49–1.58 (m, 1H), 1.70–1.94 (m, 3H), 2.95–3.29 (m, 3H), 5.67 (d, 1H), 7.47–7.63 (m, 6H)

Example 33

4-(2,5-Difluorobenzoyl)-6,7,8,9-tetrahydropyrido[1,2-a]benzimidazol-1(5H)-one

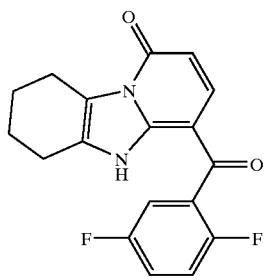

The compound is prepared as described in example 20 with 500 mg (1.81 mmol) of 1-(2,5-Difluorophenyl)-2-(4,5,6,7-tetrahydro-1H-benzimidazol-2-yl)ethanone (example XXXXII), 195.5 mg (3.62 mmol) of sodium methylate and 152.2 mg (1.81 mmol) methyl propiolate.

Yield: 31 mg (5% of th.)

$^1$H-NMR (400 MHz, DMSO-d$_6$): δ=1.73–1.83 (m, 4H), 2.62–2.71 (m, 2H), 3.13–3.20 (m, 2H), 5.66 (d, 1H), 7.28–7.45 (m, 4H), 12.91 (s, 1H)

Example 34

4-(4-Bromobenzoyl)-6,7,8,9-tetrahydropyrido[1,2-a]benzimidazol-1(5H)-one

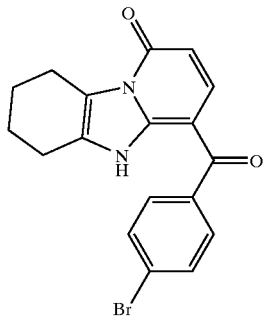

The compound is prepared as described in example 20 with 500 mg (1.57 mmol) of 1-(4-Bromophenyl)-2-(4,5,6,7-tetrahydro-1H-benzimidazol-2-yl)ethanone (example XXXVI), 169.2 mg (3.13 mmol) of sodium methylate and 131.7 mg (1.57 mmol) methyl propiolate.

Yield: 39.1 mg (5.6% of th.)

$^1$H-NMR (300 MHz, DMSO-$d_6$): δ=1.71–1.84 (m, 4H), 2.63–2.71 (m, 2H), 3.13–3.21 (m, 2H), 5.66 (d, 1H), 7.47–7.55 (m, 3H), 7.69–7.75 (m, 2H), 12.81 (s, 1H)

Example 35

4-(3,4-Difluorobenzoyl)-6,7,8,9-tetrahydropyrido[1,2-a]benzimidazol-1(5H)-one

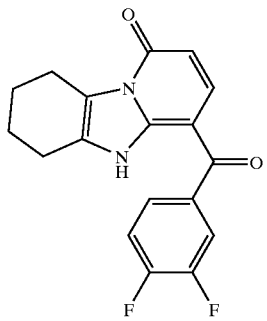

The compound is prepared as described in example 20 with 200 mg (0.72 mmol) of 1-(3,4-Difluorophenyl)-2-(4,5,6,7-tetrahydro-1H-benzimidazol-2-yl)ethanone (example XXXVII), 78.2 mg (1.45 mmol) of sodium methylate and 60.9 mg (0.72 mmol) methyl propiolate.

Yield: 13.1 mg (5.2% of th.)

$^1$H-NMR (300 MHz, DMSO-$d_6$): δ=1.71–1.85 (m, 4H), 2.63–2.72 (m, 2H), 3.14–3.22 (m, 2H), 5.67 (d, 1H), 7.40–7.68 (m, 4H), 12.82 (s, 1H)

Example 36

4-(3-Bromobenzoyl)-6,7,8,9-tetrahydropyrido[1,2-a]benzimidazol-1(5H)-one

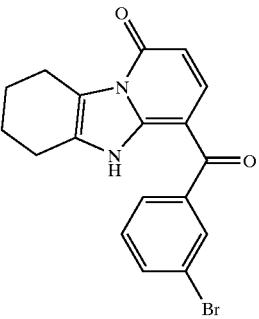

The compound is prepared as described in example 20 with 232.4 mg (0.73 mmol) of 1-(3-bromophenyl)-2-(4,5,6,7-tetrahydro-1H-benzimidazol-2-yl)ethanone (example XXXVIII), 78.7 mg (1.46 mmol) of sodium methylate and 61.2 mg (0.73 mmol) methyl propiolate.

Yield: 25 mg (9.3% of th.)

$^1$H-NMR (300 MHz, DMSO-$d_6$): δ=1.71–1.84 (m, 4H), 2.64–2.72 (m, 2H), 3.14–3.21 (m, 2H), 5.68 (d, 1H), 7.44–7.58 (m, 3H), 7.68–7.78 (m, 2H), 12.82 (s, 1H),

Example 37

4-(3-Chlorobenzoyl)-6,7,8,9-tetrahydropyrido[1,2-a]benzimidazol-1(5H)-one

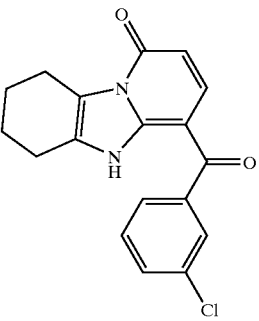

The compound is prepared as described in example 20 with 559.9 mg (2.03 mmol) of 1-(3-Chlorophenyl)-2-(4,5,6,7-tetrahydro-1H-benzimidazol-2-yl)ethanone (example XXXIX), 220.2 mg (4.08 mmol) of sodium methylate and 171.3 mg (2.03 mmol) methyl propiolate.

Yield: 163.8 mg (22.7% of th.)

$^1$H-NMR (300 MHz, DMSO-$d_6$): δ=1.71–1.85 (m, 4H), 2.62–2.73 (m, 2H), 3.12–3.23 (m, 2H), 5.67 (d, 1H), 7.43–7.66 (m, 5H), 12.82 (s, 1H)

Example 38

4-(2,4-Difluorobenzoyl)-6,7,8,9-tetrahydropyrido[1,2-a]benzimidazol-1(5H)-one

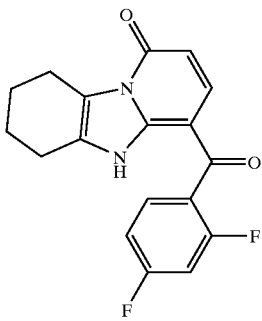

The compound is prepared as described in example 25 with 500 mg (1.81 mmol) of 1-(2,4-Difluorophenyl)-2-(4,5,6,7-tetrahydro-1H-benzimidazol-2-yl)ethanone (example XXXXIII), 195.5 mg (3.62 mmol) of sodium methylate and 152.2 mg (1.81 mmol) methyl propiolate.

Yield: 31.4 mg (5% of th.)

$^1$H-NMR (300 MHz, DMSO-$d_6$): δ=1.71–1.86 (m, 4H), 2.62–2.74 (m, 2H), 3.11–3.23 (m, 2H), 5.66 (d, 1H), 7.17–7.60 (m, 4H), 12.86 (s, 1H)

The compound is prepared as described in example 6 with 76 mg (1.09 mmol) of propiolic acid, 211.3 mg (1.30 mmol) of 1-(1H-imidazol-1-ylcarbonyl)-1H-imidazole and 200 mg (0.72 mmol) of 1-(2,4-Difluorophenyl)-2-(4,5,6,7-tetrahydro-1H-benzimidazol-2-yl)ethanone (example XXXXIII).

Yield: 70 mg (29.5% of th.)

Example 39

4-(4-Fluorobenzoyl)-6,7,8,9-tetrahydropyrido[1,2-a]benzimidazol-1(5H)-one

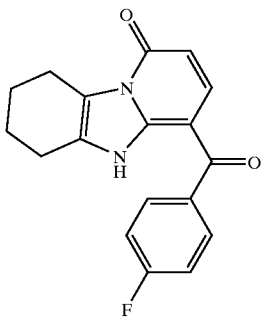

The compound is prepared as described in example 20 with 450 mg (1.74 mmol) of 1-(4-Fluorophenyl)-2-(4,5,6,7-tetrahydro-1H-benzimidazol-2-yl)ethanone (example XXXXIV), 188.2 mg (3.84 mmol) of sodium methylate and 146.5 mg (1.74 mmol) methyl propiolate.

Yield: 181.5 mg (32.5% of th.)

$^1$H-NMR (300 MHz, DMSO-$d_6$): δ=1.72–1.86 (m, 4H), 2.62–2.73 (m, 2H), 3.14–3.23 (m, 2H), 5.67 (d, 1H), 7.29–7.40 (m, 2H), 7.52 (d, 1H), 7.60–7.69 (m, 2H), (s, 1H)

Example 40

4-(2-Methylbenzoyl)-6,7,8,9-tetrahydropyrido[1,2-a]benzimidazol-1(5H)-one

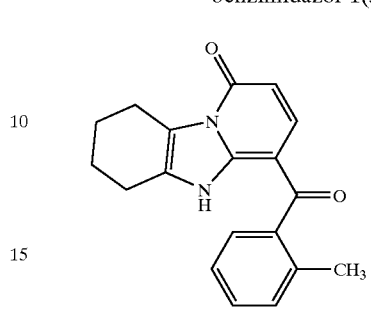

The compound is prepared as described in example 20 with 1450 mg (5.90 mmol) of 1-(2-Methylphenyl)-2-(4,5,6,7-tetrahydro-1H-benzimidazol-2-yl)ethanone (example XXXX), 637.2 mg (11.80 mmol) of sodium methylate and 495.8 mg (5.90 mmol) methyl propiolate.

Yield: 479.3 mg (26.5% of th.)

$^1$H-NMR (300 MHz, DMSO-$d_6$): δ=1.72–1.85 (m, 4H), 2.21 (s, 3H) 2.64–2.73 (m, 2H), 3.14–3.22 (m, 2H), 5.61 (d, 1H), 7.12–7.42 (m, 5H), 12.84 (s, 1H)

Example 41

8-Benzoyl-3-methyl-2-propylimidazo[1,2-a]pyridin-5(1H)-one

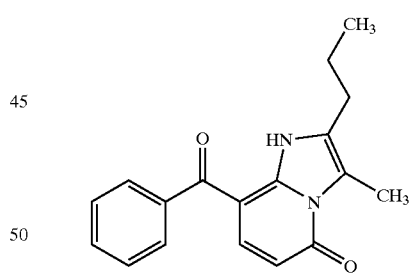

The compound is prepared as described in example 25 with 300 mg (1.08 mmol) of 2-(5-Methyl-4-propyl-1H-imidazol-2-yl)-1-phenylethanone hydrochloride (example XX), 60 mg (1.11 mmol) of sodium methylate and 90.5 mg (1.08 mmol) methyl propiolate.

Yield: 47 mg (14.9% of th.)

$^1$H-NMR (300 MHz, DMSO-$d_6$): δ=0.91 (t, 3H), 1.54–1.68 (m, 2H), 2.65 (s, 3H), 2.69 (t, 2H), 5.65 (d, 1H), 7.46–7.60 (m, 6H), 12.69 (s, 1H)

Example 42

2,3-Dimethyl-8-(3-methylbenzoyl)imidazo[1,2-a]pyridin-5(1H)-one

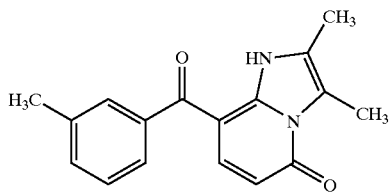

The compound is prepared as described in example 25 with 300 mg (1.13 mmol) of 2-(4,5-Dimethyl-1H-imidazol-2-yl)-1-(3-methylphenyl)ethanone hydrochloride (example XXII), 65 mg (1.20 mmol) of sodium methylate and 95.3 mg (1.13 mmol) methyl propiolate.

Yield: 45 mg (14.2% of th.)

$^1$H-NMR (300 MHz, DMSO-d$_6$): δ=2.29 (s, 3H), 2.39 (s, 3H), 2.63 (s, 3H), 5.64 (d, 1H), 7.30–7.44 (m, 4H), 7.50 (d, 1H), 12.69 (s, 1H)

Example 43

8-(2,4-Difluorobenzoyl)-2,3-dimethylimidazo[1,2-a]pyridin-5(1H)-one

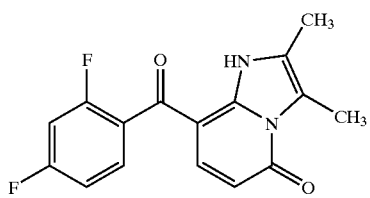

The compound is prepared as described in example 25 with 300 mg (1.05 mmol) of 2-(4,5-Dimethyl-1H-imidazol-2-yl)-1-(3-methylphenyl)ethanone hydrochloride (example XXIII), 65 mg (1.20 mmol) of sodium methylate and 88 mg (1.05 mmol) methyl propiolate.

Yield: 155 mg (49% of th.)

$^1$H-NMR (300 MHz, DMSO-d$_6$): δ=2.29 (s, 3H), 2.62 (s, 3H), 5.66 (d, 1H), 7.17–7.44 (m, 3H), 7.48–7.59 (m, 1H), 12.78 (s, 1H)

Example 44

8-Benzoyl-3-methyltimidazo[1,2-a]pyridin-5(1H)-one

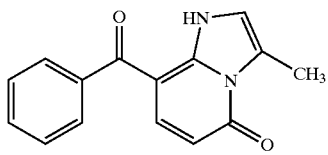

The compound is prepared as described in example 25 with 349.2 mg (1.48 mmol) of 2-(5-Methyl-1H-imidazol-2-yl)-1-phenylethanone hydrochloride (example XXIV), 90 mg (1.67 mmol) of sodium methylate and 124 mg (1.48 mmol) methyl propiolate.

Yield: 11 mg (3% of th.)

$^1$H-NMR (300 MHz, DMSO-d$_6$): δ=2.68 (s, 3H), 5.67 (d, 1H), 7.22–7.27 (m, 1H), 7.47–7.60 (m, 6H), 12.69 (s, 1H)

Example 45

4-(2-Chlorobenzoyl)-6,7,8,9-tetrahydropyrido[1,2-a]benzimidazol-1(5H)-one

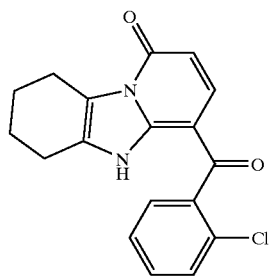

The compound is prepared as described in example 25 with 500 mg (1.15 mmol) of 1-(2-Chlorophenyl)-2-(4,5,6,7-etrahydro-1H-benzimidazol-2-yl)ethanone (example XXXXV), 124.5 mg (2.30 mmol) of sodium methylate and 96.8 mg (1.15 mmol) methyl propiolate.

Yield: 33 mg (8.8% of th.)

$^1$H-NMR (200 MHz, DMSO-d$_6$): δ=1.70–1.90 (m, 4H), 2.58–2.77 (m, 2H), 3.08–3.26 (m, 2H), 5.65 (d, 1H), 7.10 (d, 1H), 7.36–7.63 (m, 4H), 12.92 (s, 1H)

Example 46

4-(4-Chlorobenzoyl)-6,7,8,9-tetrahydropyrido[1,2-a]benzimidazol-1(5H)-one

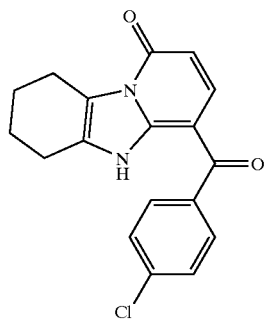

The compound is prepared as described in example 25 with 80 mg (0.23 mmol) of 1-(4-Chlorophenyl)-2-(4,5,6,7-tetrahydro-1H-benzimidazol-2-yl)ethanone hydrochloride (example XXXXI), 19.5 mg (0.46 mmol) of sodium methylate and 96.8 mg (0.23 mmol) methyl propiolate.

Yield: 12.6 mg (16.6% of th.)

LC-MS (C): R$_t$=4.03 min M (ESIpos): m/z=327.2 (M+H)$^+$

Example 47

4-(4-Methylbenzoyl)-6,7,8,9-tetrahydropyrido[1,2-a]benzimidazol-1(5H)-one

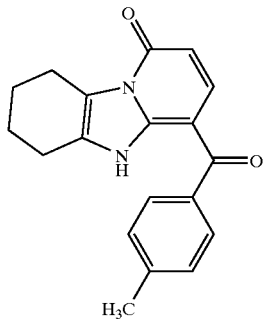

The compound is prepared as described in example 25 with 500 mg (1.49 mmol) of 1-(4-methylphenyl)-2-(4,5,6,7-tetrahydro-1H-benzimidazol-2-yl)ethanone hydrochloride (example IL), 160.7 mg (2.98 mmol) of sodium methylate and 125 mg (1.49 mmol) methyl propiolate.

Yield: 28.8 mg (6.3% of th.)

$^1$H-NMR (200 MHz, DMSO-d$_6$): δ=1.70–1.87 (m, 4H), 2.39 (s, 3H), 2.60–2.75 (m, 2H), 3.11–3.25 (m, 2H), 5.65 (d, 1H), 7.25–7.60 (m, 5H), 12.79 (s, 1H)

Example 48

4-(3-Fluorobenzoyl)-6,7,8,9-tetrahydropyrido[1,2-a]benzimidazol-1(5H)-one

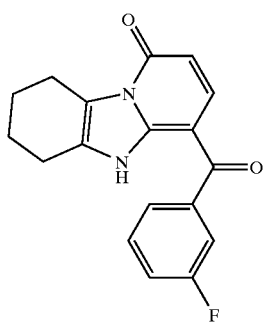

The compound is prepared as described in example 25 with 200 mg (0.51 mmol) of 1-(3-Fluorophenyl)-2-(4,5,6,7-tetrahydro-1H-benzimidazol-2-yl)ethanone hydrochloride (example XXXXVI), 55.2 mg (1.02 mmol) of sodium methylate and 42.9 mg (0.51 mmol) methyl propiolate.

Yield: 62.9 mg (38.5% of th.)

$^1$H-NMR (300 MHz, DMSO-d$_6$): δ=1.72–1.86 (m, 4H), 2.63–2.74 (m, 2H), 3.13–3.23 (m, 2H), 5.65 (d, 1H), 7.33–7.44 (m, 3H), 7.48–7.61 (m, 2H), 12.82 (s, 1H)

Example 49

4-(3-Methylbenzoyl)-6,7,8,9-tetrahydropyrido[1,2-a]benzimidazol-1(5H)-one

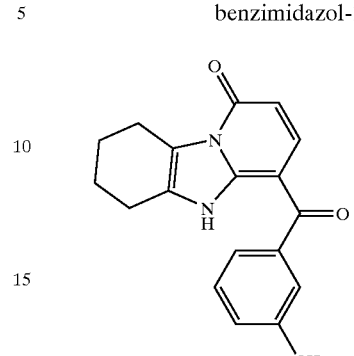

The compound is prepared as described in example 25 with 200 mg (0.63 mmol) of 1-(3-Methylphenyl)-2(4,5,6,7-tetrahydro-1H-benzimidazol-2-yl)ethanone hydrochloride (example XXXXVIII, 68.4 mg (1.27 mmol) of sodium methylate and 53.2 mg (0.63 mmol) methyl propiolate.

Yield: 83.6 mg (40% of th.)

$^1$H-NMR (300 MHz, DMSO-d$_6$): δ=1.72–1.84 (m, 4H), 2.39 (s, 3H) 2.63–2.72 (m, 2H), 3.13–3.22 (m, 2H), 5.65 (d, 1H), 7.28–7.55 (m, 5H), 12.77 (s, 1H)

Example 50

4-(2-Fluorobenzoyl)-6,7,8,9-tetrahydropyrido[1,2-a]benzimidazol-1(5H)-one

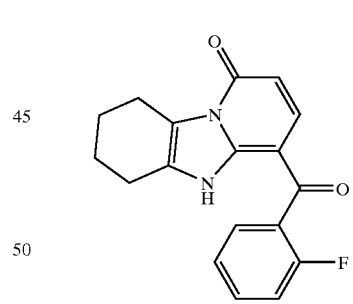

The compound is prepared as described in example 20 with 200 mg (0.54 mmol) of 1-(2-Fluorophenyl)-2-(4,5,6,7-tetrahydro-1H-benzimidazol-2-yl)ethanone hydrochloride (example XXXXVII, 58.6 mg (1.08 mmol) of sodium methylate and 45.6 mg (0.54 mmol) methyl propiolate.

Yield: 8.1 mg (4.8% of th.)

LC-MS (C): R$_t$=3.66 min

M (ESIpos): m/z=311.2 (M+H)$^+$

Example 51

8-(3-Chlorobenzoyl)-2,3-dimethylimidazo[1,2-a]pyridin-5(1H)-one

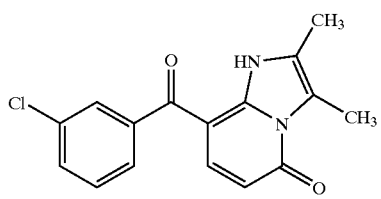

The compound is prepared as described in example 20 with 200 mg (0.70 mmol) of 1-(3-Chlorophenyl)-2-(4,5-dimethyl-1H-imidazol-2-yl)ethanone hydrochloride (example XXV), 65 mg (1.20 mmol) of sodium methylate and 59 mg (0.70 mmol) methyl propiolate.

Yield: 34 mg (16.1% of th.)

$^1$H-NMR (200 MHz, DMSO-$d_6$): δ=2.28 (s, 3H), 2.62 (s, 3H), 5.65 (d, 1H), 7.41–7.70 (m, 5H), 12.77 (s, 1H)

Example 52

8-Benzoyl-3-bromoimidazo[1,2-a]pyridin-5(1H)-one

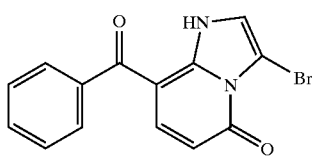

40 mg (0.12 mmol) of 3-bromo-5chloroimidazo[1,2-a]pyridin-8-yl)(phenyl)methanone (example L) are dissolved in 5 ml of potassium hydroxide—solution (10% in water) and 5 ml of ethanol. The mixture is stirred for 24 h at rt. The solvent is evaporated under vacuum and water is added to the crude. The solution is extracted for with ethyl acetate. The collected organic phases are reextracted with brine solution and dried over sodium sulfate. The solvent is evaporated under vacuum and the crude is purified over preparative HPLC (RP18-Column, eluent: acetonitrilewater-gradient) to yield 1.6 mg (4.2% of th.) 8-Benzoyl-3-bromoimidazo[1,2-a]pyridin-5(1H)-one.

$^1$H-NMR (300 MHz, DMSO-$d_6$): δ=5.73 (d, 1H), 7.48–7.71 (m, 7H), 13.17 (s, 1H)

Example 53

8-(4-Fluorobenzoyl)-3-methyl-2-phenylimidazo[1,2-a]pyridin-5(1H)-one

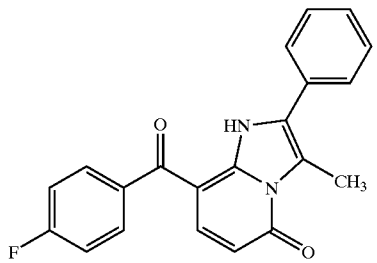

The compound is prepared as described in example 25 with 300 mg (0.91 mmol) of 1-(4-fluorophenyl)-2-(4-methyl-5-phenyl-1H-imidazol-2-yl)ethanone hydrochloride (example LI), 90 mg (1.80 mmol) of sodium methylate and 76 mg (0.91 mmol) methyl propiolate.

Yield: 15 mg (4.8% of th.)

$^1$H-NMR (200 MHz, DMSO-$d_6$): δ=2.78 (s, 3H), 5.75 (d, 1H), 7.35 (m, 2H), 7.50–7.80 (m, 8H), 12.78 (s, 1H)

Example 54

4-[3-(Trifluoromethyl)benzoyl]-6,7,8,9-tetrahydropyrido[1,2-a]benzimidazol-1(5H)-one

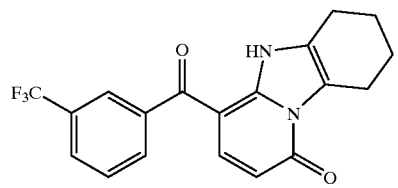

The compound is prepared as described in example 25 with 500 mg (1.62 mmol) of 2-(4,5,6,7-tetrahydro-1H-benzimidazol-2-yl)-1-[3-(trifluoromethyl)phenyl]ethanone (example LII), 175 mg (3.25 mmol) of sodium methylate and 136 mg (1.62 mmol) methyl propiolate.

Yield: 151 mg (25.8% of th.)

$^1$H-NMR (300 MHz, DMSO-$d_6$): δ=1.71–1.84 (m, 4H), 2.64–2.72 (m, 2H), 3.14–3.21 (m, 2H), 5.68 (d, 1H), 7.46 (d, 1H), 7.65–8.00 (m, 4H), 12.85 (s, 1H)

Example 55

4-(4-Methoxybenzoyl)-6,7,8,9-tetrahydropyrido[1,2-a]benzimidazol-1(5H)-one

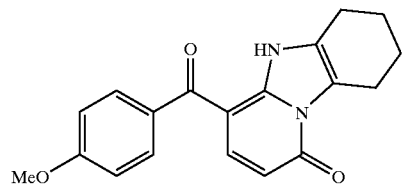

The compound is prepared as described in example 25 with 200 mg (0.74 mmol) of 1-(4-methoxyphenyl)-2-(4,5,6,7-tetrahydro-1H-benzimidazol-2-yl)ethanone (example LIII), 80 mg (1.48 mmol) of sodium methylate and 62 mg (0.74 mmol) methyl propiolate.

Yield: 32 mg (12.4% of th.)

$^1$H-NMR (300 MHz, DMSO-$d_6$): δ=1.71–1.84 (m, 4H), 2.64–2.72 (m, 2H), 3.14–3.21 (m, 2H), 3.84 (s, 3H), 5.65 (d, 1H), 7.10 (m, 2H), 7.50–7.70 (m, 3H), 12.73 (s, 1H)

Example 56

4-(2,4-Difluorobenzoyl)-7-methyl-6,7,8,9-tetrahydropyrido[1,2-a]benzimidazol-1(5H)-one

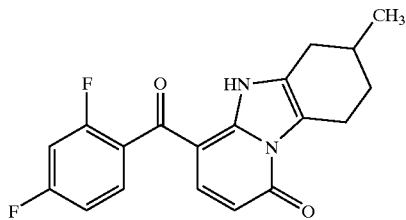

and

Example 57

4-(2,4-Difluorobenzoyl)-8-methyl-6,7,8,9-tetrahydropyrido[1,2-a]benzimidazol-1(5H)-one)

The compound is prepared as described in example 11 with 138 mg (1.97 mmol) of propiolic acid, 383.6 mg (2.37 mmol) of 1-(1H-imidazol-1-ylcarbonyl)-1H-imidazole and 382 mg (1.31 mmol) of 1-(2,4-difluorophenyl)-2-(5-methyl-4,5,6,7-tetrahydro-1H-benzimidazol-2-yl)ethanone (example LIV). The isomers are isolated after purification over preparative HPLC (Daicel Chiralpak AD, eluent: isohexane-ethanol v/v 60:40):

Example 56-1

Yield: 20 mg (4.4% of th.) of 4-(2,4-Difluorobenzoyl)-7-methyl-6,7,8,9-tetrahydropyrido[1,2-a]benzimidazol-1(5H)-one)

$R_t$=5.74 min (Daicel Chiralpak AD)

$^1$H-NMR (300 MHz, DMSO-$d_6$): δ=1.05 (d, 3H), 1.45 (m, 1H) 1.90 (m, 2H), 2.20 (m, 1H), 2.80 (m, 1H), 3.00 (m, 1H), 3.40 (m, 1H), 5.60 (d, 1H), 7.20–7.50 (m, 1H), 12.80 (s, 1H)

Example 56-2

Yield: 20 mg (4.4% of th.) of 4-(2,4-Difluorobenzoyl)-7-methyl-6,7,8,9-tetrahydropyrido[1,2-a]benzimidazol-1(5H)-one)

$R_t$=9.34 min (Daicel Chiralpak AD)

$^1$H-NMR (300 MHz, DMSO-$d_6$): δ=1.05 (d, 3H), 1.45 (m, 1H) 1.90 (m, 2H), 2.20 (m, 1H), 2.80 (m, 1H), 3.00 (m, 1H), 3.40 (m, 1H), 5.60 (d, 1H), 7.20–7.40 (m, 3H), 7.50 (m, 1H), 12.80 (s, 1H)

Example 57-1

Yield: 20 mg (4.4% of th.) of 4-(2,4-Difluorobenzoyl)-8-methyl-6,7,8,9-tetrahydropyrido[1,2-a]benzimidazol-1(5H)-one)

$R_t$=13.02 min (Daicel Chiralpak AD)

$^1$H-NMR (300 MHz, DMSO-$d_6$): δ=1.10 (d, 3H), 1.45 (m, 1H) 1.90 (m, 2H), 2.70 (m, 3H), 3.45 (m, 1H), 5.65 (d, 1H), 7.15–7.40 (m, 3H), 7.50 (m, 1H), 12.90 (s, 1H)

Example 57-2

Yield: 20 mg (4.4% of th.) of 4-(2,4-Difluorobenzoyl)-8-methyl-6,7,8,9-tetrahydropyrido[1,2-a]benzimidazol-1(5H)-one)

$R_t$=18.33 min (Daicel Chiralpak AD)

$^1$H-NMR (300 MHz, DMSO-$d_6$): δ=1.10 (d, 3H), 1.45 (m, 1H) 1.90 (m, 2H), 2.70 (m, 3H), 3.45 (m, 1H), 5.65 (d, 1H), 7.15–7.40 (m, 3H), 7.50 (m, 1H), 12.90 (s, 1H)

C. OPERATIVE EXAMPLES RELATING TO PHARMACEUTICAL COMPOSITIONS

The compounds according to the invention can be converted into pharmaceutical preparations as follows:

Tablet

Composition 100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate. Tablet weight 212 mg, diameter 8 mm, curvature radius 12 mm.

Preparation

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension

Composition 1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation

The Rhodigel is suspended in ethanol and the active component is added to the suspension. The water is added with stirring. Stirring is continued for about 6 h until the swelling of the Rhodigel is complete.

What is claimed is:
1. A compound of general formula (I)

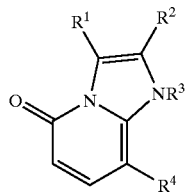

wherein $R^1$ represents hydrogen, halogen, $C_1$–$C_6$-alkyl, $C_6$–$C_{10}$-aryl, $C_3$–$C_8$-cycloalkyl, or $C_1$–$C_6$-alkoxy, wherein $R^1$ can optionally be substituted with 1 to 3 substituents $R^{1-1}$, wherein $R^{1-1}$ is halogen, amino, mono- or di-$C_1$–$C_6$-alkylamino , or $C_1$–$C_6$-alkoxy, $R^2$ represents hydrogen, halogen, $C_1$–$C_6$-alkyl, $C_6$–$C_{10}$-aryl, $C_3$–$C_8$-cycloalkyl, $C_1$–$C_6$-alkoxy, wherein $R^2$ can optionally be substituted with 1 to 3 substituents $R^{2-1}$, wherein $R^{2-1}$ is halogen, amino, mono- or di-$C_1$–$C_6$-alkylamino, or $C_1$–$C_6$-alkoxy, or $R^1$ and $R^2$ together with the carbon atoms to which they are attached form a $C_6$–$C_{10}$-aryl- or $C_5$–$C_8$-cycloalkyl-ring, wherein the ring is optionally substituted with $C_1$–$C_6$-alkyl, $C_1$–$C_6$-alkoxy, halogen, cyano, amino, mono- or di-$C_1$–$C_6$-alkylamino, or $COR^{2-2}$, wherein $R^{2-2}$ is OH, $C_1$–$C_6$-alkoxy, $C_6$–$C_{11}$-aryloxy, amino, or mono- or di-$C_1$–$C_6$-alkylamino, $R^3$ represents hydrogen or $C_1$–$C_6$-alkyl, $R^4$ represents —$COR^{4-1}$, wherein $R^{4-1}$ represents $C_6$–$C_{10}$-aryl, wherein $R^{4-1}$ can optionally be substituted with 1 to 3 substituents selected from the group consisting of halogen, amino, $C_1$–$C_6$-alkyl, $C_1$–$C_6$-alkoxy, mono or di-$C_1$–$C_6$-alkylamino, trifluoromethyl, cyano, nitro and hydroxy, with the proviso, that the compound is not 8-benzoyl-H-imidazo[1,2,-a]pyridin-5-one or
8-benzoyl-1-methylimidazo[1,2,-a]pyridin-5-one,
or a pharmaceutically acceptable salt thereof.

2. The compound of formula (I) according to claim 1, wherein $R^1$ represents hydrogen, $C_1$–$C_6$-alkyl or $C_3$–$C_8$-cycloalkyl, wherein $R^1$ can optionally be substituted with 1 to 3 substituents $R^{1-1}$, wherein $R^{1-1}$ is $C_1$–$C_6$-alkoxy, $R^2$ represents hydrogen, $C_1$–$C_6$-alkyl or $C_3$–$C_8$-cycloalkyl, wherein $R^2$ can optionally be substituted with 1 to 3 substituents $R^{2-1}$, wherein $R^{2-1}$ is $C_1$–$C_6$-alkoxy, or $R^1$ and $R^2$ together with the carbon atoms to which they are attached form a $C_6$–$C_{10}$-aryl- or $C_5$–$C_8$-cycloalkyl-ring, wherein the ring is optionally substituted with $C_1$–$C_6$-alkyl, $C_1$–$C_6$-alkoxy, or halogen, $R^3$ represents hydrogen, $R^4$ represents —$COR^{4-1}$, wherein $R^{4-1}$ represents $C_6$–$C_{10}$-aryl, wherein $R^{4-1}$ can optionally be substituted with 1 to 3 substituents selected from the group consisting of halogen, $C_1$–$C_6$-alkyl, $C_1$–$C_6$-alkoxy, trifluoromethyl or hydroxy, with the proviso, that the compound is not
8-benzoyl-H-imidazo[1,2,-a]pyridin-5-one
or a pharmaceutically acceptable salt thereof.

3. The compound of formula (I) according to claim 1, wherein $R^1$ represents hydrogen or $C_1$–$C_6$-alkyl, $R^2$ represents hydrogen or $C_1$–$C_6$-alkyl, or $R^1$ and $R^2$ together with the carbon atoms to which they are attached form a $C_5$–$C_8$-cycloalkyl-ring, wherein the ring is optionally substituted with $C_1$–$C_6$-alkyl, $R^3$ represents hydrogen, $R^4$ represents —$COR^{4-1}$, wherein $R^{4-1}$ represents $C_6$–$C_{10}$-aryl, wherein $R^{4-1}$ can optionally be substituted with 1 to 3 substituents selected from the group consisting of halogen and $C_1$–$C_6$-alkyl, with the proviso, that the compound is not 8-benzoyl-H-imidazo[1,2,-a]pyridin-5-one
or a pharmaceutically acceptable salt thereof.

4. The compound of formula (I) according to claim 1, wherein $R^3$ is hydrogen and with the proviso that the compound is not 8-benzoyl-H-imidazo[1,2-a]pyridin-5-one.

5. The compound of formula (I) according to claim 1, wherein $R^4$ is —$C(O)C_6H_5$, wherein $R^4$ can optionally be substituted with 1 to 3 substituents selected from the group consisting of halogen, amino, $C_1$–$C_6$-alkyl, $C_1$–$C_6$-alkoxy, mono or di-$C_1$–$C_6$-alkylamino, trifluoromethyl, and cyano.

6. The compound of formula (I) according to claim 1, wherein $R^1$ and $R^2$ together with the carbon atoms to which they are attached form a substituted cyclohexyl-ring.

7. A process for synthesizing a compound of formular (I) of claim 1, characterized in that a compound of formula (II)

characterized in that a compound of formula (II)

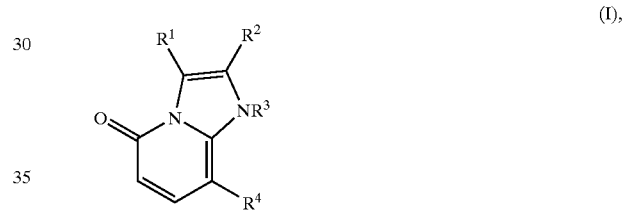

wherein $R^1$, $R^2$ and $R^4$ have the meaning described above in claim 1, is reacted (A) with $C_1$–$C_6$-alkyl propiolate in the presence of a base, or (B) with $C_1$–$C_6$-alkyl propiolate in absence of a base, or (C) with 3-oxopropionic $C_1$–$C_6$-alkyl ester or (D) with a compound of formula (IV)

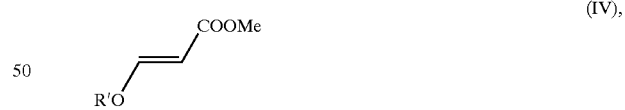

wherein R' is $C_1$–$C_6$-alkyl or $C_1$–$C_6$-alkylcarbonyl, or (E) with propiolic acid in the presence of carbonyldiimidazole.

8. A composition containing at least one compound of formula (I) according to claim 1 and a pharmacologically acceptable diluent.

9. A process for treating acute and chronic inflammatory conditions selected from and COPD in a human or animal, comprising administering to the human or animal in need thereof an antiinflammatorily effective amount of at least one compound according to claim 1.

10. The process of claim 9 wherein the inflammatory condition is COPD.

* * * * *